(12) United States Patent
Reichelt et al.

(10) Patent No.: US 8,058,285 B2
(45) Date of Patent: Nov. 15, 2011

(54) SUBSTITUTED PYRIDO [3', 2': 4, 5] THIENO [3, 2-D] PYRIMIDINES AND PYRIDO [3', 2': 4, 5] FURO [3, 2-D] PYRIMIDINES USED AS INHIBITORS OF THE PDE-4 AND/OR THE RELEASE OF TNF-ALPHA

(75) Inventors: Claudia Reichelt, Leipzig (DE); Alexander Ludwig, Leipzig (DE); Alexander Schulze, Großtreben-Zwethau (DE); Mohammed Daghish, Leipzig (DE); Siegfried Leistner, Leipzig (DE); Andreas Krödel, Leipzig (DE); Jochen Heinicke, Leipzig (DE)

(73) Assignee: The Medicines Company (Leipzig) GmbH, Leipzig (DE)

( * ) Notice: Subject to any disclaimer, the term of this patent is extended or adjusted under 35 U.S.C. 154(b) by 448 days.

(21) Appl. No.: 11/625,691

(22) Filed: Jan. 22, 2007

(65) Prior Publication Data

US 2008/0160028 A1    Jul. 3, 2008

Related U.S. Application Data

(63) Continuation-in-part of application No. PCT/EP2005/008030, filed on Jul. 22, 2005.

(30) Foreign Application Priority Data

Jul. 23, 2004  (EP) ................................. 04017542
Aug. 2, 2004  (EP) ................................. 04018272

(51) Int. Cl.
*A61K 31/505* (2006.01)
(52) U.S. Cl. .................................................. 514/267
(58) Field of Classification Search .............. 544/250; 514/267
See application file for complete search history.

(56) References Cited

FOREIGN PATENT DOCUMENTS

| EP | 1 277 738 | * | 4/2001 |
| EP | 1 277 738 | | 1/2003 |
| EP | 1 323 719 | | 7/2003 |

OTHER PUBLICATIONS

Vieweg, H., et al., Synthesis of 2,3-dihydroimidazo[1,2-c]- and 3,4-dihydro-2H-pyrimido[1,2- c]pyrido[3',2' :4,5]thieno[2,3-e]pyrimidines via 4-(w-hydroxyalkylamino) derivatives of pyridothienopyrimidines. Part 35. Polycyclic azines with heteroatoms in 1- and 3-position, Pharmazie 47(10), 751-4 (1992).*
Michael, J. M., New pyrido [3,2:4,5] thieno [3,2-D] pyrimidines of possible antimicrobial activity, Al-Azhar Bulletin of Science, 3(2), 767-75 (1992).*
Quintela, Jose M., et al., Synthesis and antiallergic activity of pyridothienopyrimidines, Bioorganic & Medicinal Chemistry 6(10), 1911-1925 (1998).*

Tornetta, Benedetto, et al., Synthesis and spectral behavior of pyridothienoisothiazole and pyridothienopyrimidine derivatives, Gazzetta Chimica Italiana, 108(1-2), 57-62 (1978).*
Peinador, et al., A Convenient Synthesis for Some New Pyrido[3',2':4:5]thieno-[3,2-d]pyrimidine Derivatives with Potential Biological Activity, J. Heterocyclic Chem., 29, 1693 (1992).*
Wolff, Manfred E., Burger's Medicinal Chemistry and Drug Discovery, Fifth Ed., vol. 1: Principles and Practice, John Wiley & Sons, 1995, 975.*

(Continued)

*Primary Examiner* — Andrew D Kosar
*Assistant Examiner* — Erich A Leeser
(74) *Attorney, Agent, or Firm* — Vedder Price P.C.; Thomas J. Kowalski; Eugenia Kiselgof

(57) ABSTRACT

The invention relates to compounds of general formula (I); 1a, 1 b, 1 c and 1 d. The invention also relates to a method for the production thereof, pharmaceutical preparations containing said compounds and/or physiologically compatible salts thereof which can be produced therefrom and/or solvates thereof, and to the pharmaceutical use of said compounds, salts or solvates thereof as inhibitors of phosphodiesterase 4. The compounds comprise active ingredients for the treatment of diseases which can have a positive influence by inhibiting the activity of phosphodiesterase 4 and/or TNFα-release, for example, in lymphocytes, eosinophile and basophile granulocytes, macrophages and mastocytes.

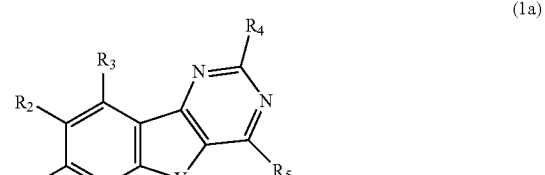

(1a)

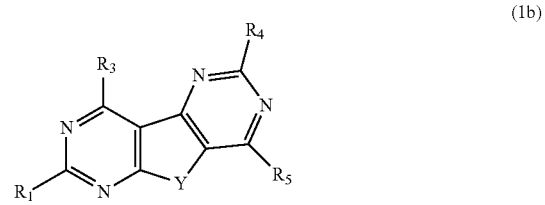

(1b)

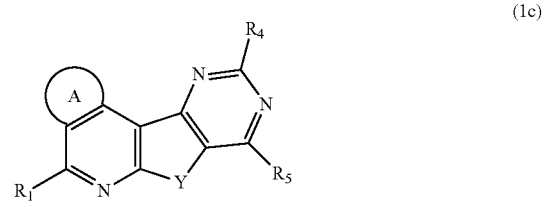

(1c)

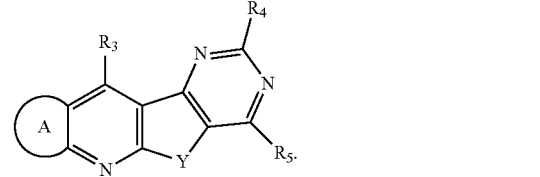

(1d)

2 Claims, 1 Drawing Sheet

OTHER PUBLICATIONS

Banker, Gilbert S. et al., Modem Pharmaceutics, Marcel Dekker, New York, 1996.*

Doherty, Phosphodiesterase 4 Inhibitors as Novel Anti-inflammatory Agents. Curr. Opin. Chem. Biol., 3, 466-473 (1999).*

Essayan, Cyclic Nucleotide Phosphodiesterase (PDE) Inhibitors and Immunomodulation, Biochem. Pharmacol., 57, 565-573 (1999).*

Dal Piaz, et al., Phosphodiesterase 4 Inhibitors, Structurally Unrelated to Rolipram, as Promising Agents for Treatment of Asthma and Other Pathologies, Eur. J. Med. Chem., 35, 463-480 (2000).*

Quintela, Jose M., et al., Synthesis and antiallergic activity of pyridothienopyrimidines, Bioorganic & Medicinal Chemistry 6(10), 1911-1925 (1998).*

José M. Quintela et al.: "Synthesis and Antiallergic Activity of Pyridothienopyrimidines" Bioorg. Med. Chem, Bd. 6, 1998, Seiten 1911-1925, XP002310819 Tabelle 1.

Peinador C et al: "A Convenient Synthesis for Some Pyrido 3', 2':4,5!thieno 3,2-d!pyrimi dine Derivatives with Potential Biological Activity" Journal of Heterocyclic Chemistry, Heterocorporation. Provo, US, Bd. 29, Dec. 1992, Seiten 1693-1702, XP002244954 ISSN: 0022-152X Verbindungen 8-18.

G. Wagner et al.: "Synthese von acylierten 4-Hydrazino-pyrido 3',2':4,5!thieno 3,2-d! pyrimidinen und tetracyclischen Verbindungen gleicher tricyclischer Grundstruktur und einem am Pyrimidinring annelierten Heterocyclus" Pharmazie, Bd. 48, 1993, Seiten 20-23, XP002310820 Verbindung 2b.

Vieweg H. et al.: "Synthese von 2,3-Dihydro-imidazo 1,2-c!-und 3,4-Dihydro-2H-pyrimido 1,2-c!-annelierten Pyrido 3',2':4,5!thieno 2,3-e! pyrimidinen aus 4-(omega-Hydroxyalkylamino)-Verbindungen von Pyridothienopyrimidinen" Pharmazie, Bd. 47, 1992, Seiten 751-754, XP002310821 Verbindung D2,D3,D5.

Database Chemcats Chemincal Abstracts Service, Columbus, Ohio, US; XP002352717 Order No. PHAR027215, PHAR058716 & "Synthetic and Natural Compounds Product List" (Mar. 17, 2004), Pharmeks Ltd., Chuksin Tupik 4, of. 15, Moscow, 125206, Russia.

Database Chemcats Chemical Abstracts Service, Columbus, Ohio, US; XP002352718 Order No. STOCK4S-39856, STOCK4S-17994, STOCK4S-31384 & "Interchim Intermediates" Jan. 18, 2005, Interchim, 211 Bis AV JF Kennedy, BP 1140, Montlucon, 03103, France.

Database Chemcats, Chemical Abstracts Service, Columbus, Ohio, US; XP002352719 Order No. PHAR094558 & "Ambinter Stock Screening Collection" Jul. 3, 2005, Ambinter, 50 Avenue De Versailles, Paris, F-75016, France.

Young Chul Park et al., "Wortmannin, a Specific Inhibitor of Phosphatidylinositol-3-kinase, Enhances LPS-Induced NO Production from Murine Peritoneal Macrophages" Article No. RC977722, pp. 692-696 (1997).

Gernot Schabbauer et al., "PI3K-Akt Pathway Suppresses Coagulation and Inflammation in Endotoxemic Mice" Oct. 2004, pp. 1963-1969.

Eun-Kyoung Choi et al., "Enhancement of cytokine-mediated NF-κb activation by phosphatidylinositol 3-kinase inhibitors in monocytic cells" pp. 908-915 (2006).

* cited by examiner

Control 7-(3,4-Dimethoxyphenyl)-4-ethoxy-9-methyl-2-piperazin-1-yl-pyrido[3',2':4,5]-thieno[3,2-d]pyrimidine hydrochloride

SUBSTITUTED PYRIDO [3', 2': 4, 5] THIENO [3, 2-D] PYRIMIDINES AND PYRIDO [3', 2': 4, 5] FURO [3, 2-D] PYRIMIDINES USED AS INHIBITORS OF THE PDE-4 AND/OR THE RELEASE OF TNF-ALPHA

This application is a continuation-in-part application of international patent application Serial No. PCT/EP2005/008030 filed Jul. 22, 2005, which published as PCT Publication No. WO 2006/010567 on Feb. 2, 2006, which claims benefit of European patent application Serial Nos. 04017542.4 filed Jul. 23, 2004 and 04018272.7 filed Aug. 2, 2004.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. Citation or identification of any document in this application is not an admission that such document is available as prior art to the present invention. It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention. The embodiments of the present invention are disclosed herein or are obvious from and encompassed by, the detailed description. The detailed description, given by way of example, but not intended to limit the invention solely to the specific embodiments described, may best be understood in conjunction with the accompanying drawings.

TECHNICAL FIELD

The invention relates to the following compounds of general formulae 1a, 1b, 1c and 1d,

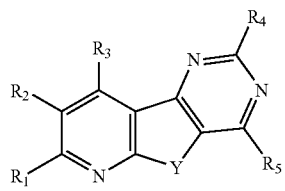

1a

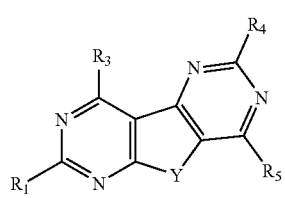

1b

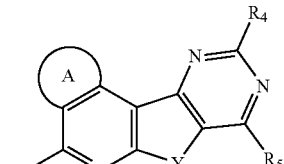

1c

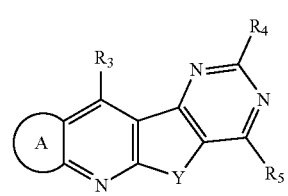

1d to processes for the production thereof, pharmaceutical preparations containing said compounds and/or physiologically compatible salts producible therefrom and/or the solvates thereof as well as to the pharmaceutical use of said compounds, the salts or solvates thereof as inhibitors of phosphodiesterase 4. The compounds represent active substances for treating diseases which can be positively influenced by inhibiting the activity of phosphodiesterase 4 and/or TNFα release, e.g. in lymphocytes, eosinophil and basophil granulocytes, macrophages and mast cells.

PRIOR ART

The cyclic nucleotides cAMP and cGMP are combined as intracellular second messengers and play a central role in the most different physiological and also in pathophysiological processes in living organisms. When the intracellular concentrations of these nucleotides are high, the latter bind to specific protein kinases, in particular to protein kinase A and protein kinase B, which they activate. The thus activated protein kinases then can phosphorylate a plurality of intracellular proteins which, in turn, decisively influence the cellular metabolism and the response of these cells to internal and external signals.

In the living cells, the cAMP and cGMP concentrations are predominantly determined by the synthesis and enzymatic degradation of these nucleotides. cAMP und cGMP are synthesized from ATP and GTP via the enzymes adenylate cyclase and guanylate cyclase which are activated in the cell membrane by G protein-linked receptors. These cyclic nucleotides are degraded in the cell by specific phosphodiesterases.

The phosphodiesterases (PDEs) comprise a large superenzyme family currently having 11 known types, which are, in turn, divided into numerous subtypes (isoforms) and even many more splice variants. These isoforms differ as regards their substrate specificity, enzyme kinetics, tissue specificity, sensitivity to inhibitors and activators and as regards their intracellular compartmenting (Giernbycz M A. *Phosphodiesterase 4 inhibitors and the treatment of asthma: where are we now and where do we go from here? Drugs* [2000]; 59, 193-212).

Since 1990, the pharmaceutical industry has shown a growing interest in identifying selective PDE inhibitors and developing them as active substance candidates for treating chronic respiratory diseases, for example.

According to the current standard of knowledge, cAMP specific PDE-4 is the most important isoenzyme of immunocompetent cells and smooth muscle cells of the pulmonary tissue. The PDE-4 family currently comprises four genes with the gene products PDE-4A, PDE-4B, PDE-4C and PDE-4D. PDE-4 specific isotypes were described for the first time by Nemoz et al. (Nemoz G, Prigent A F, Moueqqit M, Fougier S, Macovschi O, Pacheco H. *Selective inhibition of one of the cyclic AMP phosphordiesterases from rat brain by the neurotropic compound rolipram. Biochem Pharmacol* [1985]; 34 2997-3000). All subtypes are composed of a conserved catalytic domain having a length of about 270 amino acids and two additional regions of varying length (UCR1 and UCR2; upstream conserved region) within the N-terminus of the molecule (Engels P, Fichtel K, Lubbert H. *Expression and regulation of human and rat phosphodiesterase IV. FEBS Letters* [1994]; 350, 291-295). Another diversity in the expression of the PDE-4 isoforms results from alternative splice variants and different post-translational processing (Beavo J A, Conti M, Heaslip R J. *Multiple cyclic nucleotide phosphodiesterases. Mol Pharmakol* [1994]; 46, 399-405). These four subtypes are differentially expressed in different tissues und cells. PDE-4A to PDE-4D are present in most immunocompetent cells and in inflammatory cells. With the exception of PDE-4B the other PDE-4 types can also be detected in the epithelial cells of the airways. In the human brain there is also described a differenttial expression of the four subtypes as a function of certain anatomic regions.

In the past few years, numerous preclinical and clinical studies have been able to prove the modulation of inflammatory and immunocompetent cells by selective PDE-4 inhibitor, thus leading to the scientifically secured opinion as to the high therapeutic potential of specific PDE-4 inhibitors with widely differing inflammatory diseases, such as chronically obstructive pulmonary diseases (COPD), bronchial asthma, atopic dermatitis, rheumatoid arthritis (RA), cystic fibrosis (CF) and numerous neurological diseases (Doherty A M. *Phosphodiesterase 4 inhibitors as novel anti-inflammatory agents. Curr Opin Chem Biol* [1999]; 3, 466-473; Essayan D M. *Cyclic nucleotide phosphodiesterase (PDE) inhibitors and immunomodulation. Biochem Pharmacol* [1999]; 57, 565-573; Dal Piaz V, Giovannoni M P. *Phosphodiesterase 4 inhibitors, structurally unrelated to Rolipram, as promising agents for treatment of asthma and other pathologies. Eur J Med Chem* [2000]; 35, 463-480).

A central property of selective PDE-4 inhibitors is the inhibition of the release of the important pro-inflammatory cytokine TNFα from inflammatory cells (macrophages, mast cells, T-lymphocytes, basophil and eosinophil granulocytes) but also from fibroblasts, endothelial cells and astrocytes. TNFα, in turn, can stimulate further pro-inflammatory cytokines, such as the granulocyte-macrophage colony-stimulating factor (GM-CSF) and interleukins, in particular IL-1 and IL-8. In addition, TNFα activates neutrophil and eosinophil granulocytes, fibroblasts and endothelial cells which, in turn, secrete pro-inflammatory cytokines and proteases, mainly MMPs. Thus, all diseases where TNFα plays a central role in the disease process, are also a target for PDE-4 inhibitors.

It was possible to identify both PDE-3 and PDE-4A, B, D, but no PDE-4C subtypes, in eosinophil granulocytes. These cells play an important role in the pathophysiology of asthma and have therefore also been investigated intensely as to the PDE-4 inhibition. A selective PDE-4 inhibition effects a reduction of the release of reactive oxygen radicals and leukotriene $C_4$ (Sturton R G, Butt N M, Palfai S P, Tudhope S R, Abram T S, Fisher R, Braunlich G, Es-Sayed M. *Am J Respir Crit Care Med* [2000]; 161, A200). The synthesis of eosinophil-derived neurotoxin (EDN), of complement component $C5_a$ and platelet activating factor (PAF) is also reduced by a selective inhibition of PDE-4 (Hatzelmann A, Tenor H, Schudt C. *Differential effects of non-selective and selective phosphodiesterase inhibitors on human eosinophil functions. Br J. Pharmacol.* [1995]; 114, 821-831). As investigated in the most different animal models for asthma, PDE-4 inhibitors significantly block the penetration of eosinophil granulocytes, inhibit the accumulation of cytokines IL-4 and IL-5 in the broncho-alveolar lavage (BAL) and improve the function of the airways (Kanehiro A, Ikemura T, Makela M J, Lahn M, Joetham A, Dakhama A, Gelfand E W. *Inhibition of phosphodiesterase 4 attenuates airway hyperresponsiveness and airway inflammation in a model of secondary allergen challenge. Am J Respir Crit Care Med.* [2001]; 163, 173-184).

Neutrophil granulocytes play a key role in inflammatory diseases. They accumulate very rapidly in the inflammatory tissue and secrete a large number of biologically active mediators and enzymes.

In these cells, predominantly PDE-4 is detected as cAMP degrading enzyme (Wang P, Wu P, Ohleth K M, Egan R W, Billah M M. *Phosphodiesterase 4B2 is the predominant phosphodiesterase species and undergoes differential regulation of gene expression in human monocytes and neutrophils. Mol Pharmacol.* [1999]; 56 170-174). PDE-4 inhibitors suppress a plurality of defense functions of these cells, such as superoxide formation, degranulation, IL-8 release, adhesion molecule expression, a strongly reduced expression of the human lung elastase, of MMP-9 and the leukotriene $B_4$ synthesis (Barnette M S, Christensen S B, Essayan D M, Grous M, Prabhakar U, Rush J A, Kagey-Sobotka A, Torphy T J. *SB 207499 (Ariflo), a potent and selective second-generation phosphodiesterase 4 inhibitor: in vitro anti-inflammatory actions. J Pharmacol Exp Ther.* [1998]; 284, 420-426; Berends C, Dijkhuizen B, de Monchy J G, Dubois A E, Gerritsen J, Kauffman H F. *Inhibition of PAF-induced expression of CD11b and shedding of L-selectin on human neutrophils and eosinophils by the type IV selective PDE inhibitor, rolipram. Eur Respir J.* [1997]; 10, 1000-1007). A pathophysiological main consequence of this changed cell function by PDE-4 inhibitors can be seen in their strongly reduced adhesion and chemotaxis towards the focus of inflammation so that there is no penetration of the inflammatory cells.

PDE-4 inhibitors block in vivo neutrophilia in BAL in numerous COPD animal models and thus an essential pathological inflammatory pathway (Spond J, Chapman R, Fine J, Jones H, Kreutner W, Kung T T, Minnicozzi M. *Comparison of PDE 4 inhibitors, rolipram and SB 207499 (ariflo), in a rat model of pulmonary neutrophilia. Pulm Pharmacol Ther* [2001]; 14 157-164).

The also intensified penetration and the accumulation of monocytes into the inflammatory pulmonary tissue is a typical pathophysiological regulation mechanism in these diseases. The release of pro-inflammatory cytokines, in particular TNFα and GM-CSF and numerous proteolytic enzymes can here be regarded as a guiding phenomenon. Selective PDE-4 inhibitors block the synthesis and release of TNFα, GM-CSF and proteases and stimulate the $PGE_2$ production. Surprisingly, the synthesis of the anti-inflammatory cytokine IL-10 is strongly stimulated by selective PDE-4 inhibitors (Suda Y. Tamura G, Ohno I, Maeda K, Liu Y, Yamauchi K, Kurimoto F, Shirato K. *Effects of phosphodiesterase inhibitors on secretions of human monokines. Allergol Int* [1998]; 47 219-224).

The T-lymphocytes accumulated in the inflammatory pulmonary tissue mainly secret pro-inflammatory cytokines, such as IL-2, IL-4, IL-5, IL-13, TNFα, IFNγ and GM-CSF, whose synthesis is inhibited very effectively by PDE-4 inhibitors.

The B-lymphocytes penetrated in particular in the case of asthma are inhibited by specific PDE-4 inhibitors as regards their IgE synthesis, thus directly influencing the IgE mediated allergic pathogenesis pathway (Coqueret O, Boichot E, Lagente V. *Selective type IV phosphodiesterase inhibitors prevent IL-4-induced IgE production by human peripheral blood mononuclear cells. Clin Exp Allergy [1997]*; 27 816-823).

The epithelial cells of the airways are also strongly involved in the inflammatory reactions in the case of COPD and asthma. When activated, they release a plurality of biologically highly active substances, such as metabolites of arachidonic acid and pro-inflammatory cytokines, such as TNFα and GM-CSF (Chipappara G, Merendino A M, Chimenti L, Rilcobono L, Mirabella F, La Rocca A M, Weck P K, Bonsignore G, Vignola A M. *In vitro and ex vivo effects of the phosphodiesterase 4 inhibitors. Am J Resp Crit Cara Med [2001]*; 163, A278). As a result of a significant synthesis inhibition and release of the pro-inflammatory enzyme MMP-9, PDE-4 inhibitors show in vivo a strong protective effect on epithelial cells of the airways in both animal models and clinical studies (Rabinovici R, Feuerstein G, Abdullah F, Whiteford M, Borboroglu P, Sheikh E, Phillip D R, Ovadia P, Bobroski L, Bagasra O, Neville L F. *Locally produced tumor necrosis factor-alpha mediates interleukin-2-induced lung injury. Circ Res* (1996); 78, 329-236; Ortiz J L, Cortijo J, Valles J M, Bou J, Morcillo E J. *Rolipram inhibits airway microvascular leakage induced by platelet-activating factor, histamine and bradykinin in guinea-pigs. J Pharm Pharmacol* (1993); 45, 1090-1092).

An increased intracellular cAMP level lowers the activity of immunocytes and inflammatory cells both in vitro and in vivo, has a protective effect on epithelial and endothelial cells and conveys a relaxation of the smooth muscle cells in the pulmonary tissue. These pharmacological properties prove effectively the significance of PDE inhibition as a relevant and reliable target for a therapeutic intervention in the case of chronic inflammatory pulmonary diseases, such as COPD and asthma (Barnes P J, Shapiro S D, Pauwels R A. *Chronic obstructive pulmonary disease: molecular and cellular mechanisms. Eur Respir J* (2003); 22, 672-88).

COPD comprises a group of chronic progressive, inflammatory pulmonary diseases, which is predominantly characterized by the migration of neutrophil granuloytes and further immunocompetent cells into the pulmonary tissue. The main symptoms are here chronic cough and expectoration and the companying progressive and irreversible deterioration of the pulmonary function culminating in the maximum variant, i.e. the pulmonary emphysema. The disease proceeds in batches and is often accompanied by bacterial secondary infections of the lung. The most important risk factors are smoking and environmental pollution. As a result of the patients' partially extreme shortness of breath and the small capacity on account of a pulmonary backflow and the resulting cardiac problems, the patients' quality of life and expectancy of life are strongly limited. About 600 million persons suffer from this disease world-wide, and according to WHO it is the sixth most frequent disease world-wide and the fourth most frequent cause of death. With an annual growth rate of 12% (Visiongain, 2004) it will be the third most frequent cause of death globally in the next 20 years. Analysts therefore assume that this disease group represents one of the fastest growing global therapeutic markets. The current standard therapy comprises the administration of $B_2$ agonists, muscarinergic antagonists, corticosteroids and antihistaminics. However, the treatment strategies are only symptomatic but do not interfere causally in the progressive course of the disease. The justified demand existing for years is to causally interfere with the disease process by means of new therapy approaches thus combatting in particular the progressive nature of COPD.

Bronchial asthma is a paroxysmal, non-infectious pulmonary disease usually triggered by allergies, which is predominantly characterized by a migration of eosinophil granulocytes and further immunocompetent cells into the pulmonary tissue and by a temporary bronchoconstriction. A prolonged disease period often results in a chronic bronchitis accompanied by a pulmonary emphysema and bronchiectases culminating in cor pulmonale. The patients' quality of life is considerably limited by the difficult breathing culminating in dyspnea attacks, the considerable secretion of mucus and strong feelings of anxiety. About 5% of the adult population and almost 10% of the children suffer from this disease in the developed countries. A prevalence of 155 million diseased persons with an annual growth rate of 10-15% (from Lead Discovery, 2003) is assumed world-wide. Along with a good therapeutic profile, the standard therapy common for 25 years now and using $B_2$ adenoreceptor agonists (bronchodilation) and corticosteroids (anti-inflammatory) also shows partially considerable undesired side-effects, in particular in childhood (known glucocorticoid side-effects and tachycardia, palpitation, headache in the case of $B_2$ adenoreceptor agonists). This clinical picture also calls for new more active therapy strategies which infere with the disease process not only symptomatically but also causally.

Selective PDE-4 inhibitors should therefore have in combination at least the following in vivo effects:
1. effective inhibition of TNFα synthesis and release in blood cells;
2. significant reduction in the TNFα concentration in the broncho-alveolar lavage fluid (BAL);
3. significant reduction of IL-4 and IL-5 in the BAL fluid;
4. significant inhibition of the migration of eosinophil granulocytes into the lung;
5. significant inhibition of the migration of neutrophil granulocytes into the lung;
6. prevention of "oxidative burst";
7. prevention of bronchoconstriction;
8. prevention of the developing pulmonary edemas (emphysema);
9. prevention of the proliferation and hyperplasia of cells of the airways;
10. Significant inhibition of the MMP-9 activity in the BAL fluid;
11. Significant inhibition of the TGF-β activity in the BAL fluid.

Recent experimental data also prove the promising use of PDE-4 inhibitors as immunomodulatory active substances. The therapeutic potential of PDE-4 inhibitors was proved successfully in animal models for atopic dermatitis (Hanifin J M, Chan S C, Cheng J B, Tofte S J, Henderson W R Jr, Kirby D S, Weiner E S. *Type 4 phosphodiesterase inhibitors have clinical and in vitro anti-inflammatory effects in atopic dermatitis. J Invest Dermatol* (1996); 107, 51-56), rheumatoid arthritis (Laemont K D, Schaefer C J, Juneau P L, Schrier D J. *Effects of the phosphodiesterase inhibitor rolipram on streptococcal cell wall-induced arthritis in rats. Int J Immunopharmacol* (1999); 21, 711-725), ulcerative colitis (Hartmann G, Bidlingmaier C, Siegmund B, Albrich S, Schulze J, Tschoep K, Eigler A, Lehr H A, Endres S. *Specific type IV phosphodiesterase inhibitor rolipram mitigates experimental colitis in mice. J Pharmacol Exp Ther* (2000); 292, 22-30), cystic fibrosis (Dinter H, Onuffer J, Faulds D, Perez H D. *Phosphodiesterase type IV inhibitors in the treatment of multiple sclerosis. J Mol Med* (1997); 75, 95-102), Crohn's disease (Prehn J L, Landers C, Muller G W, Man H W, Stirling D I, Targan S R. *Potent inhibition of cytokine production from intestinal lamina propria T cells by phosphodiesterase-4 inhibitory thalidomide analogues. J Clin Immunol* (2001); 21, 357-364), inflammatory pain (Cunha F Q, Teixeira M M, Ferreira S H. *Pharmacological modulation of secondary mediator systems—cyclic AMP and cyclic GMP—on inflammatory hyperalgesia. Br J Pharmacol* (1999); 127, 671-678), septic shock (Cardelus I, Gras J, Jauregui J, Llenas J, Palacios J M. *Inhibition of lipopolysaccharide-induced bowel erythrocyte extravasation in rats, and of mesenteric hypoperfusion in dogs, by phosphodiesterase inhibitors. Eur J Pharmacol* (1996); 299, 153-159), leishmaniosis (Rascon A. *Cyclic nucleotide phosphodiesterases: diversity, classification, structure and function. Acta Cient Venez* (1997); 48, 145-153) and HIV infections (Sun Y. Li L, Lau F, Beavo J A, Clark E A. *Infection of CD4+ memory T cells by HIV-1 requires expression of phosphodiesterase 4. J Immunol* (2000); 165, 1755-1761).

Clinically, most of the formerly tested PDE-4 inhibitors showed, with rolipram as a guiding structure, undesired drug effects (UDE) and a lacking in vivo effectiveness which have limited their clinical use thus far. Emetic effects, such as nausea and vomiting, but also gastrointestinal complaints, cardiovascular and central side-effects are counted thereamong (Zeller E, Stief H J, Pflug B, Sastre-y-Hernandez M. *Results of a phase II study of the antidepressant effect of rolipram. Pharmacopsychiatry* (1984); 17, 188-190; Puurunen J, Lucke C, Schwabe U. *Effect of the phosphodiesterase inhibitor 4-(3-cyclopentyloxy-4-methoxyphenyl)-2-pyrrolidone (ZK 62711) on gastric secretion and gastric mucosal cyclic AMP. Naunyn Schmiedebergs Arch Pharmacol* (1978); 304, 69-75; Nicholson C D. *Cyclic nucleotide phosphodiesterase isoenzymes and asthma—outstanding issues. Agents Actions Suppl* (1993); 43, 3-12).

Based on rolipram numerous structure-related modifications were then developed which all had a similar side-effect profile (Schneider H H, Schmiechen R. Brezinski M, Seidler J. *Stereospecific binding of the antidepressant rolipram to brain protein structures. Eur J Pharmacol* (1986); 127, 105-115). The PDE-4 inhibitors most widely developed today are cilomilast (Glaxo-SmithKline company) (Compton C H, Gubb J, Nieman R. Edelson J, Amit O, Bakst A, Ayres J G, Creemers J P, Schultze-Werninghaus G, Brambilla C, Barnes N C; *International Study Group. Cilomilast, a selective phosphodiesterase-4 inhibitor for treatment of patients with chronic obstructive pulmonary disease: a randomised, dose-ranging study. Lancet* (2001); 358, 265-270; Compton C, Edelson J D, Cedar E et al. *Cilomilast (Ariflo) 15 mg bid safety in a six month clinical trial program. Am J Resp Crit Care Med* (2001); 163, A909; Zussman B D, Benincosa L J, Webber D M, Clark D J, Cowley H, Kelly J, Murdoch R D, Upward J, Wyld P, Port A, Fuder H. *An overview of the pharmacokinetics of cilomilast (Ariflo), a new, orally active phosphodiesterase 4 inhibitor, in healthy young and elderly volunteers. J Clin Pharmacol* (2001); 41, 950-958; Giembycz M A. *Cilomilast: a second generation phosphodiesterase 4 inhibitor for asthma and chronic obstructive pulmonary disease. Expert Opin Investig Drugs* (2001); 10, 1361-1379) and roflumilast (Altana company) (Schmidt B M, Kusma M, Feuring M, Timmer W E, Neuhauser M, Bethke T, Stuck B A, Hormann K, Wehling M. *The phosphodiesterase 4 inhibitor roflumilast is effective in the treatment of allergic rhinitis. J Allergy Clin Immunol* (2001); 108, 530-536; *SCRIP* 2644, p. 25), which as regards structure have major similarities and obviously a better profile of action with respect to rolipram. As compared to cilomilast, roflumilast which has an $IC_{50}$ value of 0.8 nM is a much more potent PDE-4 inhibitor and also shows a stronger anti-inflammatory activity in numerous in vitro and in vivo investigations (Hatzelmann A, Schudt C. *Anti-inflammatory and immunomodulatory potential of the novel PDE4 inhibitor roflumilast in vitro. J Pharmacol Exp Ther* (2001); 297, 267-79). In spite of the side-effect profile, both active substances successfully passed the clinical study phase III for COPD and asthma but have not yet been approved by the competent authorities.

The formerly developed PDE-4 inhibitors which partially have a comprehensive side-effect profile can basically be divided into the following chemical main classes:
1. Catechol ether compounds having structural similarity with respect to rolipram, cilomilast and roflumilast,
2. Quinazolinediones having structural similarity with respect to nitraquazone,
3. Xanthine derivatives having structural similiarity with respect to theophylline, and
4. Benzofuran derivatives.

Therefore, there is an urgent need to develop novel PDE-4 inhibitors having few side-effects and an improved therapeutic range and introduce them into clinics.

The object of the present invention is thus the provision of novel compounds selectively inhibiting PDE-4.

This object is achieved by the below compounds of general formulae 1a, 1b, 1c and 1d.

Biologically active derivatives of general formula 1b have only been reported in some few cases thus far:

For example, G. Wagner et al.: *Pharmazie* (1993), 48, 667-669, described the synthesis of thienodipyrimidines which have anti-anaphylactic properties. Furthermore, the thienodipyrimidines shown by D. Briel *Pharmazie* (1998), 53, 227-231 were tested for antiulcer activity.

There are also only some reports on biologically active derivatives of general formulae 1c and 1d to date:

For example, S. Leistner et al.: Ger. (East) (1988), DD 258013, described the synthesis of 8,9,10,11-tetrahydropyrimido[4',5':4,5]thieno[2,3-c]isoquinolin-4-ones which have anti-anaphylactic and anti-inflammatory properties. The synthesis of 1,2-dihydro-pyrano[4',3':4,5]pyrido[2,3-b]thieno[3,2-d]pyrimidin-8-ones which have antibacterial properties was described by Paronikyan et al.: U.S.S.R. (1988), SU 85-3914497. Furthermore, pyrido[3',2':4,5]thieno[3,2-d]pyridine-2-carboxylic acids [c]-anellated on the pyridine portion were mentioned by H. Vieweg et al.: Ger. (East) (1988), DD 258018, and by S. Leistner et al.: Ger. (East) (1988), DD 258015, DD 258017 and DD 258019, as regards their potential usability as pharmaceuticals.

There are only a few cases which have reported the biologically active derivatives of general formula 1a thus far:

For example, J. M. Quintela et al.: *Bioorg. Med.* 6 (1998) 1911-1925, described the synthesis of several 2-dimethylamino-(or 2-H)-4-sec.amino-7-ethoxy-8-cyano-(or 8-H)-9-phenyl- and also the structurally analogous 4-ethoxy-pyrido[3',2':4,5]thieno-[3,2-d]pyrimidine derivative. Some of these compounds showed an effect inhibiting the histamine release from mast cells of rats. EP-A-1 323 719 describes thienopyrimidine compounds which have an inhibitory effect on the cGMP specific phosphodiesterase. EP-A-1 277 738 describes pharmaceutical compositions usable as phosphatidylinositol-3-kinase inhibitors and represent condensed heteroaryl derivatives. Abdel-Rahmann et al.: *Pharmazie* 58 (2003) 372-377 reported the synthesis of 8-acetyl-3-amino-7-methyl-4-imino-9-subst.phenyl-pyrido[3',2':4,5]thieno-[3,2-d]-pyrimidines having an antimicrobial effect. Furthermore, derivatives of this heterosystem were described to have inter alia a hypocholesterinemic effect (C. J. Shishoo, M. B. Devani and V. S. Bhadti: Indian Patent 151.456 (1983); *Chem.*

Abstr.: 100, 209858 (1984); and V. P. Arya; *Drugs Future*, 10, 123 (1985)), an analgesic effect (C. G. Dave et al.: *J. Indian Chem. Soc.* 66, 48 (1989)), an antipyretic effect (E. Bousquet et al.: *Farmaco Ed. Sci.* 40, 869 (1985); and E. Bousquet et al.: *Farmaco Ed. Sci.* 39, 110 (1984)), an anti-anaphylactic effect (H. Vieweg, S. Leistner, G. Wagner et al.: Patent DD 257830 (1988); *Chem. Abstr.:* 110, 95262p (1989); and H. Vieweg, S. Leistner, G. Wagner et al.: East German Patent DD 258234 (1988)), an anti-inflammatory effect (E. F. Elslager, P. W. Jacob and M. Leslic: J. *Heterocyclic Chem.* 9, 775 (1972); and M. Chaykovsky et al.: *J. Med. Chem.* 10, 188 (1973); and L. A. Radinovskaya and A. *Sharanin: Khim. Geterotsikl. Soedin.* 805 (1988); and S. Leistner et al.: *Pharmazie* 41, 54 (1986)); a clinically effective anti-allergic effect (G. D. Madding and M. D. Thompson: *J. Heterocyclic Chem.* 24, 581 (1987)) and a potentially anti-neoplastic effect (C. C. Cheng in *Progress in Medicinal Chemistry* 25, 35 (1989).

However, the here described derivatives of general formulae 1a, 1b, 1c and 1d are thus fully unknown as inhibitors of PDE 4 and TNFα release.

BRIEF DESCRIPTION OF THE FIGURE

In FIG. 1a, FIG. 1 shows axons up to a length of 300 μM in N2a cells after 72 h and induction by 1 μM 7-(3,4-dimethoxyphenyl)-4-ethoxy-9-methyl-2-piperazin-1-yl-pyrido[3',2': 4,5]-thieno[3,2-d]pyrimidine hydrochloride und in FIG. 1b it shows the control thereof.

DETAILED DESCRIPTION OF THE INVENTION

Figure 1A:
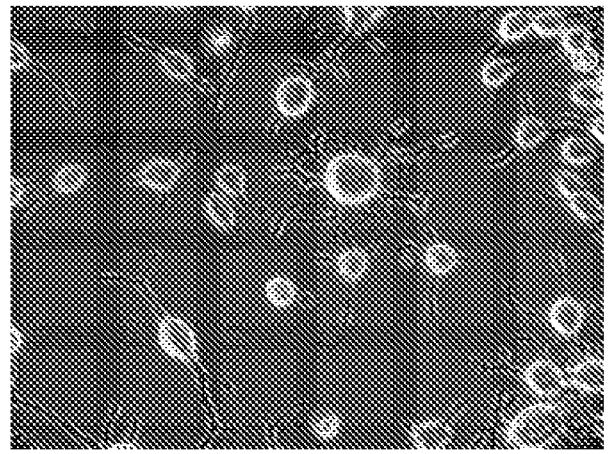

The invention relates to derivatives of general formulae 1a, 1b, 1c and 1d.

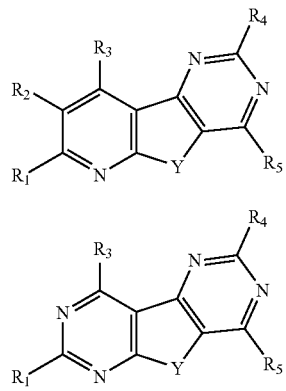

wherein:
Y is S, O or N
$R^1$ is—hydrogen,
  $C_{1-10}$ alkyl, —$C_{2-12}$ alkenyl, —$C_{2-12}$ alkinyl, each straight-chain, branched or cyclic and, where appropriate, substituted singly, doubly or triply with independently selected residues $R^§$,
  aralkyl- having $C_{6-12}$ aryl and $C_{1-5}$ alkyl, substituted, where appropriate, singly, doubly or triply with independently selected residues $R^§$,
  phenyl, substituted, where appropriate, singly, doubly or triply with independently selected residues $R^§$,
  1-naphthyl, 2-naphthyl
  pyridyl-N-oxide, (substituted, where appropriate, with $R^§$),
  monocyclic or bicyclic, saturated or singly or multiply unsaturated heterocycles having 5-14 ring atoms, including 1-4 heteroatoms which are preferably N, O and S, substituted, where appropriate, singly, doubly or triply with independently selected residues $R^§$,
  $C_{1-10}$ alkoxy, straight-chain, branched or cyclic as well as substituted, where appropriate, singly, doubly or triply with independently selected residues $R^§$,
  aralkyloxy- having $C_{6-12}$ aryl and $C_{1-5}$ alkyl, substituted, where appropriate, singly, doubly or triply with independently selected residues $R^§$,
  $C_{2-12}$ alkylacyl (substituted, where appropriate, with $R^§$),
  benzoyl, 1- and 2-naphthoyl (each substituted, where appropriate, with $R^§$),
  hydroxy, sulfhydryl, formyl, carboxyl, $CONH_2$, cyano, rhodano, nitro, $SO_3H$
  alkylthio, alkylsulfinyl, $SO_2OAlk$ and alkylsulfonyl, each straight-chain, branched or cyclic $C_{1-6}$, and substituted, where appropriate, singly, doubly or triply with independently selected residues $R^§$,
  arylthio, arylsulfinyl, arylsulfonyl, heteroarylthio, heteroarylsulfinyl and heteroarylsulfonyl, each substituted, where appropriate, singly, doubly or triply with independently selected residues $R^§$,
  alkoxycarbonyl, CONHAlk and $CONAlk_2$, each straight-chain, branched or cyclic $C_{1-6}$, and substituted, where appropriate, singly, doubly or triply with independently selected residues
  aryloxycarbonyl, arylcarbamoyl, arylamido, N-aryl, N-alkylamido, N-aryl, N-alkylcarbamoyl, aralkyloxycarbonyl and aralkylcarbamoyl, with alkyl $C_{1-5}$, aryl $C_{6-10}$ and substituted, where appropriate, singly, doubly or triply with independently selected residues $R^§$,
  heterocyclylcarbonyl, heterocyclylcarbamoyl, heterocyclylamido, N-heterocyclyl, N-alkylcarbamoyl, N-heterocyclyl, N-alkylamido, heterocyclylalkyloxycarbonyl and heterocyclylalkylcarbamoyl, with a monocyclic or bicyclic, saturated or singly or multiply unsaturated heterocycle having 5-14 ring atoms including 1-4 heteroatoms which are preferably N, O and S, substituted, where appropriate, singly, doubly or triply with independently selected residues $R^§$ and alkyl $C_{1-5}$,
  chlorine, bromine, iodine, fluorine,
  amino, $C_{1-6}$ alkylamino, di($C_{1-5}$)alkylamino, each straight-chain, branched or cyclic and substituted, where appropriate, singly, doubly or triply with independently selected residues $R^§$,
  arylamino $C_{6-10}$, substituted, where appropriate, singly, doubly or triply with independently selected residues $R^§$,
  heterocyclylamino, monocyclic or bicyclic, saturated or singly or multiply unsaturated, having 5-14 ring atoms including 1-4 heteroatoms which are preferably N, O and S, substituted, where appropriate, singly, doubly or triply with independently selected residues $R^§$,
  arylhydrazino, substituted, where appropriate, singly, doubly or triply with independently selected residues $R^§$, $L_A$-A-$L_B$-B wherein:
$L_A$ is—single bond,
  $NR^\#$, O, S, SO, $SO_2$
A is—phenyl, substituted, where appropriate, singly, doubly or triply with independently selected residues $R^§$
  naphthyl, naphthyl substituted singly or multiply with $R^§$ monocyclic or bicyclic, saturated or singly or multiply unsaturated heterocycles having 4-14 ring atoms including 1-5 heteroatoms which are preferably N, O and S which may carry one or more oxygen atoms on C, N and/or S and are substituted, where appropriate, singly, doubly or triply with independently selected residues $R^§$ -$L_A$-A can also be a direct bond tricycle-$L_B$, in this case $L_B$ being a single bond $L_B$ is—single bond $NR^\#$, O, S, SO, $SO_2$, —$CHR^§$—, —$CH_2$—O—, —O—$CH_2$, the following functional groups:

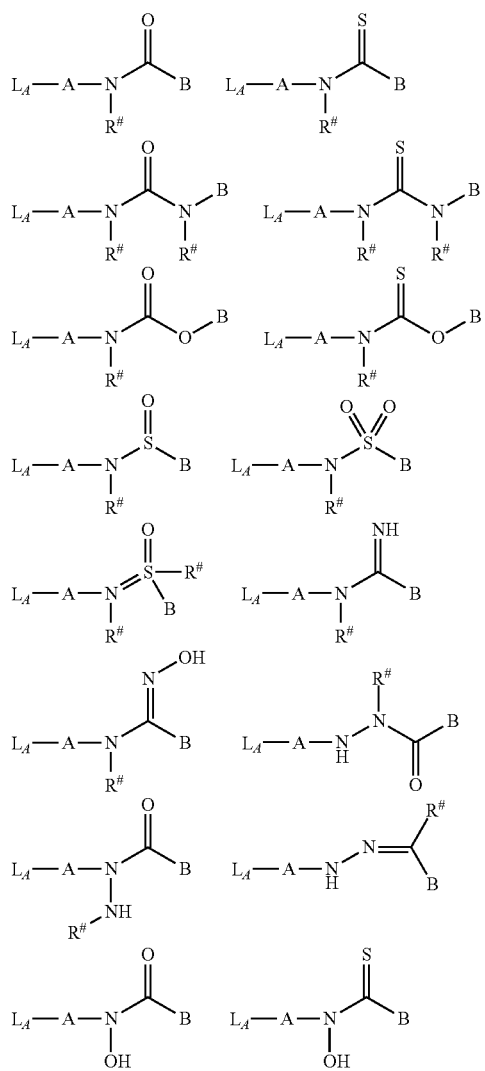

B is—hydrogen alkyl, substituted, where appropriate, singly, doubly or triply independently with $R^§$ —$CONH_2$, —CONHAlk (Alk substituted, where appropriate, with $R^§$), —CONHAryl (aryl substituted, where appropriate, with $R^§$), —CONHHetaryl (hetaryl substituted, where appropriate, with $R^§$), —COOH, —COOAlk (Alk substituted, where appropriate, with $R^§$), —COAlk (Alk substituted, where appropriate, with $R^§$), —COAryl (aryl substituted, where appropriate, with $R^§$), —COHetaryl (hetaryl substituted, where appropriate, with $R^§$)

—$CH_2$—$CONH_2$, —$CH_2$—CONHAlk (Alk substituted, where appropriate, with $R^§$), —$CH_2$—CONHAryl (aryl substituted, where appropriate, with $R^§$), —$CH_2$—CONHHetaryl (hetaryl substituted, where appropriate, with $R^§$), —$CH_2$—COOH, —$CH_2$—COOAlk (Alk substituted, where appropriate, with $R^§$)

—$CH_2$—COAlk (Alk substituted, where appropriate, with $R^§$), —$CH_2$—COAryl (aryl substituted, where appropriate, with $R^§$), —$CH_2$—COHetaryl (hetaryl substituted, where appropriate, with $R^§$)

phenyl, substituted, where appropriate, singly, doubly or triply with independently selected residues $R^§$, naphthyl, substituted, where appropriate, singly, doubly or triply with independently selected residues $R^§$, monocyclic or bicyclic, saturated or singly or multiply unsaturated heterocycles having 4-14 ring atoms including 1-5 heteroatoms which are preferably N, O and S which may carry one or more oxygen atoms on C, N and/or S and may be substituted, where appropriate, singly, doubly or triply with independently selected residues $R^§$, $R^\#$—hydrogen, alkyl, substituted, where appropriate, with $R^§$, $R^2$ is—hydrogen, $C_{1-2}$ alkyl, $C_{2-12}$ alkenyl and $C_{2-12}$ alkinyl, benzyl, phenyl($C_{2-6}$)alkyl (substituted, where appropriate, with $R^§$ once or several times equally or unequally, at the aromatic and/or aliphatic molecule portion);

phenacyl (substituted, where appropriate, with $R^§$ once or several times equally or unequally at the aromatic molecule portion);

carboxyl, $C_{1-4}$ alkoxycarbonyl, —$CONH_2$, —CONHAlk and $CONAlk_2$ ("Alk" each being $C_{1-6}$), $R^\#C(O)$— (wherein $R^\#$ is as defined above), cyano, nitro, amino, $C_{1-6}$ alkylamino, di($C_{1-6}$)alkylamino, —N=N—$C_6H_5$, —N=N—$C_6H_4$—$R^§$, 1,3-diphenyl-pyrazol-4-yl, thiazolin-2-yl, imidazolin-2-yl and 3,4,5,6-tetrahydro-pyrimidinyl;

$R^3$ is—hydrogen, $C_{1-10}$ alkyl, —$C_{2-12}$ alkenyl, —$C_{2-12}$ alkinyl, each straight-chain, branched or cyclic and substituted, where appropriate, singly, doubly or triply with independently selected residues $R^§$, aralkyl- with $C_{6-12}$ aryl and $C_{1-5}$ alkyl, substituted, where appropriate, singly, doubly or triply with independently selected residues $R^§$, phenyl, substituted, where appropriate, singly, doubly or triply with independently selected residues $R^§$, 1-naphthyl, 2-naphthyl pyridyl-N-oxide, (substituted, where appropriate, with $R^§$), $C_{1-10}$ alkoxy, straight-chain, branched or cyclic and substituted, where appropriate, singly, doubly or triply with independently selected residues $R^§$, aralkyloxy- with $C_{6-12}$ aryl and $C_{1-5}$ alkyl, substituted, where appropriate, singly, doubly or triply with independently selected residues $R^§$, $C_{2-12}$ alkylacyl (substituted, where appropriate, with $R^§$), benzoyl, 1- and 2-naphthoyl (each substituted, where appropriate, with $R^§$), hydroxy, sulfhydryl, formyl, carboxyl, $CONH_2$, cyano, rhodano, nitro, $SO_3H$ alkylthio, alkylsulfinyl, $SO_2OAlk$ and alkylsulfonyl, each straight-chain, branched or cyclic $C_{1-6}$ and substituted, where appropriate, singly, doubly or triply with independently selected residues $R^§$, arylthio, arylsulfinyl, arylsulfonyl, heteroarylthio, heteroarylsulfinyl and heteroarylsulfonyl, each substituted, where appropriate, singly, doubly or triply with independently selected residues $R^§$, alkoxycarbonyl, $CONHAlk$ and $CONAlk_2$, each straight-chain, branched or cyclic $C_{1-6}$, and substituted, where appropriate, singly, doubly or triply with independently selected residues $R^§$, aryloxycarbonyl, arylcarbamoyl, arylamido, N-aryl, N-alkylamido, N-aryl, N-alkylcarbamoyl, aralkyloxycarbonyl and aralkylcarbamoyl, with alkyl $C_{1-5}$, aryl $C_{6-10}$ and substituted, where appropriate, singly, doubly or triply with independently selected residues $R^§$, chlorine, bromine, iodine, fluorine, amino, $C_{1-6}$ alkylamino, $di(C_{1-5})$alkylamino, each straight-chain, branched or cyclic and substituted, where appropriate, singly, doubly or triply with independently selected residues arylamino $C_{6-10}$, substituted, where appropriate, singly, doubly or triply with independently selected residues $R^§$, arylhydrazino, substituted, where appropriate, singly, doubly or triply with independently selected residues $R^§$, $R^4$ is —$C_{2-14}$ alkyl, $C_{3-14}$ cycloalkyl, $C_{2-14}$ alkenyl, $C_{3-14}$ cycloalkenyl, $C_{2-14}$ alkinyl (each substituted, where appropriate, on the C-skeleton of the above mentioned aliphatic residues with $R^§$);

phenyl, 4-$R^§$-phenyl, 3-$R^§$-phenyl, 2-$R^§$-phenyl (with the exception of: 2-$NO_2$-phenyl), 3-$R^§$, 4-$R^§$-phenyl, 3-$R^§$, 4-$R^§$-, 5-$R^§$-phenyl, 1-naphthyl, 2-naphthyl (each substituted, where appropriate, with $R^§$);

S-alkyl, SO-alkyl, $SO_2$-alkyl, (each $C_1$-$C_8$),

S-alkenyl, SO-alkenyl, $SO_2$-alkenyl (each $C_2$-$C_8$)

S-alkinyl, SO-alkinyl, $SO_2$-alkinyl (each $C_2$-$C_6$)

(each substituted, where appropriate, on the C-skeleton of the above mentioned aliphatic residues with —OH, —CN, —SCN, —$NO_2$, phenyl or $C_3$-$C_7$ cycloalkyl);

monocyclic, bicyclic or tricyclic, saturated or singly or multiply unsaturated heterocyclic residue having a total of 4-14 ring atoms including 1-5 heteroatoms which are preferably N, O, S and Se (each substituted, where appropriate, with $R^§$);

$OR^6$, wherein $R^6$ is $CH_3$, $C_2H_5$, $(CH_2)_2CH_3$, $(CH_2)_3CH_3$, $C(CH_3)_3$, $CH_2CH_2OH$, $CH_2CH_2SH$, $CH_2CH_2SCH_3$, $CH_2CF_3$, $CH_2CCl_3$, $CH_2CHF_2$, $CH_2CHCl_2$, $CH_2CH_2F$, $CH_2CH_2Cl$, $CH_2CH_2Br$, $C_{3-7}$ cycloalkyl [e.g. cyclopropyl, cyclopropylmethyl, cyclobutyl, cyclobutylmethyl, cyclopentyl, cyclopentylmethyl, cyclohexyl, cyclohexylmethyl] (substituted, where appropriate, on the C-skeleton with $R^§$), $C_{2-5}$ alkenyl and $C_{2-5}$ alkinyl, $C_{3-7}$ cycloalkenyl, aryl and heteroaryl as residues of monocyclic, bicyclic or tricyclic aromatic compounds or heteroaromatic compounds with 6-14 ring atoms, where appropriate [e.g. phenyl, 4-$R^§$-phenyl, 3-$R^§$-phenyl, 2-$R^§$-phenyl, 3-$R^§$, 4-$R^§$-phenyl, 3-$R^§$, 4-$R^§$-, 5-$R^§$-phenyl]

1-naphthyl, 2-naphthyl (each substituted, where appropriate, with $R^§$), pyridyl, isoquinolinyl, quinolinyl, acridinyl;

$NR^7R^8$ wherein this substituent is altogether:

morpholino, thiomorpholino, thiomorpholino-S,S-dioxide, pyrrolidino, piperidino, 1-piperazino, 1-homopiperazino, 4-$C_{1-6}$-alkyl-1-piperazino, 4-(2-hydroxyethyl)-1-piperazino, 4-benzyl-1-piperazino, 4-aryl-1-piperazino (substituted, where appropriate, with $R^§$ on the heterocycloaliphatic ring), further amino residues of secondary, monocyclic or polycyclic cycloaliphatic amines, having a total of 5-14 ring atoms, including the representatives substituted with $R^§$ on the C-skeleton;

amino residues of secondary aliphatic and aromatic amines, $R^7$, $R^8NH$, wherein $R^7$ and $R^8$ may independently be equal or unequal and represent:

$C_{1-6}$ alkyl, benzyl, phenyl, 1- and 2-naphthyl, 2-, 3- and 4-pyridyl, quinolinyl, isoquinolinyl, 2-thienyl, 2-furyl (each substituted, where appropriate, with $R^§$);

amino residues of primary amines, $R^7NH_2$, (wherein $R^7$ is the same as above), amino, $NH_2$, with the limitation that in this case $R^5$ only has the meaning of $OR^6$;

$R^5$ is —$OR^6$, wherein $R^6$ is as defined above, $NR^7R^8$, which is as defined above but with the limitation that $R^4$ does not have the meaning of $NR^7R^8$, and with the exception of morpholino when $R^4$=aryl, azido, hydroxylamino, O—$(C_{1-3})$alkylhydroxylamino, N—$(C_{1-3})$alkylhydroxylamino, N,N-di$(C_{1-3})$alkylhydroxylamino, hydrazino, $(C_{1-4})$alkyl- and di$(C_{1-4})$alkylhydrazino, benzylhydrazino, acylhydrazino, N,N-diacylhydrazino, carbamoylamino, 1-imidazolyl, 1,2,4-triazol-lyl, 1-pyridinium, 1-pyrazinium, 1-pyridazinium, including the alkylsubstituted representatives of these azaheterocycles;

$R^§$ is —OH, —SH, —O—$C_{1-8}$ alkyl, —O—$C_{6-14}$ aryl, —S—$C_{1-4}$ alkyl, —S—$C_{6-14}$ aryl, —SO—$C_{1-4}$ alkyl, —SO—$C_{6-14}$ aryl, —$SO_2$—$C_{1-4}$ alkyl, —$SO_2$—$C_{6-14}$ aryl, —$SO_3H$, —$OSO_2C_{1-8}$ alkyl, —$OSO_2C_{6-14}$ aryl, —COOH, —$COOC_{1-8}$ alkyl, —(CO)$C_{1-8}$ alkyl, —COOH, —$CONH_2$, —$CONHC_{1-6}$ alkyl, —$CON(C_{1-6}$ alkyl)$_2$, —$NH_2$, —$NHC_{1-6}$ alkyl, —$N(C_{1-6}$ alkyl)$_2$, —$NHC_{6-14}$ aryl, —NH-hetaryl, —$N(C_{6-14}$ aryl)$_2$, —$N(C_{1-6}$ alkyl)$(C_{6-14}$ aryl), $C_{1-6}$ alkyl, —$C_{2-12}$ alkenyl, —$C_{2-12}$ alkinyl, each straight-chain, branched or cyclic and independently substituted, where appropriate, singly, doubly or triply with halogen, halogen (F, —Cl, —Br, —I),

—$CH_2CH_2OH$, —$CH_2CH_2SH$, —$CH_2CH_2SCH_3$, sulfamoyl, alkylsulfamoyl, dialkylsulfamoyl with alkyl $C_{1-5}$ substituted, where appropriate, with methoxy, amidino, hydroxyamidino sulfo, phosphono, —CN, —$NO_2$, and —SCN The following compound of formula 1(a) is not protected: Y=S, $R^1$=$OC_2H_5$, $R^2$=CN, $R^3$=$C_6H_5$, $R^4$=$N(CH_3)_2$, $R^5$=$OC_2H_5$

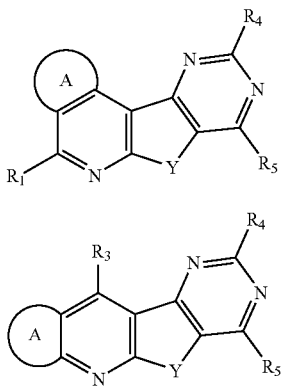

Y is—sulfur, nitrogen or oxygen,

A is—anellated carbocycle having 5 to 8 ring atoms, singly or multiply unsaturated and aromatic (substituted, where appropriate, with R* and/or substituted, where appropriate, with $R^§$);

anellated bicycle having 6 to 11 ring atoms, singly or multiply unsaturated, which may also contain nitrogen, oxygen and/or sulfur (substituted, where appropriate, with R* and/or substituted, where appropriate, with $R^§$);

annelated heterocycle having 5 to 8 ring atoms, singly or multiply unsaturated and aromatic, which may independently contain nitrogen, oxygen and sulfur singly, multiply, equally or unequally in the cycle (substituted, where appropriate, with R* and/or substituted, where appropriate, with $R^§$), $R^1$ and $R^3$ are hydrogen (except when A is an anellated unsubstituted cyclopentene ring combined with $R^4$, $R^5$ equals —OH)

$C_{1-10}$ alkyl (substituted, where appropriate, with $R^§$), $C_{2-12}$ alkenyl and $C_{2-12}$ alkinyl (each substituted, where appropriate, with $R^§$), difluoromethyl, trifluoromethyl, benzyl, phenyl-($C_{2-6}$)alkyl (each substituted, where appropriate, with $R^§$), phenyl (substituted, where appropriate, with $R^§$), in particular: 4-$R^§$-phenyl, 3-$R^§$-phenyl, 2-$R^§$-phenyl, 3-$R^§$, 4-$R^§$-phenyl, 3-$R^§$, 4-$R^§$-, 5-$R^§$-phenyl, 2-$R^§$, 4-$R^§$-phenyl, 1-naphthyl, 2-naphthyl (each substituted, where appropriate, with $R^§$), $C_{3-14}$ cycloalkyl, $C_{3-14}$ cycloalkenyl (each substituted, where appropriate, with $R^§$), monocyclic or bicyclic, saturated or singly or multiply unsaturated heterocycles having 4-14 ring atoms including 1-5 heteroatoms which are preferably N, O and S which may carry one or more oxygen atoms on C, N and/or S and, where appropriate, can be substituted singly, doubly or triply with independently selected residues $R^§$, $C_{2-12}$ alkylacyl (substituted, where appropriate, with $R^§$), benzoyl, 1- and 2-naphthoyl (each substituted, where appropriate, with $R^§$), heterocyclylacyl [e.g. nicotinoyl, isonicotinoyl, 2-picolinoyl, 2-thienoyl, 2-furoyl] (substituted, where appropriate, with $R^§$)

hydroxy, sulfhydryl, $C_{1-10}$ alkoxy, alkylthio, alkylsulfinyl and alkylsulfonyl (each $C_{1-6}$)

formyl, carboxyl, $C_{1-4}$ alkoxycarbonyl;

$CONH_2$, CONHAlk and $CONAlk_2$ (with "Alk" each $C_{1-6}$), cyano, rhodano, nitro, $SO_3H$, $SO_2OAlk$ (with "Alk": $C_{1-5}$), chlorine, bromine, iodine, fluorine, amino, $C_{1-6}$ alkylamino, di($C_{1-5}$)alkylamino (each substituted, where appropriate, with $R^§$ on the alkyl residue), morpholino, thiomorpholino, thiomorpholino-5-oxide, thiomorpholino-S,S-dioxide, pyrrolidino, piperidino, 1-piperazino, 4-methyl-1-piperazino, 4-hydroxyethyl-1-piperazino, 4-phenyl-1-piperazino, cycloalkylamino, $C_{3-14}$ arylamino and heteroarylamino [e.g. phenyl-, 1- and 2-naphthyl-, 2-, 3- or 4-pyridyl-, quinolinyl-, isoquinolinyl-, acridinyl-, phenothiazinyl-, 2-thienyl- and 2-furylamino] (each substituted, where appropriate, on the carbocyclic and/or heterocyclic rings with $R^§$);

$R^4$ is —$C_{2-14}$ alkyl, $C_{3-14}$ cycloalkyl, $C_{2-14}$ alkenyl, $C_{3-14}$ cycloalkenyl, $C_{2-14}$ alkinyl (each substituted, where appropriate, with $R^§$ on the C-skeleton of the above mentioned residues);

benzyl, phenyl-($C_{2-6}$)alkyl (each substituted, where appropriate, with $R^§$), phenyl (substituted, where appropriate, with $R^§$), in particular:

4-$R^§$-phenyl, 3-$R^§$-phenyl, 2-$R^§$-phenyl, 3-$R^§$, 4-$R^§$-phenyl, 3-$R^§$, 4-$R^§$-, 5-$R^§$-phenyl, 2-$R^§$, 4-$R^§$-phenyl, 1-naphthyl, 2-naphthyl (each substituted, where appropriate, with $R^§$);

S-alkyl ($C_3$-$C_8$), SO-alkyl, $SO_2$-alkyl, (each $C_1$-$C_8$),

S-alkenyl, SO-alkenyl, $SO_2$-alkenyl (each $C_2$-$C_8$)

S-alkinyl, SO-alkinyl, $SO_2$-alkinyl (each $C_2$-$C_6$)

(each substituted, where appropriate, with —OH, —CN, —SCN, —$NO_2$, phenyl or $C_3$-$C_7$ cycloalkyl on the C-skeleton of the above-mentioned residues);

monocyclic, bicyclic or tricyclic, saturated or singly or multiply unsaturated heterocyclic residue having a total of 4-14 ring atoms including 1-5 heteroatoms which are preferably N, O, S and Se (each substituted, where appropriate, with $R^§$);

$OR^6$, wherein $R^6$ is hydrogen $CH_3$, $C_2H_5$, $(CH_2)_2CH_3$, $(CH_2)_3CH_3$, $CH(CH_3)_2$, $CH_2CH(CH_3)_2$, $C(CH_3)_3$, $CH_2CH_2OH$, $CH_2CH_2SH$, $CH_2CH_2SCH_3$, $CH_2CF_3$, $CH_2CCl_3$, $CH_2CHF_2$, $CH_2CHCl_2$, $CH_2CH_2F$, $CH_2CH_2Cl$, $CH_2CH_2Br$, $C_{3-7}$ cycloalkyl [e.g. cyclopropyl, cyclopropylmethyl, cyclobutyl, cyclobutylmethyl, cyclopentyl, cyclopentylmethyl, cyclohexyl, cyclohexylmethyl] (substituted, where appropriate, with $R^§$ on the C-skeleton), $C_{2-5}$ alkenyl and $C_{2-5}$ alkinyl, $C_{3-7}$ cycloalkenyl, aryl and heteroaryl as residues of monocyclic, bicyclic or tricyclic aromatic compounds or heteroaromatic compounds with optionally 6-14 ring atoms [e.g. phenyl, 4-$R^§$-phenyl, 3-$R^§$-phenyl, 2-$R^§$-phenyl, 3-$R^§$, 4-$R^§$-phenyl, 3-$R^§$, 4-$R^§$-, 5-$R^§$-phenyl]

1-naphthyl, 2-naphthyl (each substituted, where appropriate, with $R^§$), pyridyl, isoquinolinyl, quinolinyl, acridinyl;

$NR^7R^8$, wherein this substitutent is altogether:

morpholino, thiomorpholino, thiomorpholino-5-oxide, thiomorpholino-S,S-dioxide, pyrrolidino, piperidino, 1-piperazino, 1-homopiperazino, 4-$C_{1-6}$ alkyl-1-piperazino, 4-(2-hydroxyethyl)-1-piperazino, 4-benzyl-1-piperazino, 4-aryl-1-piperazino (each substituted, where appropriate, with $R^§$ on the heterocycloaliphatic ring), further amino residues of secondary, monocyclic or polycyclic cycloaliphatic amines having a total of 5-14 ring atoms, including the representatives substituted with $R^§$ on the C-skeleton;

amino residues of secondary aliphatic and aromatic amines, $R^7$, $R^8$H, wherein $R^7$ and $R^8$ may be independently equal or unequal and represent:

$C_{1-6}$ alkyl, benzyl, phenyl, 1- and 2-naphthyl, 2-, 3- and 4-pyridyl, quinolinyl, isoquinolinyl, 2-thienyl, 2-furyl (each substituted, where appropriate, with $R^§$);

amino residues of primary amines, $R^7NH_2$, (wherein $R^7$ is as defined above), amino, $NH_2$, with the limitation that in this case $R^5$ only has the meaning of —$OR^6$;

$R^5$ is—hydrogen, heterocyclyl, five-membered to seven-membered, substituted, where appropriate, by $R^3$, phenyl, substituted, where appropriate, by $R^3$, $OR^6$, wherein $R^6$ is as defined above, $NR^7$, $R^8$, with the same meaning as above azido, hydroxylamino, O—($C_{1-3}$)alkylhydroxylamino, N—($C_{1-3}$)alkylhydroxylamino, N,N-di($C_{1-3}$)alkylhydroxylamino, hydrazino, ($C_{1-4}$)alkyl- and di($C_{1-4}$)alkylhydrazino, benzylhydrazino, acylhydrazino, N,N-diacylhydrazino, carbamoylamino, 1-imidazolyl, 1,2,4-triazol-lyl, 1-pyridinium, 1-pyrazinium, 1-pyridazinium, including the alkyl-substituted representatives of these azaheterocycles;

$R^*$ =O, =S, =N—H, =N—$C_{1-8}$ alkyl, =N-aryl, =N—OH, =N—O—$C_{1-8}$ alkyl,

=N—O—$C_{6-14}$ aryl $R^§$ as defined above (in formula 1a or 1b)

wherein the following compounds of formula 1(c) are not protected:

1,4-dihydro-2,2-dimethyl-5-(4-morpholinyl)-10-propylthio-2H-pyrano[4'',3'':4',5']pyrido[3',2':4',5']thieno[3,2-d]pyrimidin-8(9H)-one, 10-buthylthio-1,4-dihydro-2,2-dimethyl-5-(4-morpholinyl)-2H-pyrano[4'',3'':4',5']pyrido[3',2':4',5'] thieno[3,2-d]pyrimidin-8(9H)-one and 2-methyl-5-thiophen-2-yl-1,2,3,4-tetrahydro-11H-7-thia-2,6,9,1-tetraaza-benzo[c]fluorene-8,10-dione and pharmaceutically compatible salts, solvates, active metabolites, tautomers and prodrugs of these compounds.

The above-mentioned expression "substituted, where appropriate, with $R^§$" means that said residues can independently be substituted singly, doubly or multiply, equally or unequally, wherein $R^§$ has the following meaning:

—OH, —SH, —O—$C_{1-8}$ alkyl, —O—$C_{6-14}$ aryl, —S—$C_{1-4}$ alkyl, —S—$C_{6-14}$ aryl, —SO—$C_{1-4}$ alkyl, —SO—$C_{6-14}$ aryl, —$SO_2$—$C_{1-4}$ alkyl, —$SO_2$—$C_{6-14}$ aryl, —$SO_3$H, —$OSO_2C_{1-8}$ alkyl, —$OSO_2C_{6-14}$ aryl, —COOH, —$COOC_{1-8}$ alkyl, —(CO)$C_{1-8}$ alkyl, —COOH, —$COOC_{1\ldots8}$ alkyl, —$CONH_2$, —$CONHC_{1-6}$ alkyl, —CON($C_{1-6}$ alkyl)$_2$, —$NH_2$, —$NHC_{1-6}$Alkyl, —N($C_{1-6}$ alkyl)$_2$, —$NHC_{6-14}$ aryl, —NH— hetaryl, —N($C_{6-14}$ aryl)$_2$, —N($C_{1-6}$ alkyl)($C_{6-14}$ aryl), —$CH_3$, —$CHF_2$, —$CF_3$, —$C_2H_5$, —C($CH_3$)$_2$, —($CH_2$)$_2$ $CH_3$, —($CH_2$)$_3CH_3$, —$CH_2CH_2OH$, —$CH_2CH_2SH$, —$CH_2CH_2SCH_3$, —$CH_2CF_3$, —$CH_2CCl_3$, —$CH_2CHF_2$, —$CH_2CHCl_2$, —$CH_2CH_2F$, —$CH_2CH_2Cl$, —$CH_2CH_2Br$, -cyclopropyl, -cyclopropylmethyl, -cyclobutyl, -cyclobutylmethyl, -cyclopentyl, -cyclopentylmethyl, -cyclohexyl, -cyclohexylmethyl, —F, —Cl, —Br, —I, —CN, —$NO_2$, and —SCN.

The above-mentioned expression "substituted, where appropriate, with $R^*$" means that said residues may independently be substituted singly or multiply, equally or unequally, wherein $R^*$ has the following meaning:

=O, =S, =N—H, =N—$C_{1-8}$ alkyl, =N-aryl, =N—OH, =N—O—$C_{1-8}$ alkyl, =N—O—$C_{6-14}$ aryl The terms "alkyl, alkenyl, alkinyl, alkoxy, etc.", also in word combinations such as alkylsulfonyl, alkylamino or alkoxycarbonyl etc., mean both un-branched and branched possible compounds. Likewise "alkenyl and alkinyl" refer to the correspondingly possible singly or multiply saturated compounds. The same also applies to corresponding cyclic compounds.

Of the compounds of general formula 1a the compounds of general formula 1a (I) and 1a (II) have to be emphasized as special embodiment of the invention,

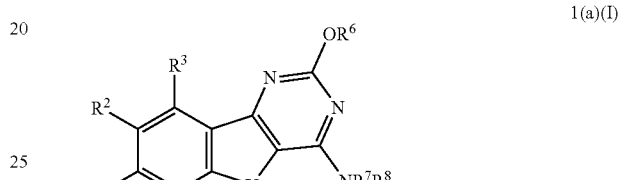

1(a)(I)

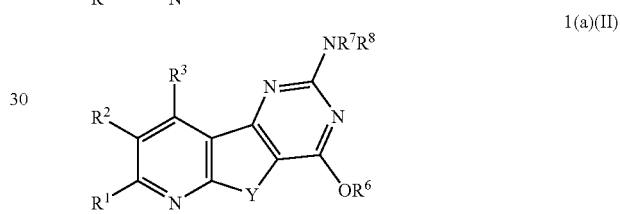

1(a)(II)

wherein $R^1$, $R^2$, $R^3$, $R^6$, $R^7$, $R^8$ and Y have the meanings mentioned above with respect to formula 1(a).

Of the compounds of general formula 1c the compounds of general formula 1c (I) and 1c (II) have to be emphasized as special embodiment of the invention,

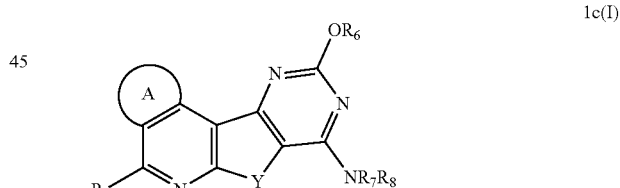

1c(I)

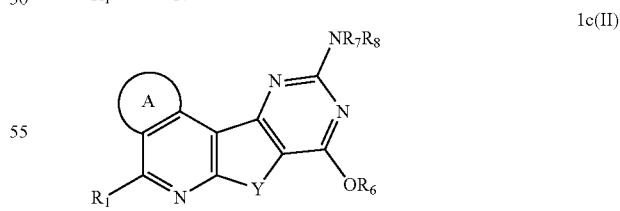

1c(II)

wherein $R^1$, $R^6$, $R^7$, $R^8$ as well as A and Y have the meanings mentioned above with respect to formula 1c.

Within the meaning of the invention, all residues are considered combinable unless stated otherwise in the definition of the residues. All conceivable subgroupings thereof shall be considered disclosed.

The invention also relates to physiologically compatible salts of the compounds of general formulae 1a, 1b, 1c and 1d.

The physiologically compatible salts are obtained as usual by reaction of basic compounds of general formulae 1a, 1b, 1c and 1d with inorganic or organic acids, optionally also in the presence of compounds having acidic properties, e.g. when one of the substituents $R_1$, $R_2$, $R_3$, $R_4$ or $R_5$ is —COOH or —$SO_3H$ in these compounds, by neutralization with inorganic or organic bases.

The inorganic acids used are preferably hydrochloric acid, sulfuric acid, nitric acid or hydrobromic acid, the organic acids used are e.g. formic acid, acetic acid, propionic acid, glycolic acid, lactic acid, amygdalic acid, tartaric acid, malic acid, citric acid, malonic acid, maleic acid, fumaric acid, succinic acid, alginic acid, benzoic acid, 2-, 3- and 4-alkyloxy- and acyloxy-benzoic acids, ascorbic acid, $C_1$-$C_3$ alkylsulfonic acids, benzenesulfonic acid, nicotinic acid, isonicotinic acid and amino acids.

The inorganic bases used are e.g. ammonia, caustic soda solution and potassium hydroxide solution and the employed organic bases are alkylamines, $C_1$-$C_3$, pyridine, quinoline, isoquinoline, piperazine and derivatives thereof, picolines, quinaldine or pyrimidine.

Furthermore, physiologically compatible salts of the compounds according to general formulae 1a, 1b, 1c and 1d can be obtained by converting the substances which as substituents have a tertiary amino group, in a way known in principle with alkylating agents—such as alkyl or aralkyl halides—into the corresponding quaternary ammonium salts.

The invention also relates to solvates of the compounds, including the pharmaceutically acceptable salts, acids, bases and esters as well as the active metabolites thereof and optionally their tautomers according to general formulae 1a, 1b, 1c and 1d including prodrug formulations. Prodrug formulations here comprise all substances forming by simple transformation including hydrolysis, oxidation or reduction either enzymatically, metabolically or in another way. A suitable prodrug e.g. contains a substance of general formulae 1a, b, c or d, which is bound to a solution-improving substance (e.g. tetraethylene glycol, saccharides, amino acids) via an enzymatically cleavable linker (e.g. carbamate, phosphate, N-glycoside or a disulfide group. A patient can be given such a prodrug of a compound according to the invention by injection, and this prodrug can be transformed into a substance of general formulae 1a, b, c or d so as to obtain the desired pharmacological effect.

The diseases which can be treated by the compounds according to the invention include all diseases where the enzyme phosphodiesterase (PDE-4) plays a part, e.g. bronchial asthma, COPD, rheumatoid arthritis (RA), osteoarthritis, cystic fibrosis, Guillain-Barré syndrome, Crohn's disease, ulcerative colitis, psoriasis, atopic dermatitis, allergic eczemas, allergic rhinitis, allergic conjunctivitis, systemic scleroderma, graft versus host disease (GvHD), systemic lupus erythematosus (SLE), diabetes mellitus type I, neurodegenerative diseases, in particular Alzheimer's disease and Parkinson's disease, post-traumatic multiorgan failure, toxic shock syndrome, acute glomerulonephritis, acute and chronic pains, arteriosclerosis, cardiac infarction, apoplexy, tumoral diseases, and here in particular tumors of the blood-forming system, such as leukemias (in particular CLL) and lymphomas, axonal degeneration, viral diseases, and here in particular retroviral diseases, such as the acquired immunodeficiency syndrome (AIDS) and myastenia gravis.

The diseases which can be treated by the compounds according to the invention also include those occurring in veterinary medicine, in particular bronchial asthma, COPD and dermatitides of different genesis.

The compounds according to the invention can be administered in various ways, e.g. orally, parenterally, cutaneously, subcutaneously, intravenously, intramuscularly, rectally or inhalationally. The oral or inhalational administration is preferred. The compound is given to a patient who is in need of a therapy of a disease coming under the indication spectrum of the compounds according to the invention over a period to be determined by a physician. The compound can be administered to both humans and other mammals.

The dosage of the compounds according to the invention is determined by the physician by means of the patient-specific parameters, such as age, weight, sex, severity of the disease, etc. The dosage is preferably between 0.001 mg/kg and 1000 mg/kg body weight, more preferably 0.01 and 500 mg/kg body weight and most preferably 0.1 and 100 mg/kg body weight.

In accordance with the kind of administration, the medicament is formulated suitably, e.g. as solutions or suspensions, simple tablets or dragees, hard or soft gelatin capsules, powder for reconstitution prior to use, aerosols, inhalation sprays, active substance plasters, granules, suppositories, ovules, injectables, creams, ointments, gels, microspheres, implants, which are produced according to conventional galenic processes.

The compounds according to the invention can optionally be formulated with further active substances and with excipients common in pharmaceutical compositions, depending on the preparation to be produced e.g. talcum, gum arabic, lactose, starch, magnesium stearate, cacao butter, aqueous and non-aqueous carriers, adipoids of animal or vegetable origin, paraffin derivatives, glycols (in particular polyethylene glycol), various plasticizers, dispersants or emulsifiers, pharmaceutically compatible gases (e.g. air, oxygen, carbon dioxide, etc.), preservatives.

Additives, such as sodium chloride solution, ethanol, sorbitol, glycerol, olive oil, almond oil, propylene glycol, ethylene glycol or other additives common in pharmacy, can be used for the production of liquid preparations.

When infusion or injectable solutions are used, these are preferably aqueous solutions or suspensions, which can be produced prior to use, e.g. from lyophilized preparations which contain the active substance as such or together with a carrier, such as mannitol, lactose, glucose, albumin and the like. The ready-to-use solutions are sterilized and, if required, mixed with excipients, e.g. preservatives, stabilizers, emulsifiers, solubilizers, buffers and/or salts for regulating the osmotic pressure. The sterilization can be obtained by sterile filtration through filters having a small pore size whereupon the composition may be lyophilized, where necessary. Small amounts of antibiotics can also be added to maintain sterility.

Inhalation compositions, e.g. in the form of aerosols, sprays or as a micronized powder, are also produced preferably. For this purpose, the compounds according to the invention are either dissolved or suspended in pharmaceutically common solvents and finely divided and inhaled by means of excess pressure in a certain volume. A corresponding approach is made with the solid substances to be inhaled which are also finely divided and inhaled by means of excess pressure. Applicators functioning with other than excess pressure are also included herein.

The invention also relates to pharmaceutical preparations containing a therapeutically active amount of the active ingredient (compound of formulae 1a, 1b, 1c or 1d according to the invention) together with organic or inorganic solid or liquid pharmaceutically compatible carriers which are suited for the intended administration and which do not unfavourably interact with the active ingredients.

The invention also relates to processes for the production of pharmaceutical preparations, which are characterized in that the compound according to the invention is mixed with a pharmaceutically compatible carrier.

Based on combination therapies with already known active substances, the compounds according to the invention are also suited for treating the above-mentioned diseases. Here, surprising synergistic effects for increasing the therapeutic effectivenees of the substances according to the invention shall be utilized. On the one hand, the combination can consist of offering a single pharmaceutical composition which contains at least one of the compounds according to the invention in combination with one or more of the below active substances or the patient is given several preparations containing one or more of the below active substances simultaneously with, or time-staggered with respect to, the pharmaceutical composition according to the invention.

It is preferred to combine one or more of the compounds according to the invention with one or more of the following active substances:

- $\beta_2$ adrenoceptor agonists (e.g. terbutaline, salbutanol, salmetanol, fenoterol, formoterol)
- disodium cromoglycate
- corticosteroids
- leukotriene antagonists (either enzyme inhibitors [such as 5-lipoxygenase inhibitors or arachidonic acid enzyme inhibitors] or receptor antagonists), e.g. pramkulast, montelukast, zafirlukast, zileuton
- antihistaminic drugs (preferably those having mast cell-stabilizing properties or leukotriene-antagonizing aspects, such as loratadine, astemizole, mizolastine, olopatadine
- theophylline
- muscarine receptor antagonists, e.g. spiriva
- (monoclonal) antibodies against TNF-alpha or other active substances which inhibit the formation or release of TNF-alpha or the activity of TNF-alpha (e.g. recombinant soluble receptor constructs)

The combination with corticosteroids, leukotriene antagonists, antihistaminic drugs, theophyline, muscarine receptor antagonists and/or TNF-alpha inhibitors serves in particular the purpose of not rendering the acute disease condition to be treated chronic since the compounds according to the invention and the other active substances counteract complementary aspects of the pathophysiological mechanisms underlying the disease. According to the invention, in particular the combination of the compounds according to the invention with $B_2$ adrenoceptor agonists and/or disodium cromoglycate should be effective as inhalation therapy in mild forms of asthma, in particular in childhood. In combination with glucocorticoids a positive effect is a result of the circumstance that fewer glucocorticoids have to be used so as to achieve a savings effect and reduce, or even prevent, the side-effects known for glucocorticoids. The combination of the compounds according to the invention with glucocorticoids and/or theophylline has proved to be useful in particular in the case of persistent asthma.

Depending on the severity of the disease and the underlying symptoms the compounds according to the invention can be present with respect to the other active substances in the combination at a ratio of 1:10.000 to 10.000:1, preferably 1:100 to 100:1, most preferably 1:10 to 10:1.

The invention also relates to processes for the production of the compounds according to the invention.

The processes according to the invention for the production of the compounds of general formulae 1a, 1b, 1c and 1d with the above mentioned meanings of $R_1$, $R_2$, $R_3$, $R_4$, $R_5$ and Y are characterized by the following methods:

according to scheme 1

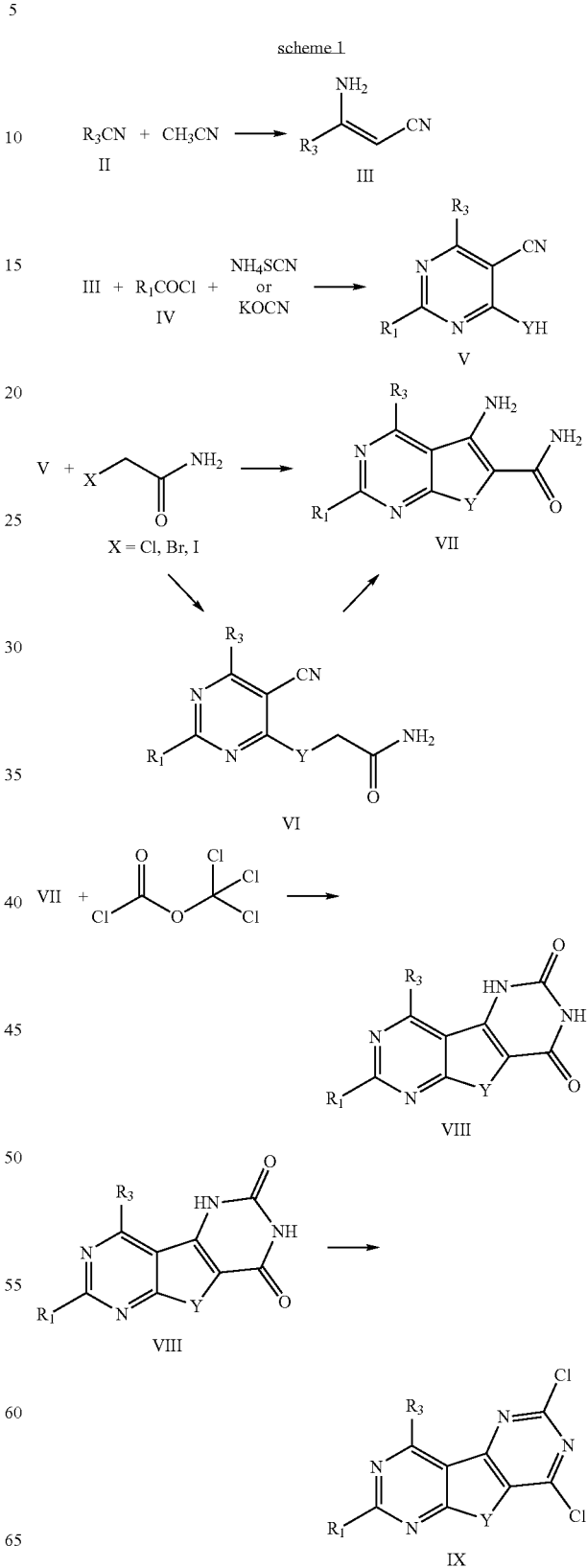

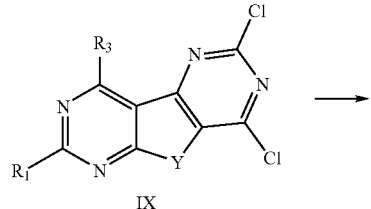

IX

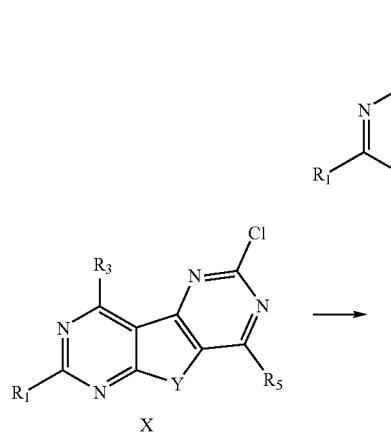

X

X

Ib

Preparation of 2-aminonitrile of general formula III by reacting acetonitrile with a nitrile of general formula II (with identical meaning of $R_3$) in the presence of an alkoxide, preferably potassium-tert-butoxide in a suitable solvent, preferably toluene.

Reaction of an acide halide of general formula IV (with identical meaning of $R_1$) with a thiocyanate for Y=S or cyanate for Y=O, preferably ammonium thiocyanate or potassium cyanate, in a suitable solvent, preferably dioxane, to give carboxylic acid isothiocyanate or -isocyanate which is reacted with a 2-aminonitrile of general formula III to give pyrimidine-5-carbonitrile of general formula V.

Reaction of the prepared pyrimidine-5-carbonitriles of general formula V (with identical meanings of $R_1$ and $R_3$ as above) in a generally known way with 2-chloroacetamide in methanolic or ethanolic solution in the presence of a sodium alkoxide, preferably sodium methoxide or sodium ethoxide, into the analogous 5-aminofuro- or 5-aminothieno[2,3-d]pyrimidine-6-carboxamides of general formula VII (with identical meanings of $R_1$, $R_3$ and Y as above).

The compounds of general formula VII can also be prepared from the compounds of general formula V (wherein $R_1$, $R_3$ and Y have the above mentioned meanings) by initially reacting these compounds with 2-chloroacetamide in a preferably ethanolic solution in the presence of preferably triethylamine or a secondary cycloaliphatic amine, such as morpholine, piperidine or pyrrolidine, into the compounds of general formula VI (wherein $R_1$, $R_3$ and Y are as defined above) and also converting these compounds in another synthesis step in a preferably water-free ethanolic solution with a catalytic amount of sodium methoxide or sodium ethoxide by means of refluxing into the above-mentioned compounds of general formula VII.

Reaction of the compounds of general formula VII with phosgene derivatives, preferably diphosgene, in a suitable solvent, preferably dioxane or toluene, into the compounds of general formula VIII.

Reaction of the tricyclic dipyrimidine-2,4-diones of general formula VIII with a halogenating agent, preferably dichlorophenylphosphine oxide, phosphortrichloride, phosphorpentachloride, phosphoroxychloride and/or the mixtures thereof, each in the heat, into the tricyclic 2,4-dichloropyrimidines of general formula IX, wherein $R_1$, $R_3$ and Y are as defined above.

Reaction of the 2,4-dichloropyrimidines of general formula IX with O-, N-, S- or C-nucleophiles, preferably alcoholates, amines and thiolates, in alkanols or optionally aprotic, dipolar solvents while heating, in exceptional cases also at room temperature, to give the tricyclic 2-chloro-pyrimidines of general formula X, wherein $R_1$, $R_3$, $R_5$ and Y are as defined above.

Reaction of the 2-chloro-pyrimidines of general formula X with O-, N-, S- or C-nucleophiles, preferably alcoholates, amines and thiolates, in alkanols or optionally aprotic, dipolar solvents while heating, in exceptional cases also at room temperature, into the compounds of general formula 1b, wherein $R_1$, $R_3$, $R_4$, $R_5$ and Y are as defined above.

according to scheme 2

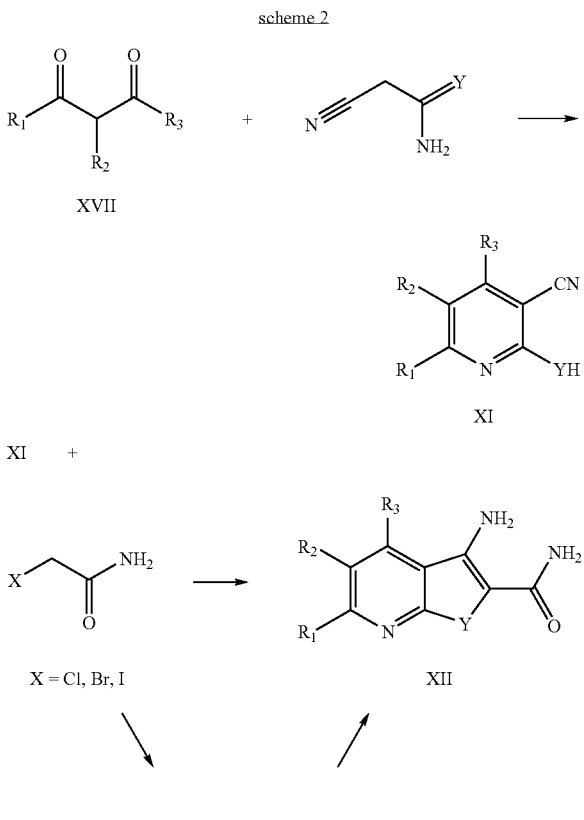

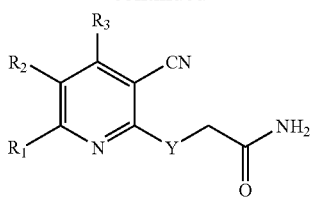
XIIa

XII + 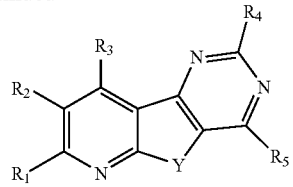 →

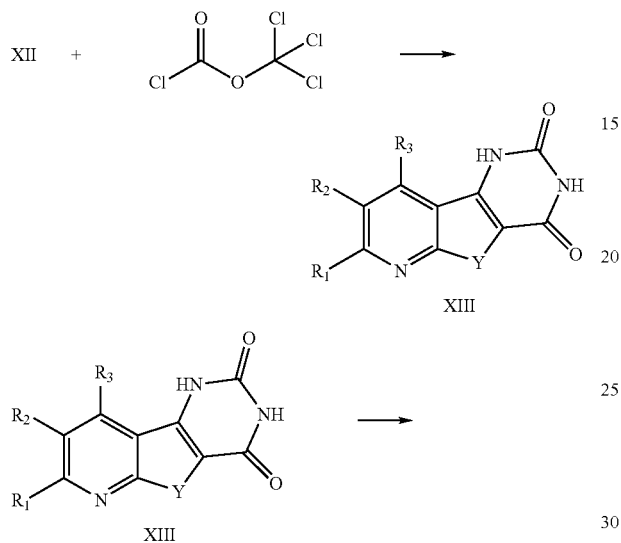
XIII

XIII →

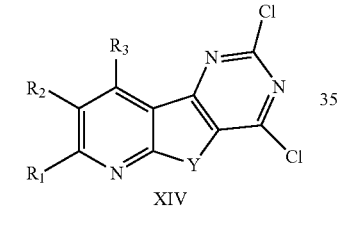
XIV

XIV →

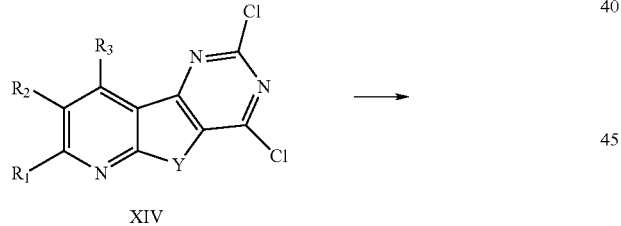
XV

XV →

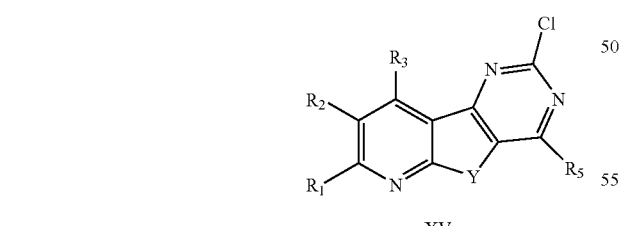

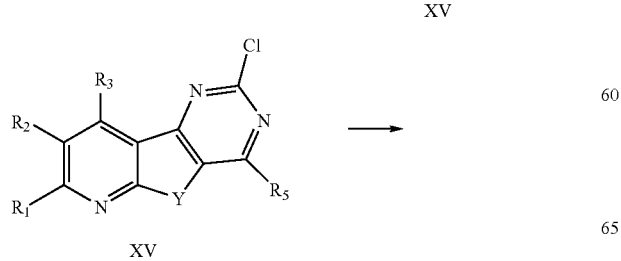
1a

Reaction of a 1,3-diketone of general formula XVII (with identical meanings of $R_1$, $R_2$, $R_3$) with cyanothioacetamide for Y=S or cyanoacetamide for Y=O in a suitable solvent, preferably acetone or ethanol, into pyridine-3-carbonitrile of general formula XI.

Reaction of the prepared pyridine-3-carbonitriles of general formula XI (with identical meanings of $R_1$, $R_2$ and $R_3$ as above) in generally known manner with 2-chloroacetamide in methanolic or ethanolic solution in the presence of a sodium alkoxide, preferably sodium methoxide or sodium ethoxide, into the carboxamides of general formula XII (with identical meanings of $R_1$, $R_2$, $R_3$ and Y as above).

The compounds of general formula XIIa can also be prepared from the compounds of general formula XI (wherein $R_1$, $R_2$, $R_3$ and Y are as defined above) by initially reacting these compounds with 2-chloroacetamide in a preferably ethanolic solution in the presence of preferably triethylamine or a secondary cycloaliphatic amine, such as morpholine, piperidine, or pyrrolidine, into the compounds of general formula XIIa (wherein $R_1$, $R_2$, $R_3$ and Y are as defined above), and also converting these compounds in another synthesis step in a preferably water-free ethanolic solution with a catalytic amount of sodium methoxide or sodium ethoxide by means of refluxing into the above mentioned compounds of general formula XII.

Reaction of the compounds of general formula XII with phosgene derivatives, preferably diphosgene, in a suitable solvent, preferably dioxane or toluene into the compounds of general formula XIII.

Reaction of the tricyclic dipyrimidine-2,4-diones of general formula XIII with a halogenating agent, preferably dichlorophenylphosphine oxide, phosphortrichloride, phosphorpentachloride, phosphoroxychloride or the mixtures thereof, each in the heat, into the tricyclic 2,4-dichloropyrimidines of general formula XV, wherein $R_1$, $R_2$, $R_3$ and Y are as defined above.

Reaction of the 2,4-dichloropyrimidines of general formula XIV with O-, N-, S- or C-nucleophiles, preferably alcoholates, amines and thiolates, in alkanols, or optionally aprotic, dipolar solvents while heating, in exceptional cases also at room temperature, into the tricyclic 2-chloro-pyrimidines of general formula XV, wherein $R_1$, $R_2$, $R_3$, $R_5$ and Y are as defined above.

Reaction of the 2-chloro-pyrimidines of general formula XV with O-, N-, S- or C-nucleophiles, preferably alcoholates, amines and thiolates, in alkanols or optionally aprotic, dipolar solvents while heating, in exceptional cases also at room temperature, into the compounds of general formula 1a, wherein $R_1$, $R_2$, $R_3$, $R_4$, $R_5$ and Y are as defined above.

The pyridine-3-carbonitriles of general formula XIX can also be prepared by the following reactions (scheme 3):

scheme 3

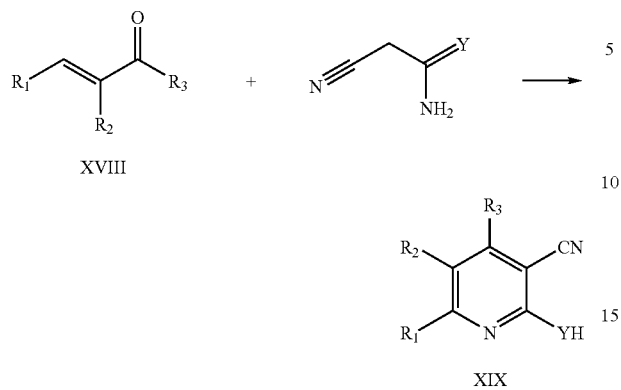

By reaction of a suitable α,β-unsaturated ketone of general formula XVIII (with identical meaning of $R_1$, $R_2$, $R_3$) with cyanothioacetamide for Y=S or cyanoacetamide for Y=O in a suitable solvent, preferably acetone by the addition of an oxidizer, such as oxygen or sulfur, into the pyridine-3-carbonitrile of general formula XIX.

The $R_2$-$R_3$-anellated carbonitriles can be prepared according to scheme 4:

scheme 4

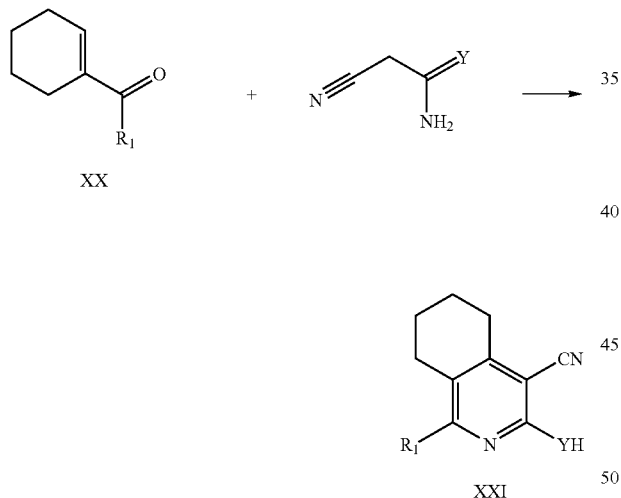

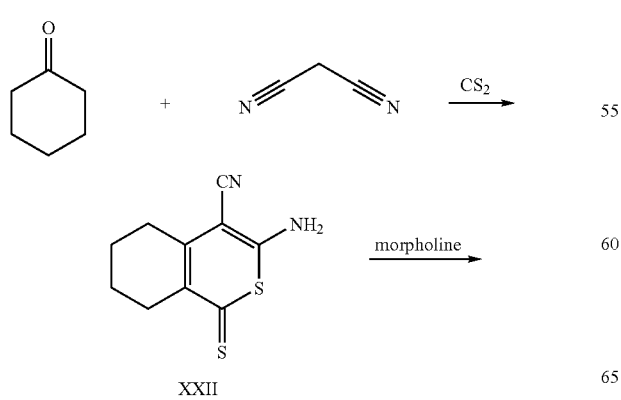

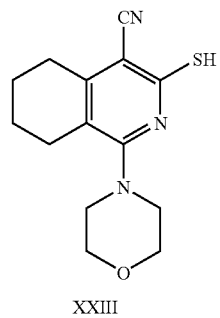

By reaction of a cyclic α,β-unsaturated ketone of general formula XX with cyanothioacetamide for Y=S or cyanoacetamide for Y=O in a suitable solvent, preferably acetone by the addition of a base, preferably $K_2CO_3$ and an oxidizer, such as oxygen or sulfur, into pyridine-3-carbonitrile of general formula XXI.

or

By reaction of a cyclic ketone, e.g. cyclohexanone, with malondinitrile and carbon disulfide by the addition of a suitable base, preferably triethylamine, into the carbonitriles of formula XXII in a suitable solvent, preferably methanol and subsequent reaction with a secondary amine, e.g. morpholine, into the compounds of formula XXIII.

The compounds prepared according to scheme 4 can then be reacted into the compounds of general formula 1c in analogy to scheme 2.

The $R_1$-$R_2$-anellated carbonitriles can be prepared according to scheme 5:

scheme 5

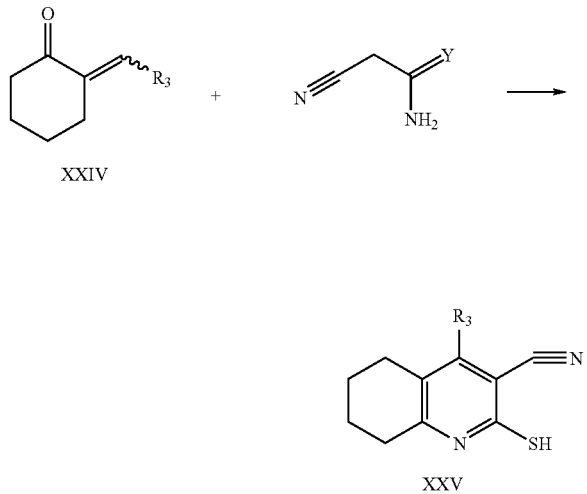

By reaction of a cyclic α,β-unsaturated ketone of general formula XXIV with cyanothioacetamide for Y=S or cyanoacetamide for Y=O in a suitable solvent, preferably acetone by the addition of a base, preferably $K_2CO_3$ and an oxidizer, such as oxygen or sulphur, into the anellated carbonitriles of formula XXV.

Furthermore, the pyridine-3-carbonitriles can be prepared in analogy to PCT/US03/17343 as shown in scheme 6.

scheme 6

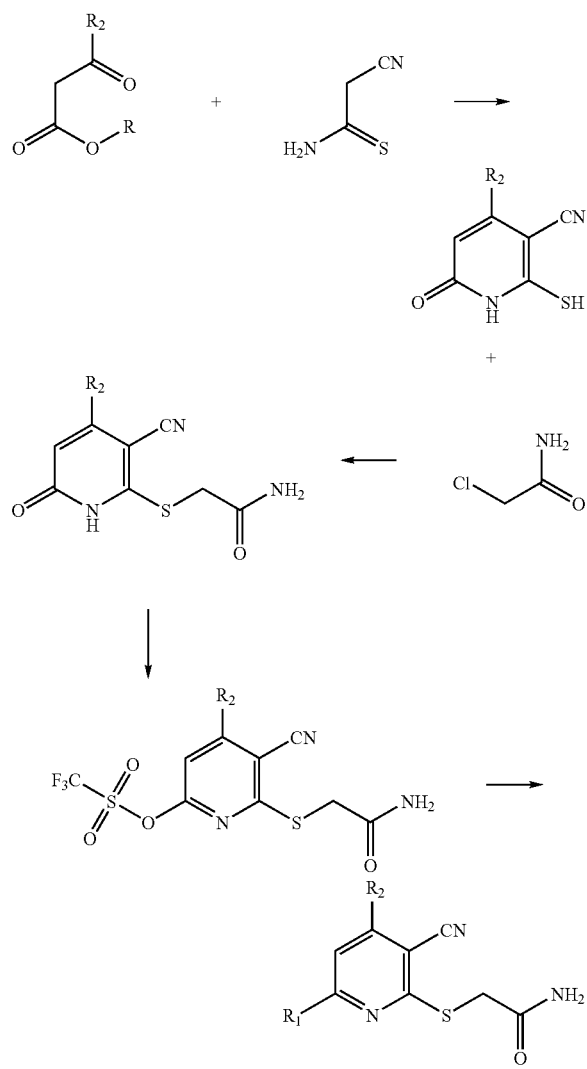

The compounds of general formulae 1a, 1b, 1c and 1d are strong inhibitors of phosphodiesterase 4 and the release of TNFalpha. Their in vivo therapeutic potential has been proved by the inhibition of the asthmatic late-phase reaction (eosinophilia) in the pulmonary lavage fluid of guinea-pigs and by the influence of the allergen-induced vascular permeability in actively sensitized brown rats (R. Norwegicus). The results are shown in detail in below Example 23.

Particularly preferred compounds as to the PDE4 inhibition are:

4-Ethoxy-9-ethyl-7-(4-(pyrimidyl-2-yl)piperazin-1-yl)-2-piperazin-1-yl-pyrido[3',2':4,5]thieno[3,2-d]pyrimidine
4-Ethoxy-9-ethyl-7-(4-methyl-phenyl)-2-(piperazin-1-yl)-pyrido[3',2':4,5]thieno[3,2-d]pyrimidine
2-Ethoxy-9-ethyl-7-(4-methyl-phenyl)-4-(piperazin-1-yl)-pyrido[3',2':4,5]thieno[3,2-d]pyrimidine
4-Ethoxy-7-(4-ethoxy-phenyl)-9-ethyl-2-(piperazin-1-yl)-pyrido[3',2':4,5]thieno[3,2-d]pyrimidine
7-(4-Ethoxy-phenyl)-9-ethyl-2-(piperazin-1-yl)-4-n-propoxy-pyrido[3',2':4,5]thieno[3,2-d]pyrimidine
2-Ethoxy-7-(4-ethoxy-phenyl)-9-ethyl-4-(piperazin-1-yl)-pyrido[3',2':4,5]thieno[3,2-d]pyrimidine
4-Ethoxy-9-ethyl-7-(4-methylthio-phenyl)-2-(piperazin-1-yl)-pyrido[3',2':4,5]thieno[3,2-d]pyrimidine
4-Ethoxy-7-(4-methyl-phenyl)-9-iso-propyl-2-(piperazin-1-yl)-pyrido[3',2':4,5]thieno-[3,2-d]pyrimidine
4-Ethoxy-9-ethyl-7-[4-(4-methoxyphenoxy)phenyl]-2-(piperazin-1-yl)-pyrido[3',2':4,5]thieno[3,2-d]pyrimidine
4-Ethoxy-9-ethyl-7-(2,3-dihydrobenzo[b][1,4]dioxin-6-yl)-2-(piperazin-1-yl)-pyrido[3',2':4,5]thieno[3,2-d]pyrimidine
2-Ethoxy-9-ethyl-7-(2,3-dihydrobenzo[b][1,4]dioxin-6-yl)-4-(piperazin-1-yl)-pyrido[3',2':4,5]thieno[3,2-d]pyrimidine
4-Ethoxy-9-ethyl-7-(3,4-methylenedioxyphenyl)-2-piperazin-1-yl-pyrido[3',2':4,5]thieno-[3,2-d]pyrimidine
4-Ethoxy-7-(4-methoxy-phenyl)-2-(piperazin-1-yl)-9-trifluoromethyl-pyrido[3',2':4,5]thieno[3,2-d]pyrimidine
4-Ethoxy-7-(4-methyl-phenyl)-2-(piperazin-1-yl)-9-trifluoromethyl-pyrido[3',2':4,5]thieno[3,2-d]pyrimidine
7-(2,3-Dihydrobenzo[b][1,4]dioxin-6-yl)-4-ethoxy-2-(piperazin-1-yl)-9-trifluoromethyl-pyrido[3',2':4,5]thieno[3,2-d]pyrimidine
4-Ethoxy-7-(4-(1H-imidazol-1-yl)phenyl)-2-(piperazin-1-yl)-9-trifluoromethyl-pyrido[3',2':4,5]thieno[3,2-d]pyrimidine
4-[4-Ethoxy-2-(piperazin-1-yl)-9-trifluoromethyl-pyrido[3',2':4,5]thieno[3,2-d]pyrimidin-7-yl]-benzoic acid ethyl ester
4-Ethoxy-2-(piperazin-1-yl)-7-(4-(piperidin-1-yl)phenyl)-9-trifluoromethyl-pyrido[3',2':4,5]thieno[3,2-d]pyrimidine
4-Ethoxy-9-ethyl-7-(4-methoxyphenyl)-2-(piperazin-1-yl)-pyrido[3',2':4,5]thieno[3,2-d]pyrimidine
4-Ethoxy-7-(3,4-methylenedioxyphenyl)-2-piperazin-1-yl-9-trifluoromethyl-pyrido[3',2':4,5]thieno-[3,2-d]pyrimidine
4-Ethoxy-7-(4-methylthiophenyl)-2-(piperazin-1-yl)-9-trifluoromethyl-pyrido[3',2':4,5]thieno[3,2-d]pyrimidine
5,6-Dihydro-11-ethoxy-3'-methoxy-9-piperazin-1-yl-7-trifluoromethyl-benzo[h]pyrimido[4',5':4,5]thieno[2,3-b]quinoline
4-Ethoxy-7-(4-(1H-pyrazol-1-yl)-phenyl)-9-ethyl-2-piperazin-1-yl-pyrido[3',2':4,5]thieno[3,2-d]pyrimidine
4-Ethoxy-7-(4-iodo-phenyl)-2-(piperazin-1-yl)-9-trifluoromethyl-pyrido[3',2':4,5]thieno[3,2-d]pyrimidine
4-Ethoxy-7-(4-(1H-pyrazol-1-yl)-phenyl)-2-piperazin-1-yl-9-trifluoromethyl-pyrido[3',2':4,5]thieno[3,2-d]pyrimidine
7-(4-Bromo-phenyl)-4-ethoxy-9-ethyl-2-(piperazin-1-yl)-pyrido[3',2':4,5]thieno[3,2-d]pyrimidine
4-Ethoxy-9-ethyl-7-(4-iodo-phenyl)-2-(piperazin-1-yl)-pyrido[3',2':4,5]thieno[3,2-d]pyrimidine
4-Ethoxy-7-(3-nitro-phenyl)-2-piperazin-1-yl-9-trifluoromethyl-pyrido[3',2':4,5]thieno[3,2-d]pyrimidine
7-(3-Cyano-phenyl)-4-ethoxy-2-piperazin-1-yl-9-trifluoromethyl-pyrido[3',2':4,5]thieno[3,2-d]pyrimidine
N-(4-(4-Ethoxy-9-trifluoromethyl-2-piperazin-1-yl-pyrido[3',2':4,5]thieno[3,2-d]pyrimidin-7-yl)-phenyl)-formamide
N-(4-Ethoxy-9-trifluoromethyl-2-piperazin-1-yl-pyrido[3',2':4,5]thieno[3,2-d]pyrimidin-7-yl)-benzamide trifluoroacetate
N'-Hydroxy-4-(4-ethoxy-9-trifluoromethyl-2-piperazin-1-yl-pyrido[3',2':4,5]thieno[3,2-d]pyrimidin-7-yl)-benzamidine bistrifluoroacetate
N-(4-(4-Ethoxy-9-trifluoromethyl-2-piperazin-1-yl-pyrido[3',2':4,5]thieno[3,2-d]pyrimidin-7-yl)-phenyl)-isonicotinamide
4-Ethoxy-9-trifluoromethyl-2-piperazin-1-yl-7-(4-(1H-pyrrol-1-yl)-phenyl)-pyrido[3',2':4,5]thieno[3,2-d]pyrimidine N-(4-(4-Ethoxy-9-trifluoromethyl-2-piperazin-1-yl-pyrido [3',2':4,5]thieno[3,2-d]pyrimidin-7-yl)-phenyl)-nicotinamide-N-oxide 4-(4-Ethoxy-9-trifluoromethyl-2-piperazin-1-yl-pyrido[3', 2':4,5]thieno[3,2-d]pyrimidin-7-yl)-phenyl-carbamic acid methyl ester N-(4-(4-Ethoxy-9-trifluoromethyl-2-piperazin-1-yl-pyrido [3',2':4,5]thieno[3,2-d]pyrimidin-7-yl)-phenyl)-nicotinamide 7-(3'-Aminobiphen-4-yl)-4-ethoxy-9-methyl-2-piperazin-1-yl-thieno[2,3-d:4,5-d']dipyrimidine 4-Ethoxy-7-(4-[3-furyl]-phenyl)-9-methyl-2-piperazin-1-yl-thieno[2,3-d:4,5-d']dipyrimidine 4-Ethoxy-7-(4-[2-furyl]-phenyl)-9-methyl-2-piperazin-1-yl-thieno[2,3-d:4,5-d']dipyrimidine 4-Ethoxy-9-methyl-2-piperazin-1-yl-7-(4-[3-pyridyl]-phenyl)-thieno[2,3-d:4,5-d']dipyrimidine 4-Ethoxy-9-methyl-2-piperazin-1-yl-7-(4-[4-pyridyl]-phenyl)-thieno[2,3-d:4,5-d']dipyrimidine 7-(4'-Aminobiphen-4-yl)-4-ethoxy-9-methyl-2-piperazin-1-yl-thieno[2,3-d:4,5-d']dipyrimidine 4-Ethoxy-9-methyl-2-piperazin-1-yl-7-(3',4',5'-trimethoxybiphen-4-yl)-thieno[2,3-d:4,5-d']dipyrimidine 4-Ethoxy-9-methyl-7-(4-phenoxy-phenyl)-2-piperazin-1-yl-thieno[2,3-d:4,5-d']dipyrimidine 2'-Amino-4-(4-ethoxy-9-methyl-2-piperazin-1-yl-thieno[2, 3-d:4,5-d']dipyrimidine-7-yl)-biphenyl-4'-carboxylic acid methyl ester 7-(3',4'-Dimethoxybiphen-4-yl)-4-ethoxy-9-methyl-2-piperazin-1-yl-thieno[2,3-d:4,5-d']dipyrimidine 7-(4-[3,5-Dimethyl-isoxazol-4-yl]-phenyl)-4-ethoxy-9-methyl-2-piperazin-1-yl-thieno[2,3-d:4,5-d']dipyrimidine Particularly preferred compounds according to the inhibition of TNF-alpha release are:

7-(3'-Aminobiphen-4-yl)-4-ethoxy-9-methyl-2-piperazin-1-yl-thieno[2,3-d:4,5-d']dipyrimidine 4-Ethoxy-7-(4-[3-furyl]-phenyl)-9-methyl-2-piperazin-1-yl-thieno[2,3-d:4,5-d']dipyrimidine 4-Ethoxy-9-methyl-2-piperazin-1-yl-7-(4-[3-pyrrolyl]-phenyl)-thieno[2,3-d:4,5-d']dipyrimidine 7-(4-[1,2-Dihydroxyethyl]-phenyl)-4-ethoxy-9-methyl-2-piperazin-1-yl-thieno[2,3-d:4,5-d']dipyrimidine 4-Ethoxy-7-(3,4-dimethoxy-phenyl)-9-methyl-2-(piperazin-1-yl)-pyrido[3',2':4,5]thieno[3,2-d]pyrimidine 4-Ethoxy-7-(4-methoxy-phenyl)-9-methyl-2-(piperazin-1-yl)-pyrido[3',2':4,5]thieno[3,2-d]pyrimidine-hydrochloride 2-Ethoxy-7-methyl-9-phenyl-4-(piperazin-1-yl)-pyrido[3', 2':4,5]thieno[3,2-d]pyrimidine-hydrochloride 2-Ethoxy-7-(4-trifluoro-methyl-phenyl)-9-methyl-4-(piperazin-1-yl)-pyrido[3',2':4,5]thieno[3,2-d]pyrimidine 2-(2-Hydroxy-ethoxy)-9-methyl-7-phenyl-4-(piperazin-1-yl)-pyrido[3',2':4,5]thieno[3,2-d]pyrimidine 8-(4-Amino-benzyl)-4-ethoxy-7,9-dimethyl-2-(piperazin-1-yl)-pyrido[3',2':4,5]thieno[3,2-d]pyrimidine 4-Ethoxy-7-(3,4-dimethoxy-phenyl)-9-methyl-2-(piperazin-1-yl)-pyrido[3',2':4,5]thieno[3,2-d]pyrimidine-hydrochloride 4-Ethoxy-7-morpholino-9-phenyl-2-(piperazin-1-yl)-pyrido [3',2':4,5]thieno[3,2-d]pyrimidine 2-Ethoxy-7-(3,4-dimethoxy-phenyl)-9-methyl-4-(piperazin-1-yl)-pyrido[3',2':4,5]thieno[3,2-d]pyrimidine 2-Ethoxy-7-(4-methoxy-phenyl)-9-methyl-4-(piperazin-1-yl)-pyrido[3',2':4,5]thieno[3,2-d]pyrimidine 2-Ethoxy-7,9-dimethyl-8-(4-nitro-benzyl)-4-(piperazin-1-yl)-pyrido[3',2':4,5]thieno[3,2-d]pyrimidine 4-Ethoxy-7,9-diphenyl-2-(piperazin-1-yl)-pyrido[3',2':4,5] thieno[3,2-d]pyrimidine 4-Ethoxy-7-(4-methoxy-phenyl)-9-methyl-2-(piperazin-1-yl)-pyrido[3',2':4,5]thieno[3,2-d]pyrimidine 9-Methyl-7-phenyl-2-(piperazin-1-yl)-4-n-propoxy-pyrido [3',2':4,5]thieno[3,2-d]pyrimidine 4-Ethoxy-7,9-dimethyl-8-(4-nitro-benzyl)-2-(piperazin-1-yl)-pyrido[3',2':4,5]thieno[3,2-d]pyrimidine 4-Ethoxy-7-(4-fluoro-phenyl)-9-methyl-2-(piperazin-1-yl)-pyrido[3',2':4,5]thieno[3,2-d]pyrimidine 4-Ethoxy-2-piperazin-1-yl-7-(3-pyridyl)-9-trifluoromethyl-pyrido[3',2':4,5]thieno[3,2-d]pyrimidine 4-Ethoxy-7-(1-oxy-pyridin-3-yl)-2-(piperazin-1-yl)-9-trifluoromethyl-pyrido[3',2':4,5]thieno[3,2-d]pyrimidine 4-Ethoxy-2-piperazin-1-yl-7-(4-pyridyl)-9-trifluoromethyl-pyrido[3',2':4,5]thieno[3,2-d]pyrimidine 4-Ethoxy-7-(1-oxy-pyridin-4-yl)-2-(piperazin-1-yl)-9-trifluoromethyl-pyrido[3',2':4,5]thieno[3,2-d]pyrimidine 4-Ethoxy-7-(4-(1H-imidazol-1-yl)phenyl)-2-(piperazin-1-yl)-9-trifluoromethyl-pyrido[3',2':4,5]thieno[3,2-d]pyrimidine 4-(2-Hydroxy-ethoxy)-7-[(1H-imidazol-1-yl)phenyl]-2-(piperazin-1-yl)-9-trifluoromethyl-pyrido[3',2':4,5]thieno [3,2-d]pyrimidine 8-Ethoxy-5-morpholino-10-piperazin-1-yl-pyrimido[4',5':4, 5]thieno[2,3-c]-1,2,3,4-tetrahydro-isoquinoline 4-(4-Ethoxy-9-trifluoromethyl-2-piperazin-1-yl-pyrido[3', 2':4,5]thieno[3,2-d]pyrimidin-7-yl)-benzamide trifluoroacetate N'-Hydroxy-4-(4-ethoxy-9-trifluoromethyl-2-piperazin-1-yl-pyrido[3',2':4,5]thieno[3,2-d]pyrimidin-7-yl)-benzamidine bistrifluoroacetat 4-Ethoxy-9-trifluoromethyl-2-piperazin-1-yl-7-(4-(1H-1,2, 4-triazol-4-yl)-phenyl)-pyrido[3',2':4,5]thieno[3,2-d]pyrimidine N-(4-(4-Ethoxy-9-trifluoromethyl-2-piperazin-1-yl-pyrido [3',2':4,5]thieno[3,2-d]pyrimidin-7-yl)-phenyl)-isonicotinamide N-(4-(4-Ethoxy-9-trifluoromethyl-2-piperazin-1-yl-pyrido [3',2':4,5]thieno[3,2-d]pyrimidin-7-yl)-phenyl)-formamide N-(4-(4-Ethoxy-9-trifluoromethyl-2-piperazin-1-yl-pyrido [3',2':4,5]thieno[3,2-d]pyrimidin-7-yl)-phenyl)-nicotinamide In particular the following compounds were characterized as having cytotoxic activity by Applicant:

4-Ethoxy-7-(4-[2-furyl]-phenyl)-9-methyl-2-piperazin-1-yl-thieno[2,3-d:4,5-d']dipyrimidine 4-Ethoxy-9-methyl-2-piperazin-1-yl-7-(4-[N—BOC-3-pyrrolyl]-phenyl)-thieno[2,3-d:4,5-d']dipyrimidine 4-Ethoxy-9-ethyl-7-(4-methyl-phenyl)-2-(piperazin-1-yl)-pyrido[3',2':4,5]thieno[3,2-d]pyrimidine 2-Ethoxy-7-(4-methyl-phenyl)-4-(piperazin-1-yl)-9-propyl-pyrido[3',2':4,5]thieno[3,2-d]pyrimidine 2-Ethoxy-7-(4-methyl-phenyl)-4-(piperazin-1-yl)-9-propyl-pyrido[3',2':4,5]thieno[3,2-d]pyrimidine hydrochloride 2-Ethoxy-9-methyl-4-(piperazin-1-yl)-7-phenyl-pyrido[3', 2':4,5]furo[3,2-d]pyrimidine 7-(2,3-Dihydrobenzo[b][1,4]dioxin-6-yl)-2-ethoxy-9-ethyl-4-piperazino-pyrido[3',2':4,5]thieno[3,2-d]pyrimidine 4-Ethoxy-9-ethyl-7-(4-methoxy-phenyl)-2-piperazin-1-yl-pyrido[3',2':4,5]thieno[3,2-d]pyrimidine hydrochloride 4-Ethoxy-7-(4-methylthio-phenyl)-2-piperazine-1-yl-9-trifluoromethyl-pyrido[3',2':4,5]thieno[3,2-d]pyrimidine Mono-[4-Ethoxy-7-(4-methylthio-phenyl)-2-piperazin-1-yl-9-trifluoromethyl-pyrido[3',2':4,5]thieno[3,2-d]pyrimidine]citrate 7-(4-Amino-phenyl)-4-ethoxy-2-piperazin-1-yl-9-trifluoromethyl-pyrido[3',2':4,5]thieno[3,2-d]pyrimidine 4-Ethoxy-9-methyl-2-piperazin-1-yl-7-(4-[4-pyridyl]-phenyl)-thieno[2,3-d:4,5-d']dipyrimidine 4-Ethoxy-9-methyl-2-piperazin-1-yl-7-(4-[3-pyridyl]-phenyl)-thieno[2,3-d:4,5-d']dipyrimidine 4-Ethoxy-9-methyl-2-piperazin-1-yl-7-(4-[3-pyrrolyl]-phenyl)-thieno[2,3-d:4,5-d']dipyrimidine 4-(4-Ethoxy-9-methyl-2-piperazin-1-yl-thieno[2,3-d:4,5-d']dipyrimidin-7-yl)-biphenyl-3'-carboxylic acid potassium salt 7-(4'-Aminobiphen-4-yl)-4-ethoxy-9-methyl-2-piperazin-1-yl-thieno[2,3-d:4,5-d']dipyrimidine 4-Ethoxy-9-methyl-2-piperazin-1-yl-7-(4-[5-pyrimidinyl]-phenyl)-thieno[2,3-d:4,5-d']dipyrimidine 7-(3',4'-Dimethoxybiphen-4-yl)-4-ethoxy-9-methyl-2-piperazin-1-yl-thieno[2,3-d:4,5-d']dipyrimidine 4-Ethoxy-7-(4-methoxy-phenyl)-9-methyl-2-piperazin-1-yl-pyrido[3',2':4,5]thieno[3,2-d]pyrimidine 2-Ethoxy-9-methyl-7-(3,4-methylenedioxy-phenyl)-4-piperazin-1-yl-pyrido[3',2':4,5]-thieno[3,2-d]pyrimidine 4-Ethoxy-9-ethyl-7-(4-methoxy-phenyl)-2-piperazin-1-yl-pyrido[3',2':4,5]thieno[3,2-d]pyrimidine The below tables give particularly preferred compounds: formula 1(a), wherein Y=S and substituents $R^1$, $R^2$, $R^3$, $R^4$, $R^5$ which have the following meanings:

| $R_1$ | $R_2$ | $R_3$ | $R_4$ | $R_5$ |
|---|---|---|---|---|
| 3,4-(MeO)$_2$—Ph | H | Me | Piperazin-1-yl | OEt |
| 4-MeO—Ph | H | Me | Piperazin-1-yl | OEt |
| 4-F—Ph | H | Me | Piperazin-1-yl | OEt |
| Ph | H | Me | Piperazin-1-yl | OiPr |
| Ph | H | Me | Piperazin-1-yl | OCH$_2$CHF$_2$ |
| Ph | H | Ph | Piperazin-1-yl | OEt |
| Me | 4'-NO$_2$—Ph—CH$_2$ | Me | Piperazin-1-yl | OEt |
| Me | 4'-NH$_2$—Ph—CH$_2$ | Me | Piperazin-1-yl | OEt |
| 3,4-Methylene-dioxyphenyl | H | Me | Piperazin-1-yl | OEt |
| Ph | H | Me | Piperazin-1-yl | OnPr |
| Ph | H | Me | Piperazin-1-yl | OEt |
| Ph | H | Me | Piperazin-1-yl | OCH$_2$CH$_2$OH |
| 3,4-(MeO)$_2$—Ph | H | Me | OEt | Piperazin-1-yl |
| 4-MeO—Ph | H | Me | OEt | Piperazin-1-yl |
| Ph | H | Me | OCH$_2$CHF$_2$ | Piperazin-1-yl |
| Me | 4'-NO$_2$—Ph—CH$_2$ | Me | OEt | Piperazin-1-yl |
| Ph | 4'-NO$_2$—Ph—CH$_2$ | Me | OEt | Piperazin-1-yl |
| 3,4-(MeO)$_2$—Ph | H | Me | nPr | Piperazin-1-yl |
| Ph | H | Me | OCH$_2$CH$_2$OH | Piperazin-1-yl |
| Ph | H | Me | OEt | Piperazin-1-yl |
| Ph | H | Me | OiPr | Piperazin-1-yl |
| 3,4-Methylene-dioxyphenyl | H | Me | OEt | Piperazin-1-yl |
| 4-(Pyrimidyl-2-yl)piperazin-1-yl- | H | Et | Piperazin-1-yl | OEt |
| 4-Me—Ph | H | Et | Piperazin-1-yl | OEt |
| 4-EtO—Ph | H | Et | Piperazin-1-yl | OEt |
| 4-EtO—Ph | H | Et | Piperazin-1-yl | OProp |
| 4-MeS—Ph | H | Et | Piperazin-1-yl | OEt |
| 4-Me—Ph | H | Et | Piperazin-1-yl | OiPr |
| 4-(4-MeOPhO)Ph | H | Et | Piperazin-1-yl | OEt |
| 2,3-Dihydro-benzo[b][1,4]-dioxin-6-yl | H | Et | Piperazin-1-yl | OEt |
| 3,4-Methylene-dioxyphenyl | H | Et | Piperazin-1-yl | OEt |
| 4-MeO—Ph | H | Et | Piperazin-1-yl | OEt |
| 4-(1H-pyrazol-1-yl)-Ph | H | Et | Piperazin-1-yl | OEt |
| 4-Br—Ph | H | Et | Piperazin-1-yl | OEt |
| 4-Cl—Ph | H | Et | Piperazin-1-yl | OEt |
| 4-I—Ph | H | Et | Piperazin-1-yl | OEt |
| Morpholine | H | Ph | Piperazin-1-yl | OEt |
| 4-MeO—Ph | H | CF$_3$ | Piperazin-1-yl | OEt |
| 4-Me—Ph | H | CF$_3$ | Piperazin-1-yl | OEt |
| 2,3-Dihydro-benzo[b][1,4]-dioxin-6-yl | H | CF$_3$ | Piperazin-1-yl | OEt |
| 4-Imidazol-1-yl-Ph | H | CF$_3$ | Piperazin-1-yl | OEt |
| 4-Imidazol-1-yl-Ph | H | CF$_3$ | Piperazin-1-yl | OCH$_2$CH$_2$OH |
| 4-(Piperidin-1-yl)-Ph | H | CF$_3$ | Piperazin-1-yl | OEt |
| 4-Morpholino-Ph | H | CF$_3$ | Piperazin-1-yl | OEt |
| 3,4-Methylene-dioxyphenyl | H | CF$_3$ | Piperazin-1-yl | OEt |
| 4-MeS—Ph | H | CF$_3$ | Piperazin-1-yl | OEt |
| 4-EtOOC—Ph | H | CF$_3$ | Piperazin-1-yl | OEt |
| 4-(1H-pyrazol-1-yl)-Ph | H | CF$_3$ | Piperazin-1-yl | OEt |
| 4-F—Ph | H | CF$_3$ | Piperazin-1-yl | OEt |
| 4-I—Ph | H | CF$_3$ | Piperazin-1-yl | OEt |
| 3-NO$_2$—Ph | H | CF$_3$ | Piperazin-1-yl | OEt |
| 4-NO$_2$—Ph | H | CF$_3$ | Piperazin-1-yl | OEt |
| 3-CN—Ph | H | CF$_3$ | Piperazin-1-yl | OEt |
| 4-CN—Ph | H | CF$_3$ | Piperazin-1-yl | OEt |
| 3-NH$_2$—Ph | H | CF$_3$ | Piperazin-1-yl | OEt |
| 4-NH$_2$—Ph | H | CF$_3$ | Piperazin-1-yl | OEt |
| 4-MeS—Ph | H | CF$_3$ | Piperazin-1-yl | OEt |
| 4-MeS(O)—Ph | H | CF$_3$ | Piperazin-1-yl | OEt |
| Pyridin-4-yl | H | CF$_3$ | Piperazin-1-yl | OEt |
| Pyridin-4-yl-N-oxide | H | CF$_3$ | Piperazin-1-yl | OEt |
| Pyridin-3-yl | H | CF$_3$ | Piperazin-1-yl | OEt |

-continued

| R₁ | R₂ | R₃ | R₄ | R₅ |
|---|---|---|---|---|
| 4-(Pyrazin-2-yl) | H | CF₃ | Piperazin-1-yl | OEt |
| 4(HCONH)—Ph | H | CF₃ | Piperazin-1-yl | OEt |
| 4-(Pyridin-4-yl-CONH)—Ph | H | CF₃ | Piperazin-1-yl | OEt |
| 4-(Pyridin-3-yl-CONH)—Ph | H | CF₃ | Piperazin-1-yl | OEt |
| 4-(Pyridin-3-yl-N-Oxid-CONH)—Ph | H | CF₃ | Piperazin-1-yl | OEt |
| 4-(1H-1,2,4-triazol-4-yl)-Ph | H | CF₃ | Piperazin-1-yl | OEt |
| 4-(1H-pyrrol-1-yl)-Ph | H | CF₃ | Piperazin-1-yl | OEt |
| 4(CH₃OOCNH)—Ph | H | CF₃ | Piperazin-1-yl | OEt |
| isoPr | H | isoPr | Piperazin-1-yl | OEt |
| 2,3-Dihydro-benzo[b][1,4]-dioxin-6-yl | H | Et | OEt | Piperazin-1-yl |
| 4-EtO—Ph | H | Et | OEt | Piperazin-1-yl |
| 4-Me—Ph | H | Et | OEt | Piperazin-1-yl |
| 4-Me—Ph | H | Et | OCH₂CH₂OH | Piperazin-1-yl | formula 1(a), wherein Y=O and substituents R¹, R², R³, R⁴, R⁵ have the following meanings:

| R₁ | R₂ | R₃ | R₄ | R₅ |
|---|---|---|---|---|
| Ph | H | Me | Piperazin-1-yl | OEt |
| Ph | H | Me | OEt | Piperazin-1-yl | formula 1(b), wherein Y=S and substituents R¹, R³, R⁴, R⁵ have the following meanings:

| R₁ | R₃ | R₄ | R₅ |
|---|---|---|---|
| 3-NH₂—Ph-4-Ph | Me | Piperazin-1-yl | OEt |
| 4-(3-furyl)-Ph | Me | Piperazin-1-yl | OEt |
| 4-(2-furyl)-Ph | Me | Piperazin-1-yl | OEt |
| 4-(3-pyridyl)-Ph | Me | Piperazin-1-yl | OEt |
| 4-(4-pyridyl)-Ph | Me | Piperazin-1-yl | OEt |
| 4-NH₂—Ph—Ph | Me | Piperazin-1-yl | OEt |
| 3,4,5-(CH₃O)₃—Ph—Ph | Me | Piperazin-1-yl | OEt |
| 4-PhO—Ph | Me | Piperazin-1-yl | OEt |
| 2-NH₂-4-CH₃OOC—Ph—Ph | Me | Piperazin-1-yl | OEt |
| 3-CH₃OOC—Ph—Ph | Me | Piperazin-1-yl | OEt |
| 3,4-(CH₃O)₂—Ph—Ph | Me | Piperazin-1-yl | OEt |
| 3,5-(CH₃)₂-isoxazol-4-yl-Ph | Me | Piperazin-1-yl | OEt |
| Phenyl | Me | Piperazin-1-yl | OEt |
| 4-Br—Ph | Me | Piperazin-1-yl | OEt |
| 3-NH₂—Ph | Me | Piperazin-1-yl | OEt |
| 4-(pyrrol-3-yl)-Ph | Me | Piperazin-1-yl | OEt |
| 4-(pyrimidin-5-yl)-Ph | Me | Piperazin-1-yl | OEt |
| 4-(pyrid-3-yl-hydroxymethyl)-Ph | Me | Piperazin-1-yl | OEt |
| Ph—Ph | Me | Piperazin-1-yl | OEt |
| 4-(isoPropO)—Ph | Me | Piperazin-1-yl | OEt |
| 4-Vinyl-Ph | Me | Piperazin-1-yl | OEt | formula 1(a) or 1(b), which are explicitly:
2-(2-Hydroxyethoxy)-9-methyl-7-phenyl-4-(piperazin-1-yl)-pyrido[3',2':4,5]thieno[3,2-d]pyrimidine;
2-Ethoxy-7-(3,4-dimethoxy-phenyl)-9-methyl-4-(piperazin-1-yl)-pyrido[3',2':4,5]thieno[3,2-d]pyrimidine;
2-Ethoxy-7-(4-methoxy-phenyl)-9-methyl-4-(piperazin-1-yl)-pyrido[3',2':4,5]thieno[3,2-d]pyrimidine;
2-Ethoxy-9-ethyl-7-(4-methyl-phenyl)-4-(piperazin-1-yl)-pyrido[3',2':4,5]thieno[3,2-d]pyrimidine
2-Ethoxy-7-(4-ethoxy-phenyl)-9-ethyl-4-(piperazin-1-yl)-pyrido[3',2':4,5]thieno[3,2-d]pyrimidine
2-Ethoxy-9-ethyl-7-(2,3-dihydrobenzo[b][1,4]dioxin-6-yl)-4-(piperazin-1-yl)-pyrido[3',2':4,5]thieno[3,2-d]pyrimidine
4-Ethoxy-9-trifluoromethyl-7-(pyrazin-2-yl)-2-piperazino-pyrido[3',2':4,5]thieno[3,2-d]pyrimidine
4-Ethoxy-9-ethyl-7-(4-(pyrimidyl-2-yl)piperazin-1-yl)-2-piperazin-1-yl-pyrido[3',2':4,5]thieno[3,2-d]pyrimidine
4-Ethoxy-7-morpholino-9-phenyl-2-(piperazin-1-yl)-pyrido[3',2':4,5]thieno[3,2-d]pyrimidine;
4-Ethoxy-7-phenyl-9-methyl-2-(piperazin-1-yl)-pyrido[3',2':4,5]furo[3,2-d]pyrimidine;
4-Ethoxy-7,9-dimethyl-8-(4-nitro-benzyl)-2-(piperazin-1-yl)-pyrido[3',2':4,5]thieno[3,2-d]pyrimidine;
4-Ethoxy-7-(3,4-dimethoxy-phenyl)-9-methyl-2-(piperazin-1-yl)-pyrido[3',2':4,5]thieno[3,2-d]pyrimidine;
4-Ethoxy-9-ethyl-7-(4-methyl-phenyl)-2-(piperazin-1-yl)-pyrido[3',2':4,5]thieno[3,2-d]pyrimidine
4-Ethoxy-7-(4-fluorophenyl)-9-methyl-2-(piperazin-1-yl)-pyrido[3',2':4,5]furo[3,2-d]pyrimidine
7-(4-Ethoxy-phenyl)-9-ethyl-2-(piperazin-1-yl)-4-n-propoxy-pyrido[3',2':4,5]thieno[3,2-d]pyrimidine
4-Ethoxy-7-(4-ethoxy-phenyl)-9-ethyl-2-(piperazin-1-yl)-pyrido[3',2':4,5]thieno[3,2-d]pyrimidine
4-Ethoxy-7-(4-(pyrimidin-2-yl)piperazin-1-yl)-9-ethyl-2-(piperazin-1-yl)-pyrido[3',2':4,5]thieno[3,2-d]pyrimidine
4-Ethoxy-9-ethyl-7-(4-methylthio-phenyl)-2-(piperazin-1-yl)-pyrido[3',2':4,5]thieno[3,2-d]pyrimidine
4-Ethoxy-7-(4-methyl-phenyl)-9-iso-propyl-2-(piperazin-1-yl)-pyrido[3',2':4,5]thieno-[3,2-d]pyrimidine
4-Ethoxy-9-ethyl-7-[4-(4-methoxyphenoxy)phenyl]-2-(piperazin-1-yl)-pyrido[3',2':4,5]thieno[3,2-d]pyrimidine
4-Ethoxy-9-ethyl-7-(2,3-dihydrobenzo[b][1,4]dioxin-6-yl)-2-(piperazin-1-yl)-pyrido[3',2':4,5]thieno[3,2-d]pyrimidine
4-Ethoxy-9-ethyl-7-(3,4-methylenedioxyphenyl)-2-piperazin-1-yl-pyrido[3',2':4,5]thieno-[3,2-d]pyrimidine
4-Ethoxy-7-(4-methoxy-phenyl)-2-(piperazin-1-yl)-9-trifluoromethyl-pyrido[3',2':4,5]thieno[3,2-d]pyrimidine
4-Ethoxy-7-(4-methyl-phenyl)-2-(piperazin-1-yl)-9-trifluoromethyl-pyrido[3',2':4,5]thieno[3,2-d]pyrimidine
7-(2,3-Dihydrobenzo[b][1,4]dioxin-6-yl)-4-ethoxy-2-(piperazin-1-yl)-9-trifluoromethyl-pyrido[3',2':4,5]thieno[3,2-d]pyrimidine
4-Ethoxy-7-(4-(1H-imidazol-1-yl)phenyl)-2-(piperazin-1-yl)-9-trifluoromethyl-pyrido[3',2':4,5]thieno[3,2-d]pyrimidine
4-[4-Ethoxy-2-(piperazin-1-yl)-9-trifluoromethyl-pyrido[3',2':4,5]thieno[3,2-d]pyrimidin-7-yl]-benzoic acid ethyl ester
4-Ethoxy-2-(piperazin-1-yl)-7-(4-(piperidin-1-yl)phenyl)-9-trifluoromethyl-pyrido[3',2':4,5]thieno[3,2-d]pyrimidine
4-Ethoxy-9-ethyl-7-(4-methoxyphenyl)-2-(piperazin-1-yl)-pyrido[3',2':4,5]thieno[3,2-d]pyrimidine
4-Ethoxy-7-(3,4-methylenedioxyphenyl)-2-piperazin-1-yl-9-trifluoromethyl-pyrido[3',2':4,5]thieno-[3,2-d]pyrimidine 4-Ethoxy-7-(4-methylthiophenyl)-2-(piperazin-1-yl)-9-trifluoromethyl-pyrido[3',2':4,5]thieno[3,2-d]pyrimidine 4-Ethoxy-7-(4-(1H-pyrazol-1-yl)-phenyl)-9-ethyl-2-piperazin-1-yl-pyrido[3',2':4,5]thieno[3,2-d]pyrimidine 4-Ethoxy-7-(4-iodo-phenyl)-2-(piperazin-1-yl)-9-trifluoromethyl-pyrido[3',2':4,5]thieno[3,2-d]pyrimidine 4-Ethoxy-7-(4-(1H-pyrazol-1-yl)-phenyl)-2-piperazin-1-yl-9-trifluoromethyl-pyrido[3',2':4,5]thieno[3,2-d]pyrimidine 7-(4-Bromo-phenyl)-4-ethoxy-9-ethyl-2-(piperazin-1-yl)-pyrido[3',2':4,5]thieno[3,2-d]pyrimidine 4-Ethoxy-9-ethyl-7-(4-iodo-phenyl)-2-(piperazin-1-yl)-pyrido[3',2':4,5]thieno[3,2-d]pyrimidine 4-Ethoxy-7-(3-nitro-phenyl)-2-piperazin-1-yl-9-trifluoromethyl-pyrido[3',2':4,5]thieno[3,2-d]pyrimidine 7-(3-Cyano-phenyl)-4-ethoxy-2-piperazin-1-yl-9-trifluoromethyl-pyrido[3',2':4,5]thieno[3,2-d]pyrimidine 7-(4-Cyano-phenyl)-4-ethoxy-2-piperazin-1-yl-9-trifluoromethyl-pyrido[3',2':4,5]thieno[3,2-d]pyrimidine 7-(3-Amino-phenyl)-4-ethoxy-2-piperazin-1-yl-9-trifluoromethyl-pyrido[3',2':4,5]thieno[3,2-d]pyrimidine 7-(4-Amino-phenyl)-4-ethoxy-2-piperazin-1-yl-9-trifluoromethyl-pyrido[3',2':4,5]thieno[3,2-d]pyrimidine 4-Ethoxy-9-methyl-7-(4-methylsulfinyl-phenyl)-2-(piperazin-1-yl)-pyrido[3',2':4,5]thieno[3,2-d]pyrimidine N-(4-(4-Ethoxy-9-trifluoromethyl-2-piperazin-1-yl-pyrido[3',2':4,5]thieno[3,2-d]pyrimidin-7-yl)-phenyl)-formamide N-(4-(4-Ethoxy-9-trifluoromethyl-2-piperazin-1-yl-pyrido[3',2':4,5]thieno[3,2-d]pyrimidin-7-yl)-phenyl)-isonicotinamide 4-Ethoxy-9-trifluoromethyl-2-piperazin-1-yl-7-(4-(1H-pyrrol-1-yl)-phenyl)-pyrido[3',2':4,5]thieno[3,2-d]pyrimidine N-(4-(4-Ethoxy-9-trifluoromethyl-2-piperazin-1-yl-pyrido[3',2':4,5]thieno[3,2-d]pyrimidin-7-yl)-phenyl)-nicotinamide-N-oxide 4-(4-Ethoxy-9-trifluoromethyl-2-piperazin-1-yl-pyrido[3',2':4,5]thieno[3,2-d]pyrimidin-7-yl)-phenyl-carbamic acid methyl ester N-(4-(4-Ethoxy-9-trifluoromethyl-2-piperazin-1-yl-pyrido[3',2':4,5]thieno[3,2-d]pyrimidin-7-yl)-phenyl)-nicotinamide N-(4-Ethoxy-9-trifluoromethyl-2-piperazin-1-yl-pyrido[3',2':4,5]thieno[3,2-d]pyrimidin-7-yl)-benzamide trifluoroacetate N'-Hydroxy-4-(4-ethoxy-9-trifluoromethyl-2-piperazin-1-yl-pyrido[3',2':4,5]thieno[3,2-d]pyrimidin-7-yl)-benzamidine bistrifluoroacetate 7-(3'-Aminobiphen-4-yl)-4-ethoxy-9-methyl-2-piperazin-1-yl-thieno[2,3-d:4,5-d']dipyrimidine 4-Ethoxy-7-(4-[3-furyl]-phenyl)-9-methyl-2-piperazin-1-yl-thieno[2,3-d:4,5-d']dipyrimidine 4-Ethoxy-7-(4-[2-furyl]-phenyl)-9-methyl-2-piperazin-1-yl-thieno[2,3-d:4,5-d']dipyrimidine 4-Ethoxy-9-methyl-2-piperazin-1-yl-7-(4-[3-pyridyl]-phenyl)-thieno[2,3-d:4,5-d']dipyrimidine 4-Ethoxy-9-methyl-2-piperazin-1-yl-7-(4-[4-pyridyl]-phenyl)-thieno[2,3-d:4,5-d']dipyrimidine 7-(4'-Aminobiphen-4-yl)-4-ethoxy-9-methyl-2-piperazin-1-yl-thieno[2,3-d:4,5-d']dipyrimidine 4-Ethoxy-9-methyl-2-piperazin-1-yl-7-(3',4',5'-trimethoxy-biphen-4-yl)-thieno[2,3-d:4,5-d']dipyrimidine 4-Ethoxy-9-methyl-7-(4-phenoxy-phenyl)-2-piperazin-1-yl-thieno[2,3-d:4,5-d']dipyrimidine 2'-Amino-4-(4-ethoxy-9-methyl-2-piperazin-1-yl-thieno[2,3-d:4,5-d']dipyrimidin-7-yl)-biphenyl-4'-carboxylic acid methyl ester 7-(3',4'-Dimethoxybiphen-4-yl)-4-ethoxy-9-methyl-2-piperazin-1-yl-thieno[2,3-d:4,5-d']dipyrimidine formula 1(c) or 1(d), which are explicitly:

10-Ethoxy-5-morpholino-8-piperazin-1-yl-pyrimido[4',5':4,5]thieno[2,3-c]-1,2,3,4-tetrahydro-isoquinoline 7-Ethoxy-2,3-dihydro-4-morpholino-9-piperazin-1-yl-1H-cyclopenta[4',5']pyrido[3',2':4,5]thieno[3,2-d]pyrimidine 8-Ethoxy-5-piperidino-10-piperazin-1-yl-pyrimido[4',5':4,5]thieno[2,3-c]-1,2,3,4-tetrahydro-isoquinoline-hydrochloride 8-Ethoxy-5-morpholino-10-piperazin-1-yl-pyrimido[4',5':4,5]thieno[2,3-c]-1,2,3,4-tetrahydro-isoquinoline-hydrochloride 8-Ethoxy-5-phenyl-10-piperazin-1-yl-pyrimido[4',5':4,5]thieno[2,3-c]-1,2,3,4-tetrahydro-isoquinoline-hydrochloride 10-Ethoxy-5-phenyl-8-piperazin-1-yl-pyrimido[4',5':4,5]thieno[2,3-c]-1,2,3,4-tetrahydro-isoquinoline 8-Ethoxy-5-morpholino-10-piperazin-1-yl-pyrimido[4',5':4,5]thieno[2,3-c]-1,2,3,4-tetrahydro-isoquinoline 7-Ethoxy-2,3,4,5-tetrahydro-4-morpholino-9-piperazin-1-yl-1H-cyclohepta[4',5']pyrido[3',2':4,5]thieno[3,2-d]pyrimidine The invention is further described by the below examples.

EXAMPLES

Example 1

Synthesis of 4-ethoxy-9-methyl-7-(4-iso-propoxy-phenyl)-2-piperazin-1-yl-thieno[2,3-d:4,5-d']dipyrimidine

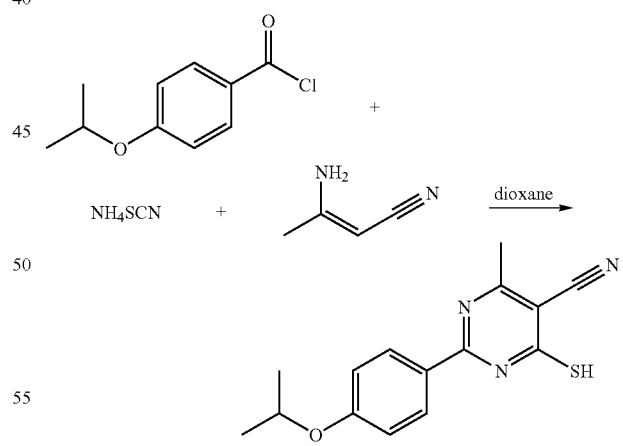

5.5 g (28 mmol) 4-iso-oropoxybenzoyl chloride and 2.5 g (33 mmol) ammonium thiocyanate are suspended in 100 ml dioxane and refluxed for 15 min. Then, 3.0 g (36 mmol) (E/Z)-3-amino-crotonic acid nitrile is added. The reaction mixture is refluxed for 3 h. Thereafter, the mixture is mixed with 500 ml ice water and allowed to stand overnight, subsequently filtrated and dried. 7.3 g (92%) 6-mercapto-4-methyl-2-(4-iso-propoxy-phenyl)-pyrimidine-5-carbonitrile is obtained.

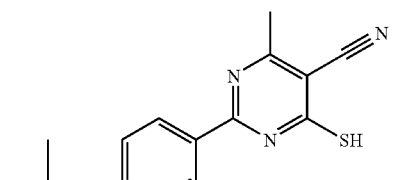

+

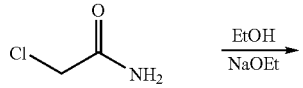

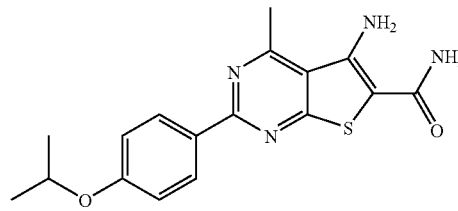

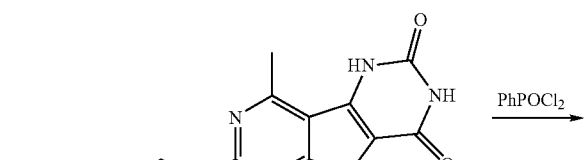

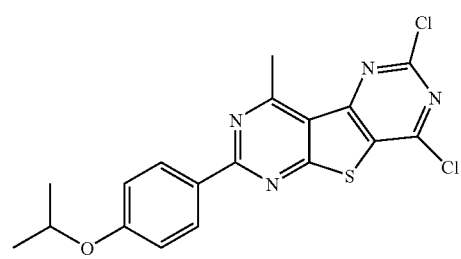

4.0 g (14 mmol) 6-mercapto-4-methyl-2-(4-iso-propoxy-phenyl)-pyrimidine-5-carbonitrile and 1.6 g (17 mmol) 2-chloroacetamide are suspended in 100 ml ethanol and 1.9 g (28 mmol) sodium ethylate is admixed. The reaction mixture is refluxed for 3 h. It is filtrated, washed with ethanol and water and dried. 1.5 g (31%) 5-amino-4-methyl-2-(4-iso-propoxy-phenyl)-thieno[2,3-d]pyrimidine-6-carboxamide is obtained.

1.0 g (2.7 mmol) 9-methyl-7-(4-iso-propoxy-phenyl)-thieno[2,3-d:4,5-d']dipyrimidine-2,4(1H,3H)-dione and 2.3 ml (16.3 mmol) dichlorophenylphosphine oxide are heated to 185° C. for 6 h. Having cooled down to room temperature, the mixture is poured onto 40 g ice water and neutralized with saturated sodium hydrogen carbonate solution. The precipitate is sucked off, washed with 300 ml water and dried. 0.9 g (82%) 2,4-dichloro-9-methyl-7-(4-iso-propoxy-phenyl)-thieno[2,3-d:4,5-d']dipyrimidine is obtained.

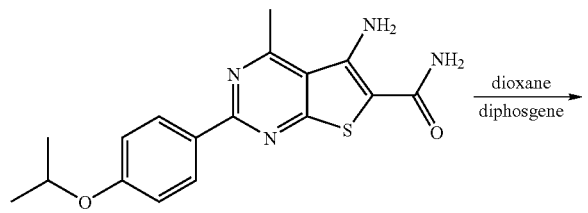

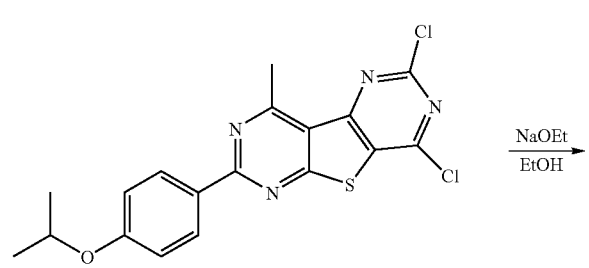

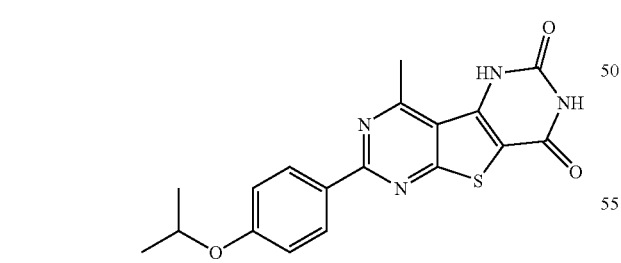

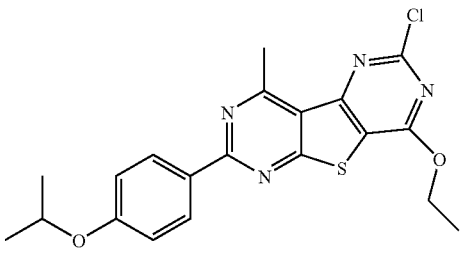

1.0 g (3 mmol) 5-amino-4-methyl-2-(4-iso-propoxy-phenyl)-thieno[2,3-d]pyrimidine-6-carboxamide was suspended in 200 ml dioxane, and following the addition of 0.73 ml (6 mmol) diphosgene the suspension is refluxed for 2 h. Having cooled down to room temperature, 20 ml water was carefully added and the precipitate was subsequently sucked off. 0.8 g (68%) 9-methyl-7-(4-iso-propoxy-phenyl)-thieno[2,3-d:4,5-d']-dipyrimidine-2,4(1H,3H)-dione is obtained.

0.9 g (2.2 mmol) 2,4-dichloro-9-methyl-7-(4-iso-propoxy-phenyl)-thieno[2,3-d:4,5-d']dipyrimidine is suspended in 50 ml ethanol and mixed with 0.46 g (6.7 mmol) sodium methylate. The mixture is stirred at room temperature for 4 h. Thereafter, the precipitate is sucked off, washed with ethanol and water and dried. Following flash chromatography (CH$_2$Cl$_2$) 0.47 g (51%) 2-chloro-4-ethoxy-9-methyl-7-(4-iso-propoxy-phenyl)-thieno[2,3-d:4,5-d']dipyrimidine is obtained.

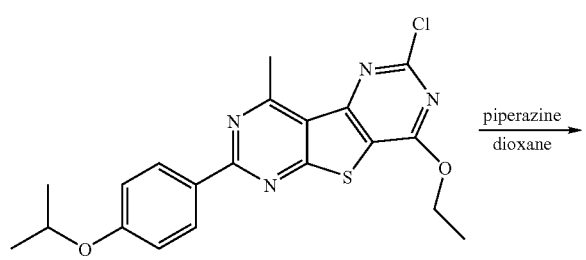

0.1 g (0.24 mmol) 2-chloro-4-ethoxy-9-methyl-7-(4-iso-propoxy-phenyl)-thieno[2,3-d:4,5-d']dipyrimidine and 83 mg (0.96 mmol) piperazine are refluxed in 40 ml dioxane for 4 h. Thereafter, the solvent is removed and the residue is suspended in water and sucked off. Following flash chromatography (chloroform/ethanol 10:2) 20 mg (18%) of the title substance is obtained.

The compounds prepared according to Example 1 are summarized in Table 1

TABLE 1

| Structure | M [g/mol] | MS (ESI) [m/z] | Melting point [° C.] | purity [%] |
|---|---|---|---|---|
| 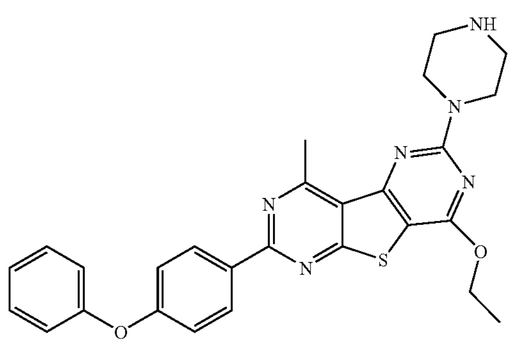 | 498.60 | 499 [M + H]$^+$ | 188-189 | >99 |
| 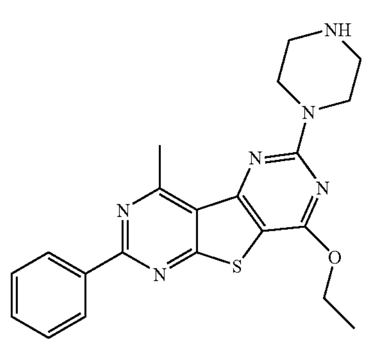 | 406.50 | 407 [M + H]$^+$ | 195 | 98 |

TABLE 1-continued
| Structure | M [g/mol] | MS (ESI) [m/z] | Melting point [° C.] | purity [%] |
|---|---|---|---|---|
| 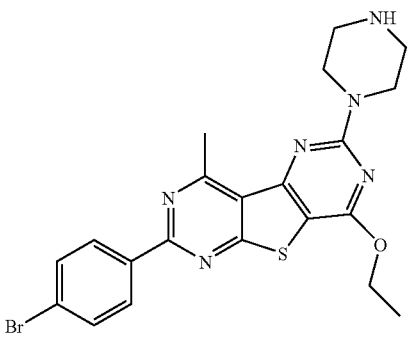 | 485.40 | 485, 487 [M + H]⁺ | 210-211 | 97 |
| 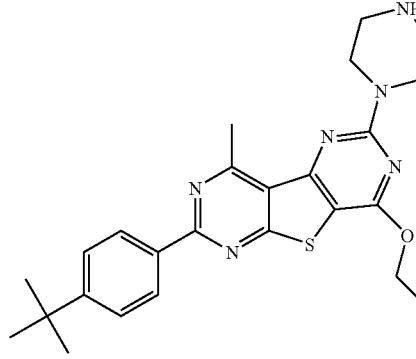 | 562.61 | 563 [M + H]⁺ | 144 | >99 |
| 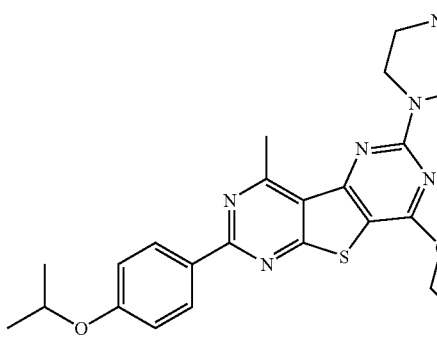 | 464.58 | 465 [M + H]⁺ | 194-195 | 98 |
| 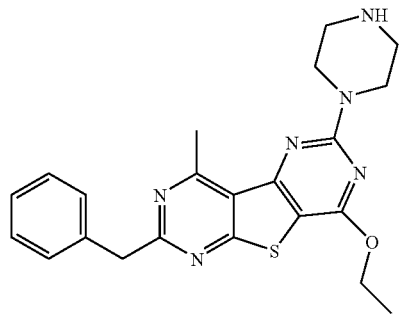 | 420.53 | 421 [M + H]⁺ | 170-171 | 98 |

TABLE 1-continued

| Structure | M [g/mol] | MS (ESI) [m/z] | Melting point [° C.] | purity [%] |
|---|---|---|---|---|
| 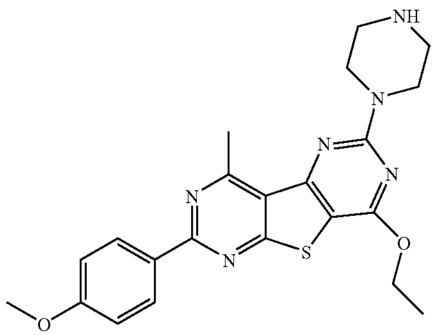 | 436.53 | 437 [M + H]+ | 179 | >99 |
| 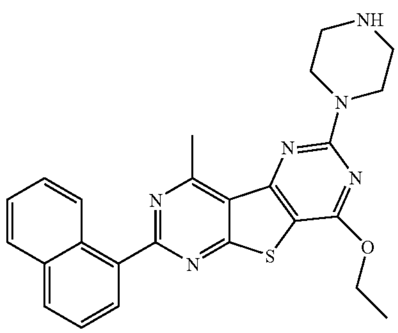 | 456.56 | 457 [M + H]+ | 148-149 | 98 |
| 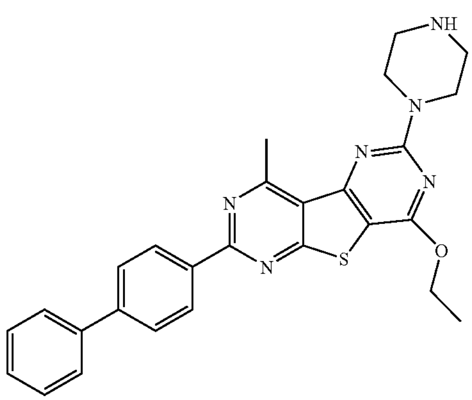 | 482.60 | 483 [M + H]+ | 217 | >99 |
| 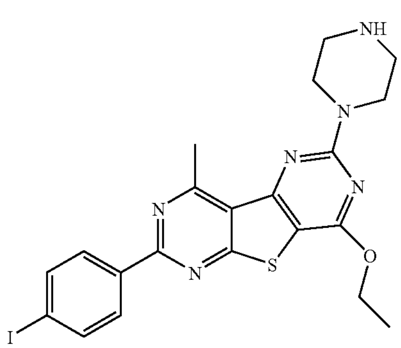 | 532.40 | 533 [M + H]+ | 273-276 | >99 |

Example 2

Synthesis of 2-ethoxy-9-methyl-4-piperazin-1-yl-7-phenyl-thieno[2,3-d:4,5-d']dipyrimidine

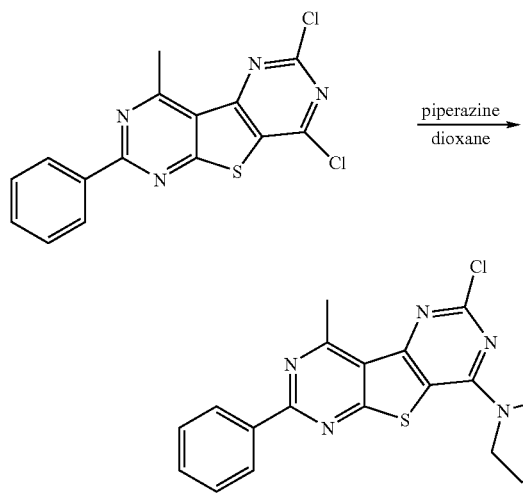

3.0 g (8.6 mmol) 2,4-dichloro-9-methyl-7-phenyl-thieno[2,3-d:4,5-d']dipyrimidine and 2.0 g (23.2 mmol) piperazine are added by stirring to 40 ml tetrahydrofuran at room temperature for 6 h. Thereafter, the solvent is removed, the residue is suspended in water, sucked off, washed with 40 ml water and dried. 1.5 g (44%) 2-chloro-9-methyl-4-piperazin-1-yl-7-phenyl-thieno[2,3-d:4,5-d']dipyrimidine is obtained.

1.30 g (3.3 mmol) 2-chloro-9-methyl-4-piperazin-1-yl-7-phenyl-thieno[2,3-d:4,5-d']di-pyrimidine and 0.67 g (9.9 mmol) sodium ethylate are refluxed in 30 ml ethanol for 3 h. Thereafter, the solvent is removed and the residue is suspended in some water. The aqueous suspension is extracted with dichloromethane and the solvent is removed. 0.90 g (68%) of the title substance is obtained. ESI-MS [m/z]: 407, melting point: >310° C.

Example 3

Synthesis of 7-(4-[3'-aminobiphenyl)-4-ethoxy-9-methyl-2-piperazin-1-yl-thieno[2,3-d:4,5-d']dipyrimidine

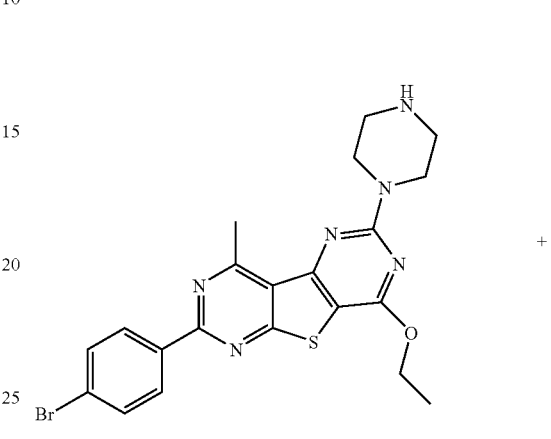

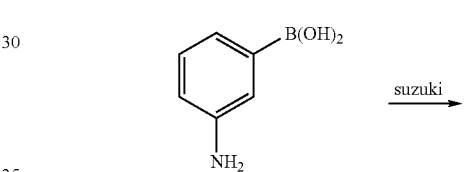

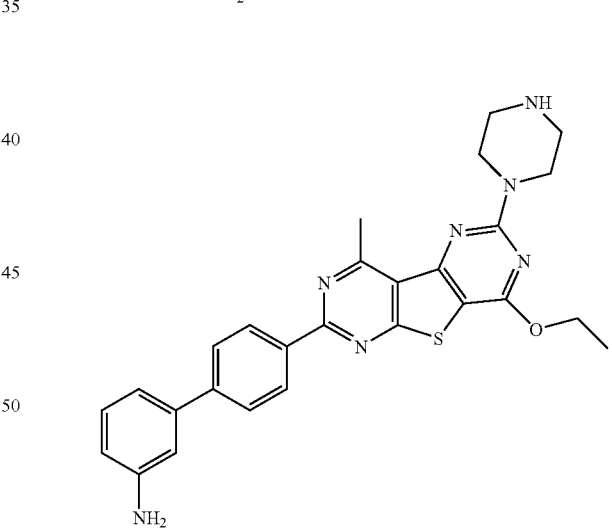

0.20 g (0.41 mmol) 7-(4-bromophenyl)-4-ethoxy-9-methyl-2-piperazin-1-yl-thieno[2,3-d:4,5-d']dipyrimidine (prepared in analogy to Example 1), 0.09 g (0.67 mmol) 3-aminophenylboronic acid and 1 ml 1 M $Cs_2CO_3$ were suspended in 50 ml isopropanol/toluene (1:4), degassed with nitrogen for 15 min. Then, 10 mg tetrakis(triphenyl)phosphine)palladium was admixed under a nitrogen atmosphere and the mixture was held at 100° C. by means of a microwave oven (130 W) for 3 h. Flash chromatographic purification (chloroform/methanol, 8.5:1.5) supplied 150 mg (73%) of the title substance.

The following compounds were obtained according to Example 3 (Table 2)

TABLE 2

| Structure | M [g/mol] | MS (ESI) [m/z] | Melting point [° C.] | purity [%] |
|---|---|---|---|---|
| 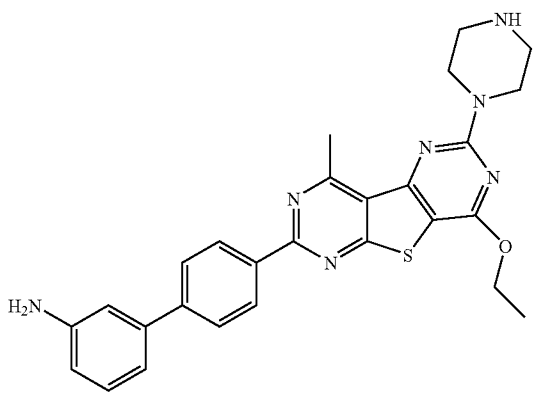 | 497.61 | 498 [M + H]⁺ | 225 | >99 |
| | 472.56 | 473 [M + H]⁺ | 250-251 | >99 |
| | 472.56 | 473 [M + H]⁺ | 220-221 | 98 |

TABLE 2-continued

| Structure | M [g/mol] | MS (ESI) [m/z] | Melting point [° C.] | purity [%] |
|---|---|---|---|---|
| | 483.59 | 484 [M + H]⁺<br>242 [M + 2H]²⁺ | >300 | >99 |
| | 483.59 | 484 [M + H]⁺<br>242 [M + 2H]²⁺ | 227 | >99 |
| 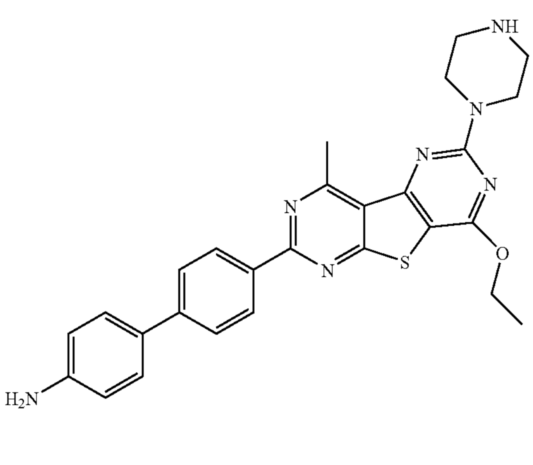 | 497.61 | 498 [M + H]⁺<br>250 [M + 2H]²⁺ | >300 | >99 |

TABLE 2-continued

| Structure | M [g/mol] | MS (ESI) [m/z] | Melting point [° C.] | purity [%] |
|---|---|---|---|---|
| 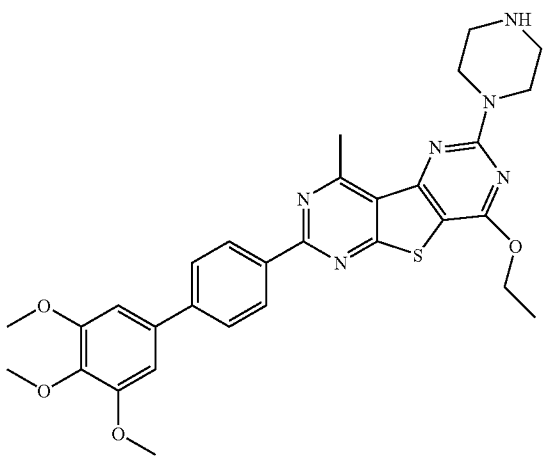 | 572.68 | 573 [M + H]⁺ | n.d. | >99 |
| 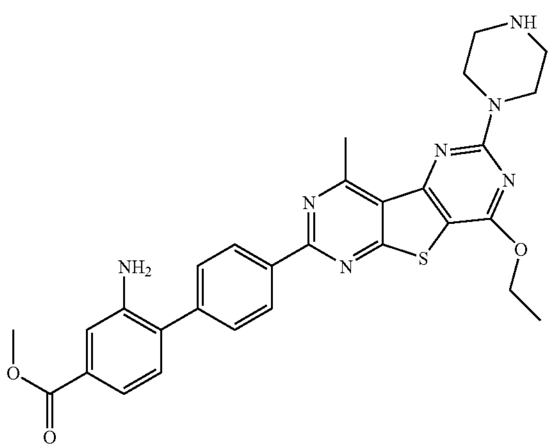 | 555.65 | 556 [M + H]⁺ 279 [M + 2H]²⁺ | 208-209 | 98 |
| 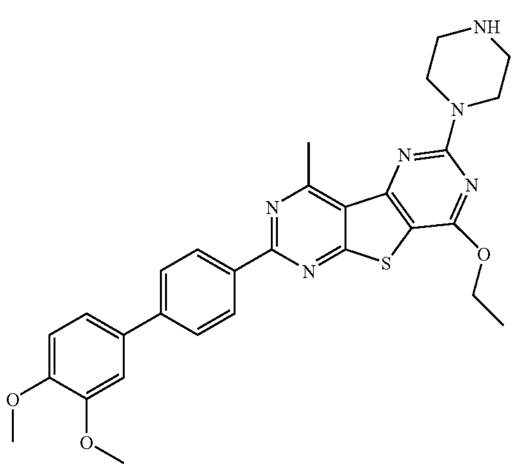 | 542.65 | 543 [M + H]⁺ | 210-211 | 97 |

TABLE 2-continued

| Structure | M [g/mol] | MS (ESI) [m/z] | Melting point [° C.] | purity [%] |
|---|---|---|---|---|
| 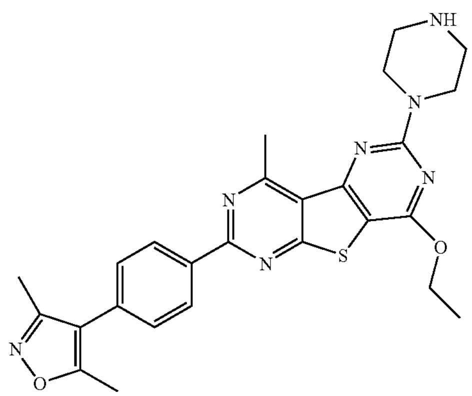 | 501.60 | 502 [M + H]⁺ | n.d. | >99 |
| 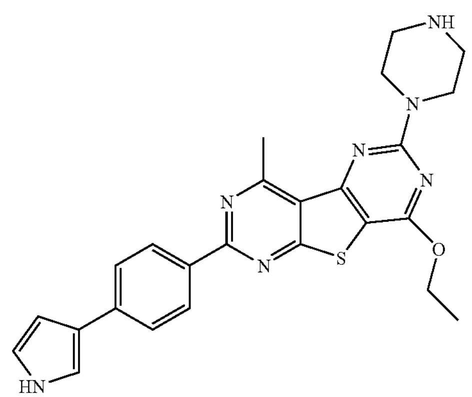 | 471.58 | 472 [M + H]⁺ | >300 | 98 |
| 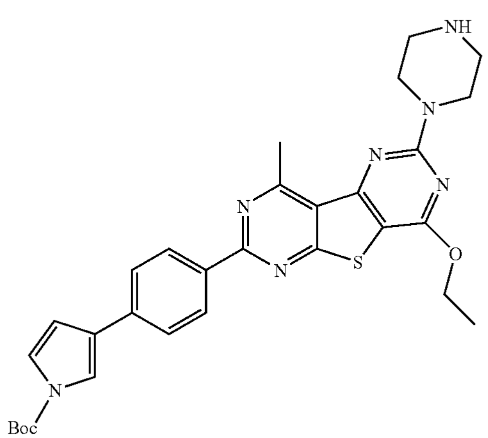 | 571.69 | 572 [M + H]⁺ | 179 | >99 |

TABLE 2-continued

| Structure | M [g/mol] | MS (ESI) [m/z] | Melting point [° C.] | purity [%] |
| --- | --- | --- | --- | --- |
| 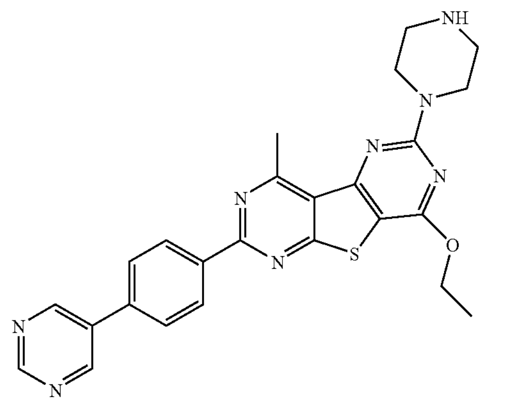 | 484.58 | 485 [M + H]+ 243 [M + 2H]2+ | 246 | >99 |
| 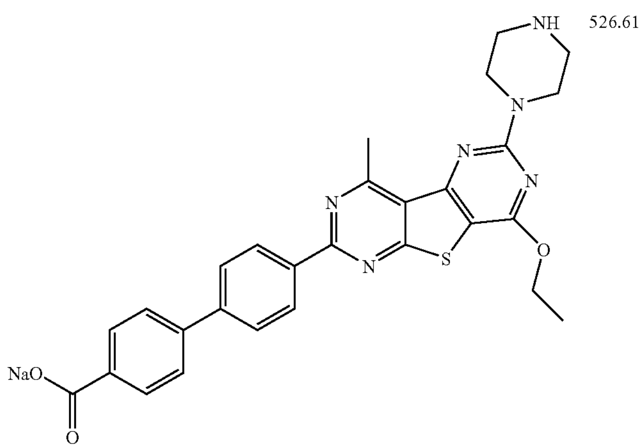 | 526.61 | 527 [M + H]+ | 267-269 | 95 |
| 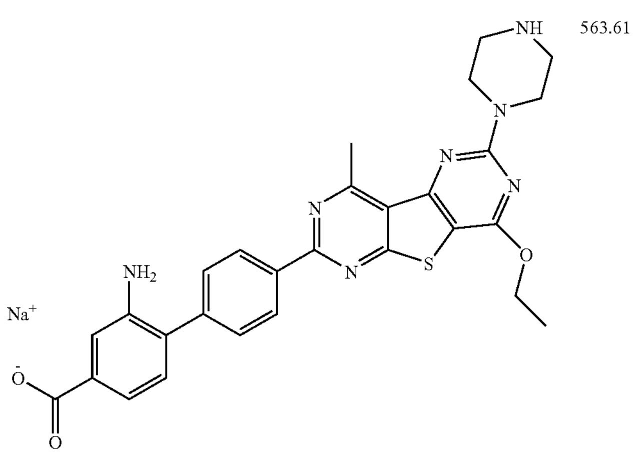 | 563.61 | 542 [M + H]+ | >300 | 98 |

TABLE 2-continued
| Structure | M [g/mol] | MS (ESI) [m/z] | Melting point [° C.] | purity [%] |
|---|---|---|---|---|
| 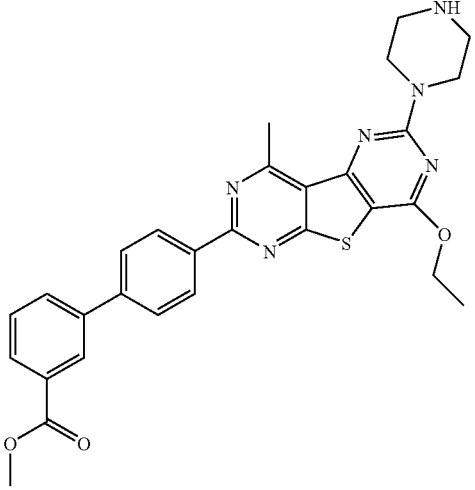 | 540.64 | 541 [M + H]⁺ | 239 | >99 |
| 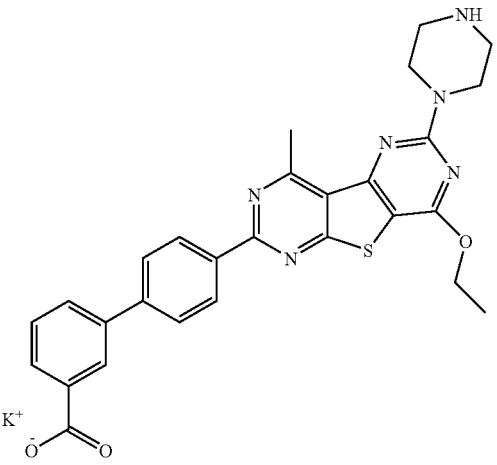 | 564.70 | 527 [M + H]⁺ | >300 | >99 |
| 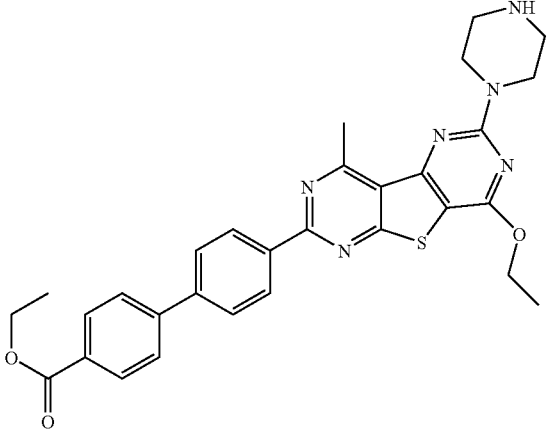 | 554.66 | 555 [M + H]⁺ | 211 | >99 |

Example 4

Synthesis of 4-ethoxy-9-methyl-2-piperazin-1-yl-7-(4-vinyl-phenyl)-thieno[2,3-d:4,5-d']dipyrimidine

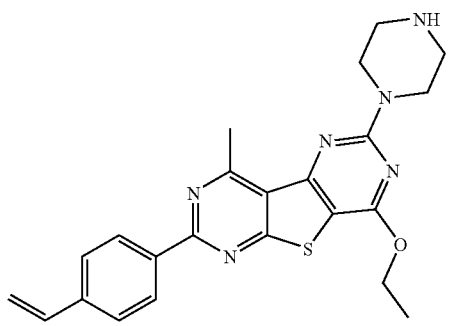

The title substance was prepared by coupling 7-(4-bromophenyl)-4-ethoxy-9-methyl-2-piperazin-1-yl-thieno[2,3-d:4,5-d']dipyrimidine with 2,4,6-trivinylcyclotriboroxane-pyridine complex in analogy to Example 3. ESI-MS [m/z]: 433, melting point: 165-166° C.

Example 5

Synthesis of 7-(4-[1,2-dihydroxyethyl]-phenyl)-4-ethoxy-9-methyl-2-piperazin-1-yl-thieno[2,3-d:4,5-d']dipyrimidine

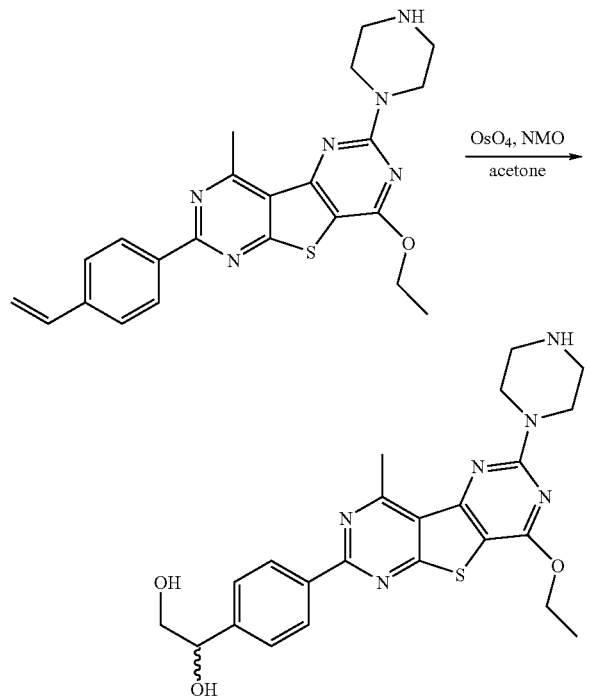

0.20 g (0.46 mmol) 4-ethoxy-9-methyl-2-piperazin-1-yl-7-(4-vinylphenyl)-thieno[2,3-d:4,5-d']dipyrimidine and 0.16 g (1.39 mmol) N-methylmorpholine-N-oxide-monohydrate were dissolved in 50 ml acetone. Then, 0.3 ml (4% aqueous) OsO₄ solution was added and stirring was carried out at room temperature for 24 h. Thereafter, 100 ml 1 M NaCO₃ solution were added and extraction with dichloromethane was carried out. Following flash chromatographic purification (chloroform/methanol, 8.5:1.5) 100 mg (46%) of the title compound is obtained. ESI-MS [m/z]: 466, melting point: >300° C.

Example 6

Synthesis of 4-ethoxy-7-(4-[{2E,4E}-1-hydroxy-hexa-2,4-dienyl]phenyl)-9-methyl-2-piperazin-1-yl-thieno[2,3-d:4,5-d']dipyrimidine

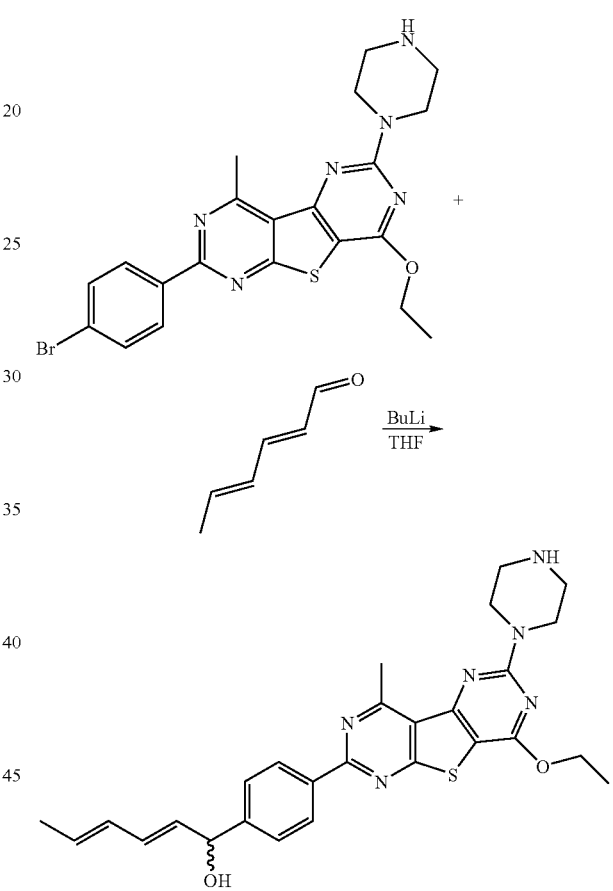

200 mg (0.4 mmol) 7-(4-bromophenyl)-4-ethoxy-9-methyl-2-piperazin-1-yl-thieno[2,3-d:4,5-d']dipyrimidine was mixed at −80° C. in 50 ml THF with 0.48 ml (1.2 mmol) 2.5 M BuLi solution. After 15 min at this temperature, 112 mg (1.2 mmol) (2E,4E) hexadienal was added. Subsequently, the reaction mixture was heated to −10° C. and the reaction was terminated by addition of 10 ml saturated NaHCO₃. The organic solvent was removed and the aqueous phase was extracted with CH₂Cl₂. Following flash chromatographic purification (CH₂Cl₂/methanol, 8:2) 130 mg (63%) of the title compound was obtained. ESI-MS [m/z]: 503, melting point: 149-150° C.

The following compound was prepared analogously:

4-Ethoxy-7-(4-[hydroxy{pyridin-3-yl}methyl]-phenyl)-9-methyl-2-piperazin-1-yl-thieno[2,3-d:4,5-d']dipyrimidine

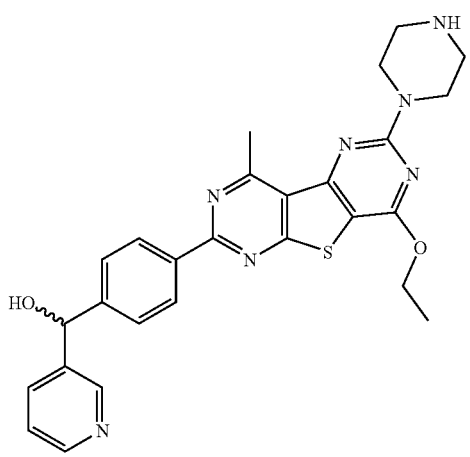

ESI-MS [m/z]: 514, melting point: 170-171° C.

Example 7

Synthesis of 7-(4-n-butoxy-phenyl)-4-ethoxy-9-methyl-2-piperazin-1-yl-thieno[2,3-d:4,5-d']dipyrimidine

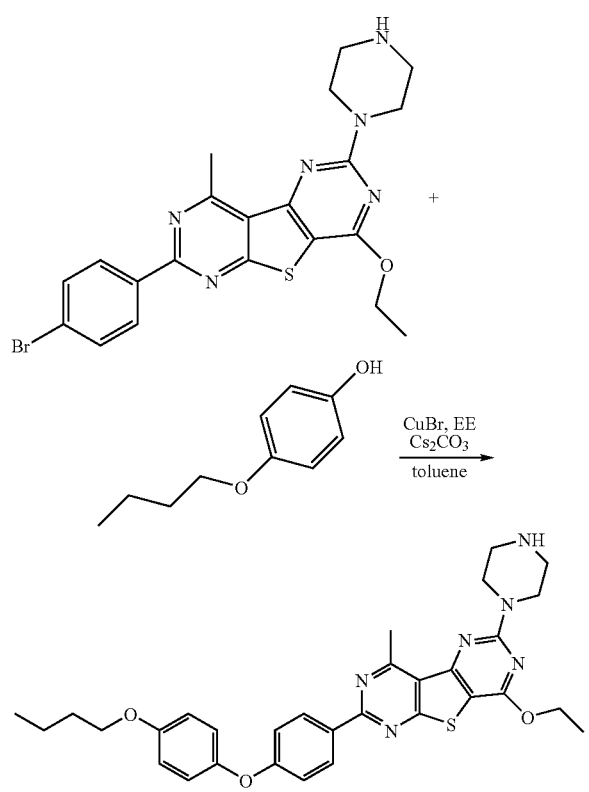

100 mg (0.21 mmol) 7-(4-bromophenyl)-4-ethoxy-9-methyl-2-piperazin-1-yl-thieno[2,3-d:4,5-d']dipyrimidine, 51 mg (0.31 mmol) 4-n-butoxyphenol, 134 mg (0.41 mmol) $Cs_2CO_3$, 1 μl (5 mole %) ethyl acetate and 1.5 mg (5 mole %) CuBr were suspended in 5 ml absolute toluene and heated in a microwave oven at 180° C. for 17 h. Thereafter, the solvent was removed and the residue was purified by means of flash chromatography. 4 mg (3%) of the title substance is obtained. ESI-MS [m/z]: 571

Example 8

Synthesis of 8-ethoxy-5-morpholino-10-piperazin-1-yl-pyrimido-[4',5':4,5]-thieno[2,3-c]-1,2,3,4-tetrahydro-isoquinoline

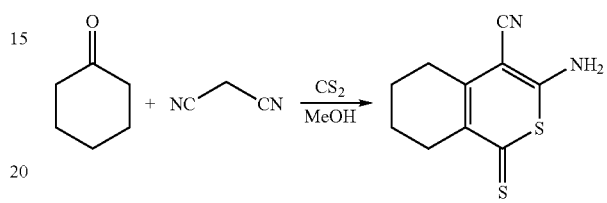

A solution of 19.60 g (0.2 mol) cyclohexanone, 13.20 g (0.2 mol) malonic acid dinitrile, 60 ml carbon disulfide and 60 ml methanol was admixed dropwise with 12.0 ml triethylamine. The solution was stirred at room temperature for 24 h, the product precipitating as an orange crystalline precipitate. This step was followed by filtration, washing with methanol and drying. 32 g (72%) 3-amino-1-thioxo-5,6,7,8-tetrahydro-1H-isothiocumarin-4-carbonitrile is obtained.

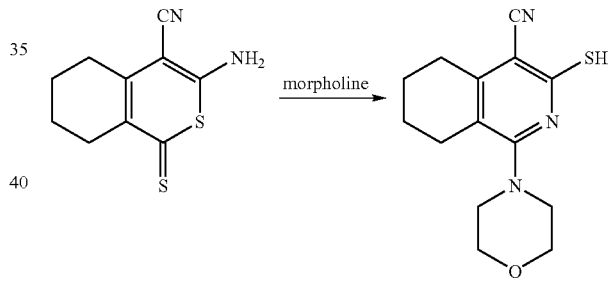

22.23 g (0.1 mol) 3-amino-1-thioxo-5,6,7,8-tetrahydro-1H-isothiocumarin-4-carbonitrile was suspended in 100 ml morpholine and heated to 100° C. bath temperature until the $H_2S$ development was terminated (4-6 h). Having cooled down, the reaction mixture was filtrated, washed with ethanol and dried. 23 g (83%) 3-mercapto-1-morpholino-5,6,7,8-tetrahydroisoquinoline-4-carbonitrile was obtained.

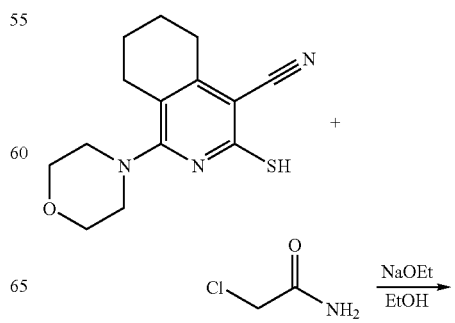

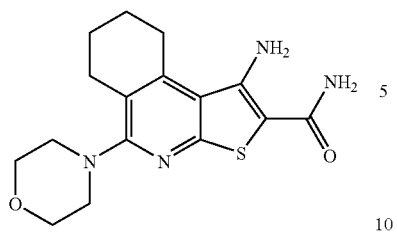

4.00 g (20 mmol) 3-mercapto-1-morpholino-5,6,7,8-tetrahydroisoquinoline-4-carbonitrile and 1.80 g (20 mmol) 2-chloroacetamide are suspended in 50 ml ethanol and mixed with 1.50 g (40 mmol) sodium ethylate. The reaction mixture is refluxed for 3 h. The product is filtrated and washed with ethanol, water and dried. 4.00 g (80%) 1-amino-5-morpholino-thieno[2,3-c]-6,7,8,9-tetrahydro-isoquinoline-2-carboxamide amide is obtained.

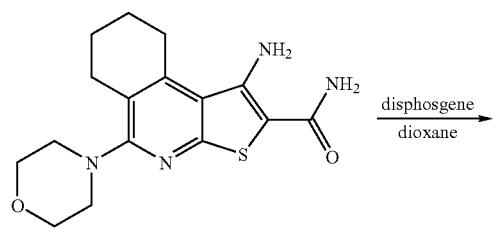

3.0 g (9 mmol) 1-amino-5-morpholino-thieno[2,3-c]-6,7,8,9-tetrahydro-isoquinoline-2-carboxamide is suspended in 100 ml dioxane, then 1.10 ml (8 mmol) chloroformic acid-trichloromethylester is added and refluxed for 3 h. The precipitate is filtrated and dried. 3.0 g (93%) 5-morpholino-pyrimido[4',5':4,5]thieno[2,3-c]-1,2,3,4-tetrahydro-isoquinoline-8,10-(9H,11H)-dione is obtained.

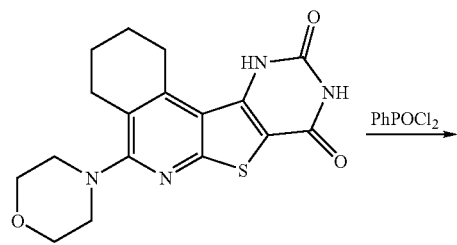

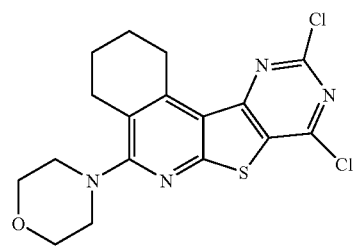

3.0 g (8 mmol) 5-morpholino-pyrimido[4',5':4,5]thieno[2,3-c]-1,2,3,4-tetrahydro-isoquinoline-8,10(9H,11H)-dione and 20 ml (140 mmol) dichlorophenylphosphineoxide are heated at 193° C. for 6 h. Then, the product is poured onto 40 g ice water and neutralized with saturated sodium hydrogen carbonate solution. The precipitate is sucked off, washed with 100 ml water and dried. 2.0 g (63%) 8,10-dichloro-5-morpholino-pyrimido[4',5':4,5]thieno[2,3-c]-1,2,3,4-tetrahydro-isoquinoline is obtained.

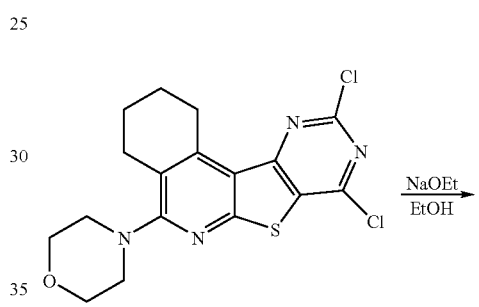

0.50 g (1 mmol) 8,10-dichloro-5-morpholino-pyrimido[4',5':4,5]thieno-[2,3-c]-1,2,3,4-tetrahydro-isoquinoline is suspended in 40 ml ethanol and mixed with 0.12 g (2 mmol) NaOEt. The mixture is stirred at room temperature for 24 h. Then, the precipitate is sucked off, washed with ethanol and dried. 3.9 g (96%) 10-chloro-8-ethoxy-5-morpholino-pyrimido[4',5':4,5]thieno[2,3-c]-1,2,3,4-tetrahydro-isoquinoline is obtained.

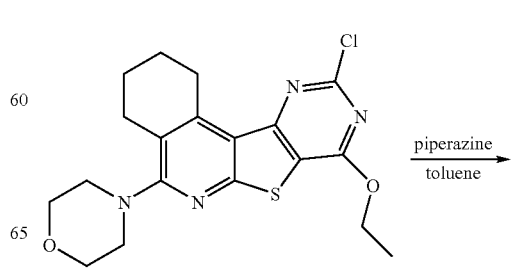

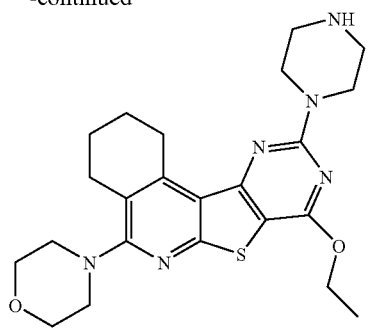

0.10 g (0.25 mmol) 10-chloro-8-ethoxy-5-morpholino-pyrimido[4',5':4,5]-thieno[2,3-c]-1,2,3,4-tetrahydro-isoquinoline and 0.12 g (1.4 mmol) piperazine are refluxed in 20 ml toluene for 4 h. Thereafter, the solvent is removed and the residue is suspended in dichloromethane. The organic phase is washed with saturated sodium carbonate solution, dried on sodium sulfate and the solvent is removed. The residue is purified by flash chromatography (chloroform/ethanol 10:2). 0.11 g (97%) of the title compound is obtained.

The following compounds were obtained according to Example 8 (Table 3)

TABLE 3

| Structure | M [g/mol] | ESI MS [m/z] | Melting point [° C.] |
|---|---|---|---|
| 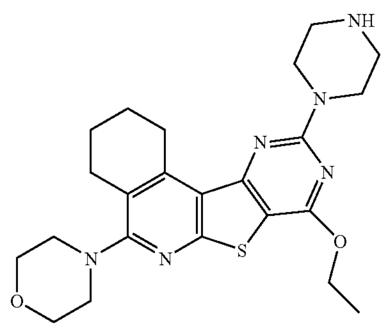 | 454.22 | 455 [M + H]$^+$ | 181-184 |
| 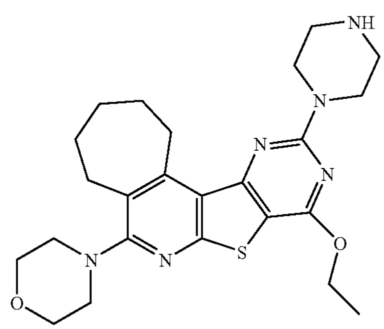 | 468.23 | 469 [M + H]$^+$ | 320 Zers. |
| 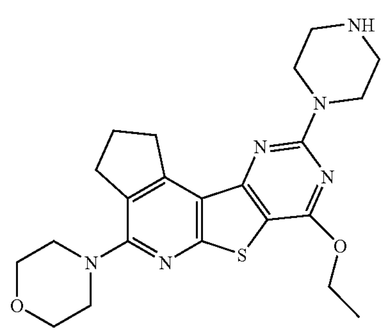 | 440.56 | 441 [M + H]$^+$ | 151-159 |

TABLE 3-continued

| Structure | MW | MS | Activity |
|---|---|---|---|
| (phenyl, morpholino, piperazinyl, ethoxy substituted pyrimido-thieno-pyridine) | 476.59 | 477 | 244 |
| (tetrahydroisoquinoline fused, N-methylpiperazinyl, piperazinyl, ethoxy substituted) | 467.63 | 468 | n.d. |
| (N-methyl tetrahydropyridine fused, morpholino, piperazinyl, ethoxy substituted) | 469.60 | 470 | n.d. |

Example 9

Synthesis of 10-ethoxy-5-morpholino-8-piperazin-1-yl-pyrimido[4',5':4,5]-thieno[2,3-c]-1,2,3,4-tetrahydro-isoquinoline 8,10-dichloro-5-morpholino-pyrimido[4',5':4,5]-thieno[2,3-c]-1,2,3,4-tetrahydro-isoquinoline piperazine / THF →

10-chloro-8-piperazin-1-yl-5-morpholino-pyrimido[4',5':4,5]-thieno[2,3-c]-1,2,3,4-tetrahydro-isoquinoline 0.30 g (0.76 mmol) 8,10-dichloro-5-morpholino-pyrimido[4',5':4,5]-thieno[2,3-c]-1,2,3,4-tetrahydro-isoquinoline and (1 mmol) piperazine are added by stirring to 40 ml tetrahydrofuran at room temperature for 6 h. Then, the solvent is removed, the residue is suspended in water, sucked off, washed with about 40 ml water and dried. 0.3 g (89%) 10-chloro-8-piperazin-1-yl-5-morpholino-pyrimido[4',5':4,5]-thieno-[2,3-c]-1,2,3,4-tetrahydro-isoquinoline is obtained.

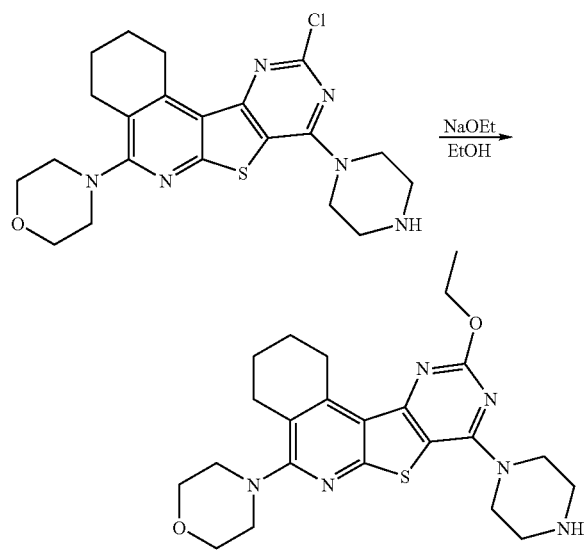

0.30 g (0.44 mmol) 10-chloro-8-piperazin-1-yl-5-morpholino-pyrimido-[4',5':4,5]thieno-[2,3-c]-1,2,3,4-tetrahydro-isoquinoline and 0.30 g (4.40 mmol) sodium methylate are refluxed in 10 ml ethanol for 3 h. Then, the solvent is removed and the residue is suspended in some water. The aqueous suspension is extracted in dichloromethane, the organic phase is dried on sodium sulfate and the solvent is removed. 0.21 g (97%) of the title substance is obtained. ESI-MS [m/z]: 455, melting point: 123-126

Example 10

Synthesis of 4-ethoxy-7-(3,4-dimethoxyphenyl)-9-methyl-2-piperazin-1-yl-pyrido[3',2':4,5]thieno[3,2-d]Pyrimidine

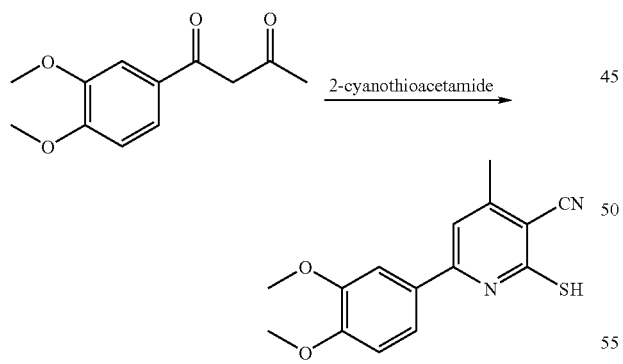

5.0 g (22.5 mmol) 1-(3,4-dimethoxyphenyl)butane-1,3-dione, 2.9 g (29.2 mmol) cyanthioacetamide and 4.0 g (29.2 mmol) potassium carbonate are added by stirring to 170 ml acetone at room temperature for 21 h. Then, the solvent is removed and the residue is just dissolved in ethanol/water (1:1). Following acidification with glacial acetic acid, the resulting precipitate is sucked off, washed with some water, suck dried and dried in vacuo at 50° C. 6.34 g (98%) 2-mercapto-6-(3,4-dimethoxyphenyl)-4-methyl-pyridine-3-carbonitrile is obtained.

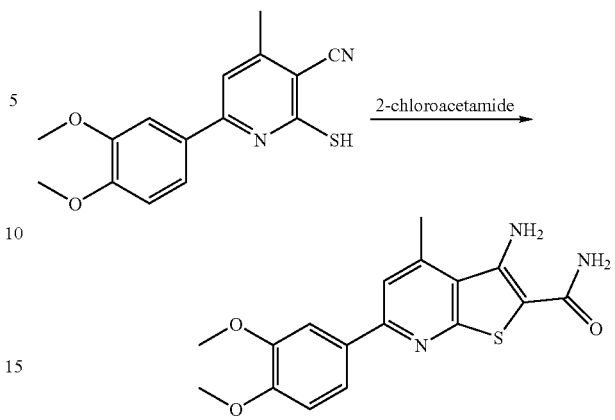

2.1 g (31.4 mmol) sodium ethylate are dissolved in 40 ml absolute ethanol. 3.0 g (10.5 mmol) 2-mercapto-6-(3,4-dimethoxyphenyl)-4-methyl-pyridine-3-carbonitrile and 1.2 g (12.6 mmol) 2-chloroacetamide are added and refluxed for 1 h. Following cooling, 10 ml water are added and the precipitate is sucked off, suck dried and dried in vacuo at 50° C. 3.4 g (94%) 3-amino-6-(3,4-dimethoxyphenyl)-4-methyl-thieno[2,3-b]-pyridine-2-carboxamide is obtained.

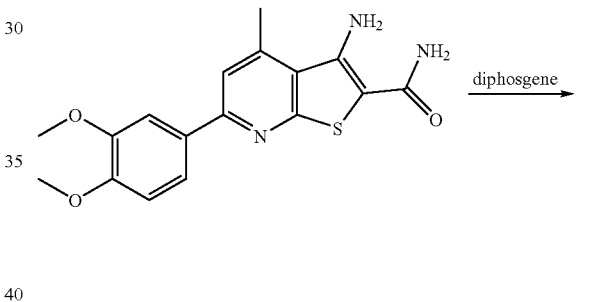

3.0 g (8.7 mmol) 3-amino-6-(3,4-dimethoxyphenyl)-4-methyl-thieno[2,3-b]pyridine-2-carboxamide is suspended in 100 ml absolute dioxane. Then, 1.1 ml (8.7 mmol) chloroformic acid trichloromethylester (diphosgene) is added and refluxed for 3 h. Following cooling, the precipitate is sucked off and then suspended in 50 ml water. The suspension is adjusted to pH 8 using concentrated ammonia solution and the precipitate is sucked off, washed with some water, suck dried and in vacuo at 50° C. 3.08 g (96%) 7-(3,4-dimethoxyphenyl)-9-methyl-pyrido[3',2':4,5]thieno[3,2-d]pyrimidine-2,4-dione is obtained.

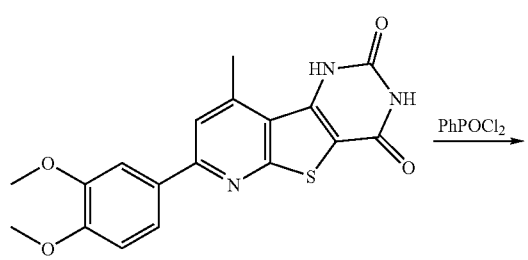

1.5 g (3.7 mmol) 2,4-dichloro-7-(3,4-dimethoxyphenyl)-9-methyl-pyrido[3',2':4,5]-thieno[3,2-d]pyrimidine and 0.7 g (11.1 mmol) sodium methylate are added by stirring to 50 ml absolute ethanol at room temperature for 24 h. Then, the precipitate is sucked off, washed with about 40 ml water, suck dried and dried in vacuo at 50° C. 1.38 g (90%) 2-chloro-4-ethoxy-7-(3,4-dimethoxyphenyl)-9-methyl-pyrido[3',2':4,5]-thieno[3,2-d]pyrimidine is obtained.

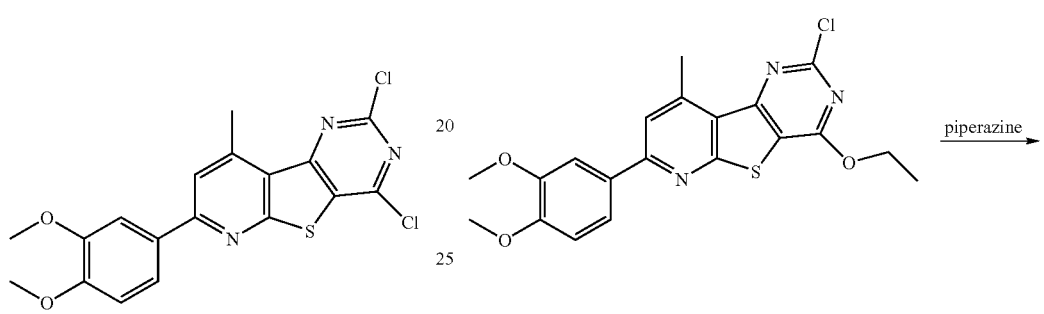

3.0 g (8.1 mmol) 7-(3,4-dimethoxyphenyl)-9-methyl-pyrido[3',2':4,5]-thieno[3,2-d]-pyrimidine-2,4-dione and 6.8 ml (48.7 mmol) dichloro-phenylphosphineoxide are heated at 200° C. for 6 h. The next step is pouring onto about 20 g ice water and neutralizing with saturated sodium hydrogen carbonate solution. The precipitate is sucked off, washed with about 100 ml water, suck dried and dried in vacuo at 50° C. 3.08 g (94%) 2,4-dichloro-7-(3,4-dimethoxyphenyl)-9-methyl-pyrido[3',2':4,5]thieno-[3,2-d]pyrimidine is obtained.

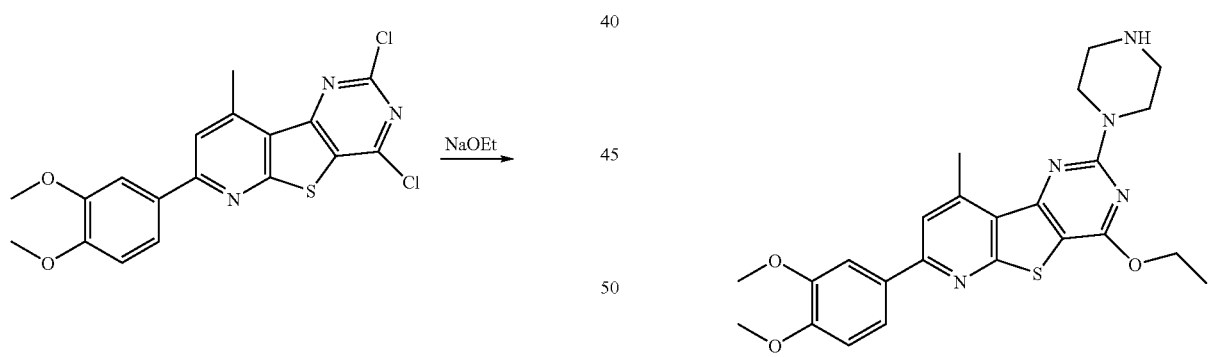

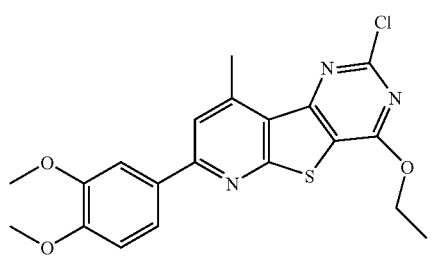

1.0 g (2.4 mmol) 2-chloro-4-ethoxy-7-(3,4-dimethoxyphenyl)-9-methyl-pyrido-[3',2':4,5]thieno[3,2-d]pyrimidine and 0.83 g (9.6 mmol) piperazine are refluxed in 20 ml toluene for 4 h. Then, the solvent is removed and the residue is suspended in dichloromethane. The organic phase is washed with saturated sodium carbonate solution, dried on sodium sulfate and the solvent is removed. The residue is purified by flash chromatography (ethanol/chloroform 1:5). 0.98 g (87%) of the title substance is obtained.

The following compounds were obtained according to Example 10 (Table 4)

TABLE 4

| Structure | M [g/mol] | ESI MS [m/z] [M + H]+ | Melting point [° C.] |
|---|---|---|---|
| 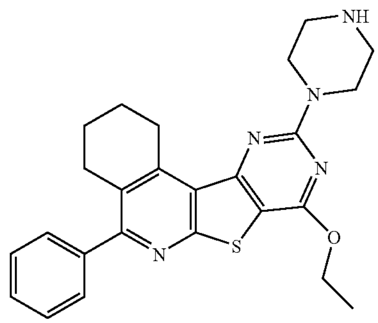 | 445.58 | 446 | 200-203 |
| 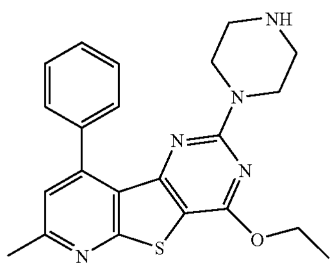 | 405.52 | 406 | n.d. |
| 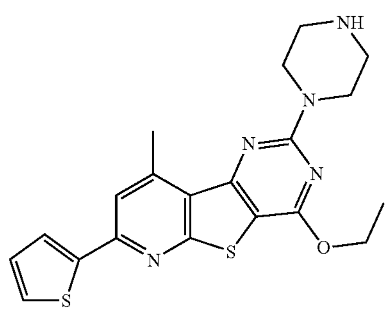 | 411.54 | 412 | n.d. |
| 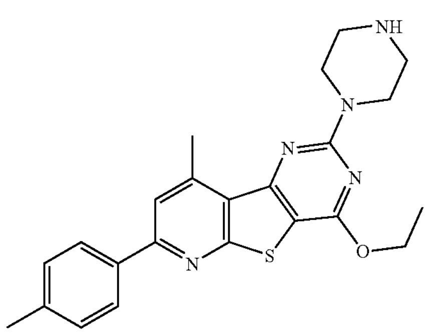 | 419.54 | 420 | n.d. |

TABLE 4-continued

| Structure | M [g/mol] | ESI MS [m/z] [M + H]+ | Melting point [° C.] |
|---|---|---|---|
| 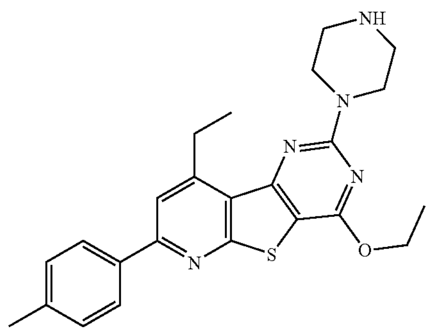 | 433.57 | 434 | n.d. |
| 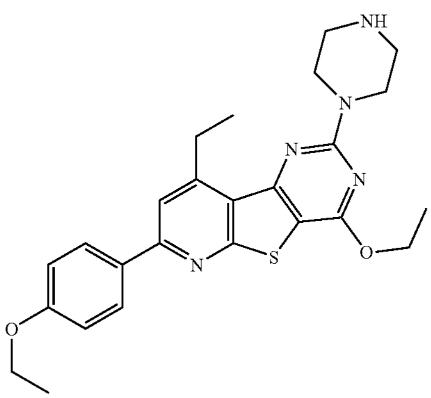 | 463.60 | 464 | n.d. |
| 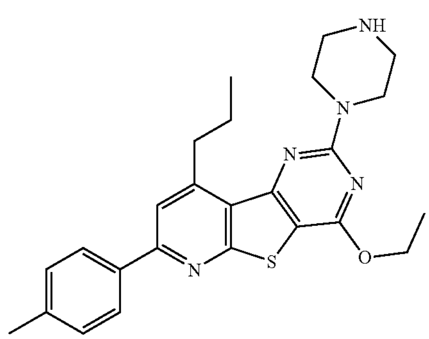 | 447.60 | 448 | n.d. |
| 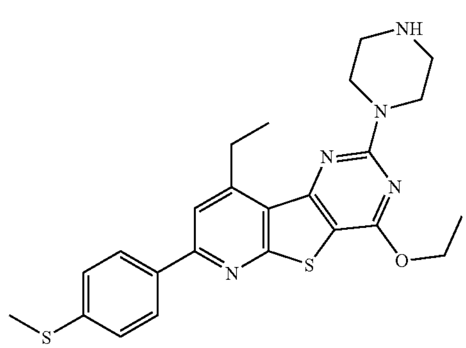 | 465.63 | 466 | n.d. |

TABLE 4-continued

| Structure | M [g/mol] | ESI MS [m/z] [M + H]⁺ | Melting point [° C.] |
|---|---|---|---|
| 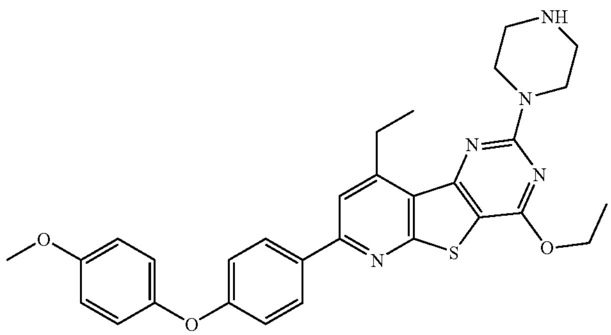 | 541.66 | 542 | 166 |
| 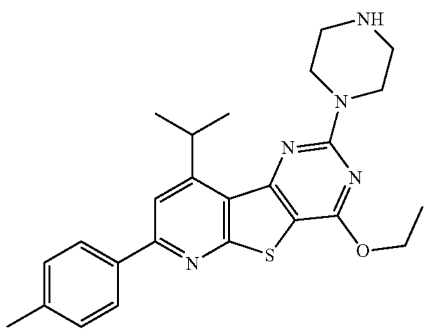 | 447.60 | 448 | n.d. |
| 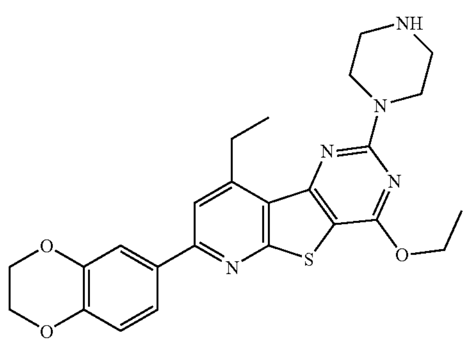 | 477.57 | 478 | n.d. |
| 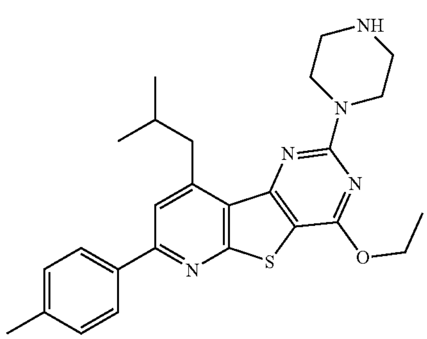 | 461.62 | 462 | n.d. |

TABLE 4-continued

| Structure | M [g/mol] | ESI MS [m/z] [M + H]+ | Melting point [° C.] |
|---|---|---|---|
| 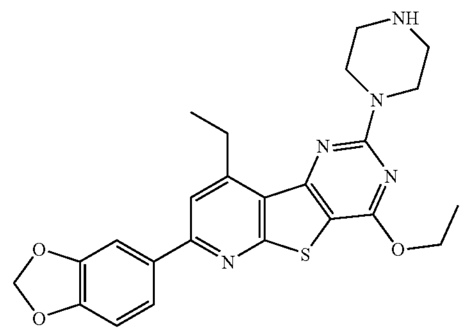 | 463.55 | 464 | n.d. |
| 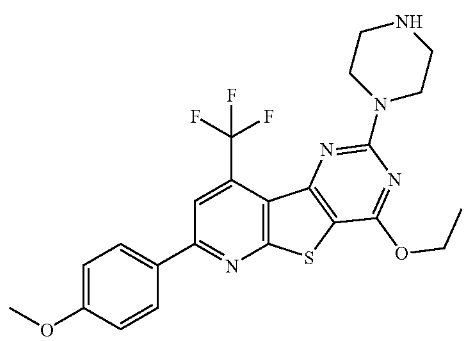 | 489.51 | 490 | n.d. |
| 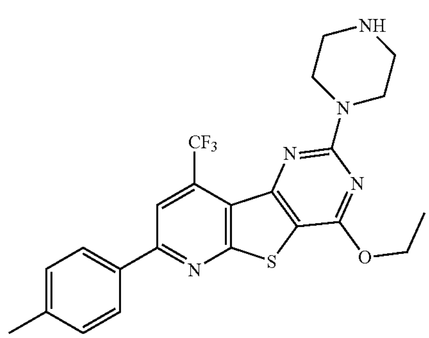 | 473.51 | 474 | n.d. |
| 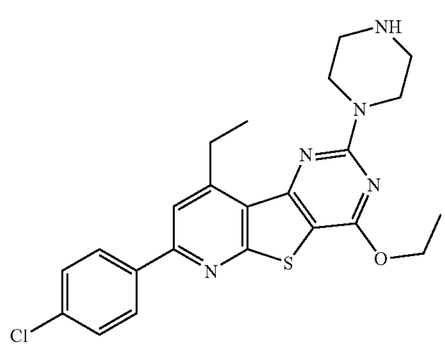 | 453.99 | 454 | n.d. |

TABLE 4-continued

| Structure | M [g/mol] | ESI MS [m/z] [M + H]+ | Melting point [° C.] |
|---|---|---|---|
| (structure with CF3, piperazine-NH, ethoxy, 2,3-dihydrobenzo[1,4]dioxine) | 517.52 | 518 | n.d. |
| (structure with CF3, piperazine-NH, ethoxy, 4-morpholinophenyl) | 544.59 | 545 | n.d. |
| (structure with CF3, piperazine-NH, ethoxy, 4-imidazol-1-yl-phenyl) | 525.55 | 526 | 216-222 |
| (structure with CF3, piperazine-NH, ethoxy, 4-ethoxycarbonylphenyl) | 531.60 | 532 | n.d. |

TABLE 4-continued

| Structure | M [g/mol] | ESI MS [m/z] [M + H]+ | Melting point [° C.] |
|---|---|---|---|
| (structure with CF3, piperazine, ethoxy, pyridine) | 460.47 | 461 | 185-187 |
| (structure with CF3, piperazine, ethoxy, benzoic acid) | 503.50 | 504 | n.d. |
| (structure with CF3, piperazine, ethoxy, piperidinyl-phenyl) | 542.62 | 543 | 204-205 |
| (structure with CF3, piperazine, ethoxy, pyrazine) | 461.46 | 462 | n.d. |

TABLE 4-continued
| Structure | M [g/mol] | ESI MS [m/z] [M + H]⁺ | Melting point [° C.] |
|---|---|---|---|
| 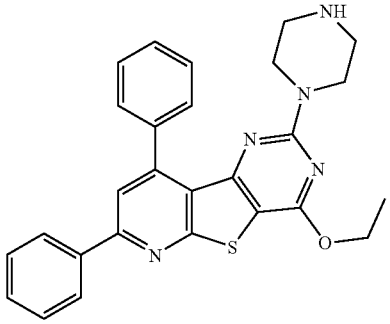 | 467.59 | 468 | 193-210 |
| 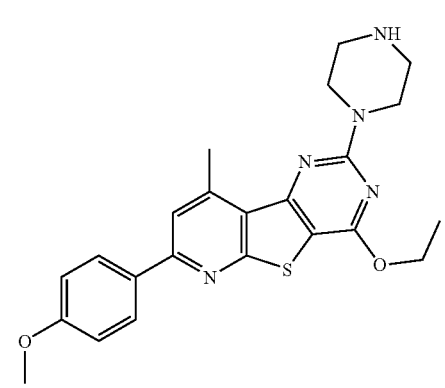 | 435.54 | 436 | 77-82 |
| 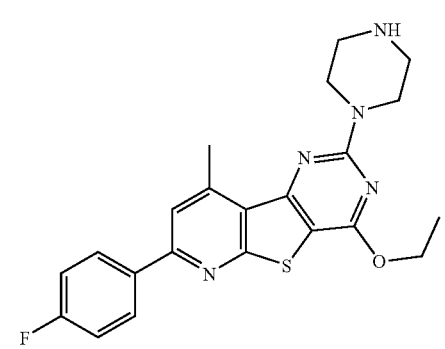 | 423.51 | 424 | 220 |
| 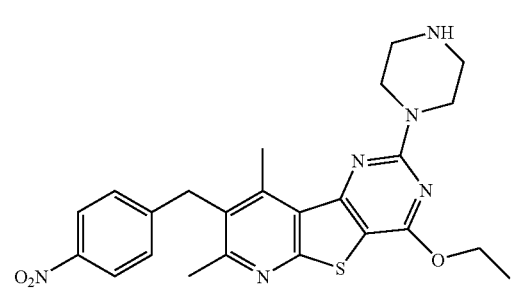 | 478.57 | 479 | 207-217 |

TABLE 4-continued

| Structure | M [g/mol] | ESI MS [m/z] [M + H]+ | Melting point [° C.] |
|---|---|---|---|
| 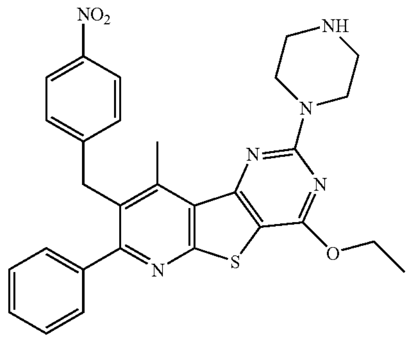 | 540.64 | 541 | n.d. |
| 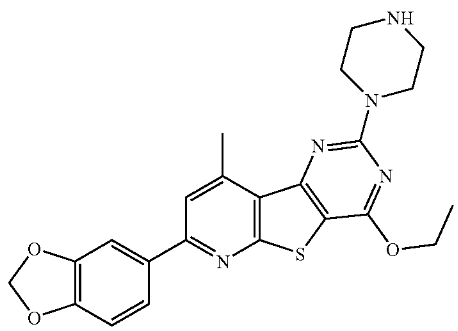 | 446.53 | 447 | n.d. |
| 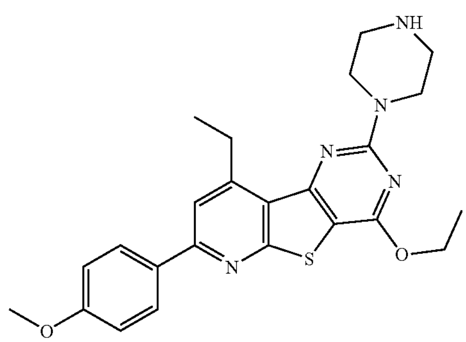 | 449.57 | 450 | n.d. |
| 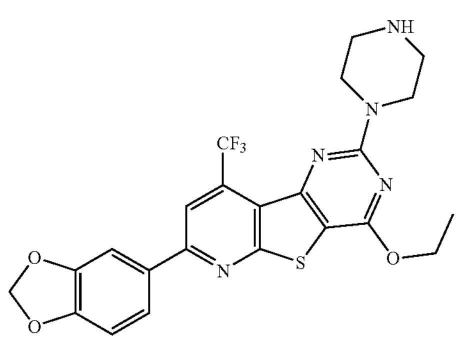 | 503.50 | 504 | n.d. |

TABLE 4-continued
| Structure | M [g/mol] | ESI MS [m/z] [M + H]+ | Melting point [° C.] |
|---|---|---|---|
| 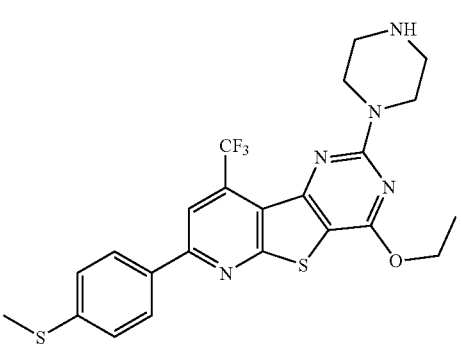 | 697.70 | 698 | 178-181 |
| 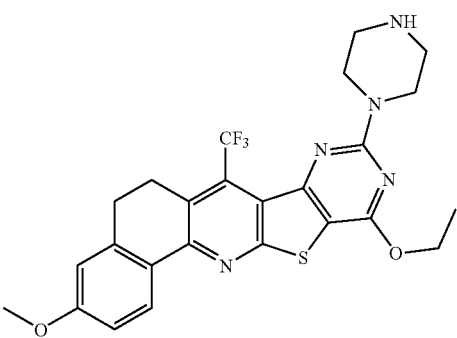 | 515.55 | 516 | n.d. |
| 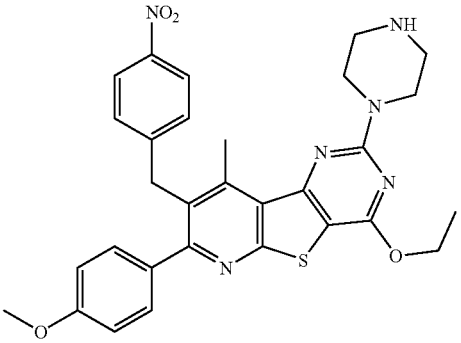 | 570.66 | 571 | n.d. |
| 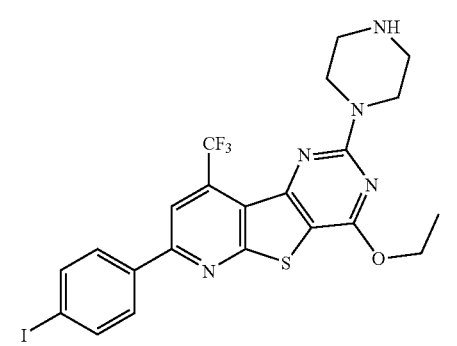 | 585.38 | 586 | 133 |

TABLE 4-continued

| Structure | M [g/mol] | ESI MS [m/z] [M + H]⁺ | Melting point [° C.] |
|---|---|---|---|
| (structure) | 465.57 | 466 | n.d. |
| (structure) | 504.48 | 505 | 229-233 |
| (structure) | 475.94 | 476 | n.d. |
| (structure) | 484.50 | 485 | n.d. |

TABLE 4-continued

| Structure | M [g/mol] | ESI MS [m/z] [M + H]+ | Melting point [° C.] |
|---|---|---|---|
| 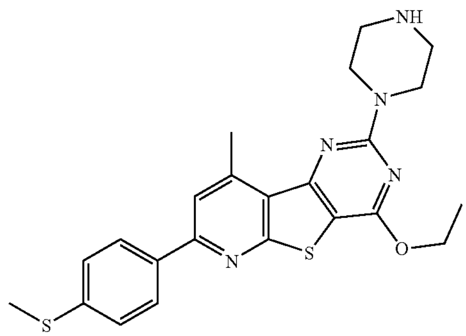 | 451.61 | 452 | n.d. |
| 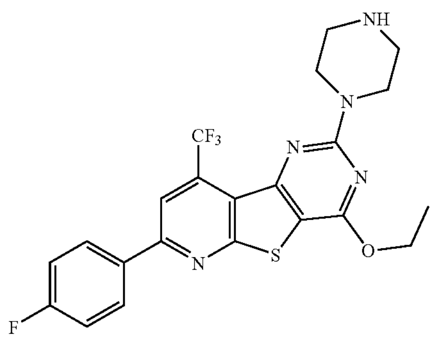 | 477.48 | 478 | n.d. |
| 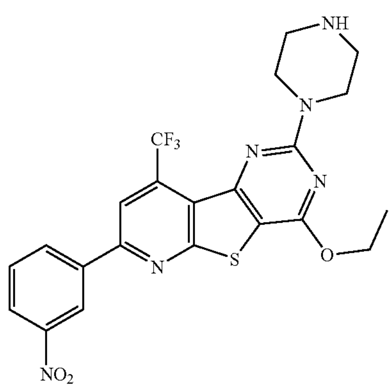 | 504.49 | 505 | n.d. |
| 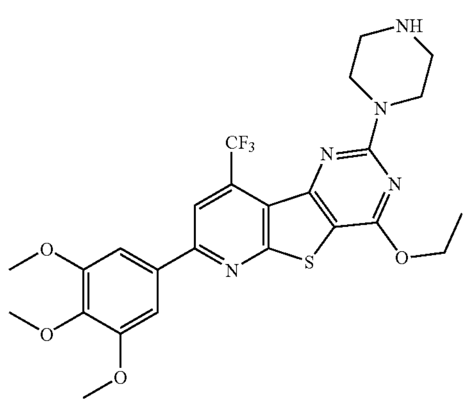 | 549.57 | 550 | n.d. |

TABLE 4-continued

| Structure | M [g/mol] | ESI MS [m/z] [M + H]+ | Melting point [° C.] |
|---|---|---|---|
| (structure) | 610.61 | 611 | n.d. |
| (structure) | 484.50 | 485 | n.d. |
| (structure) | 460.47 | 461 | 219-221 |
| (structure) | 460.47 | 461 | n.d. |

TABLE 4-continued

| Structure | M [g/mol] | ESI MS [m/z] [M + H]+ | Melting point [° C.] |
|---|---|---|---|
| 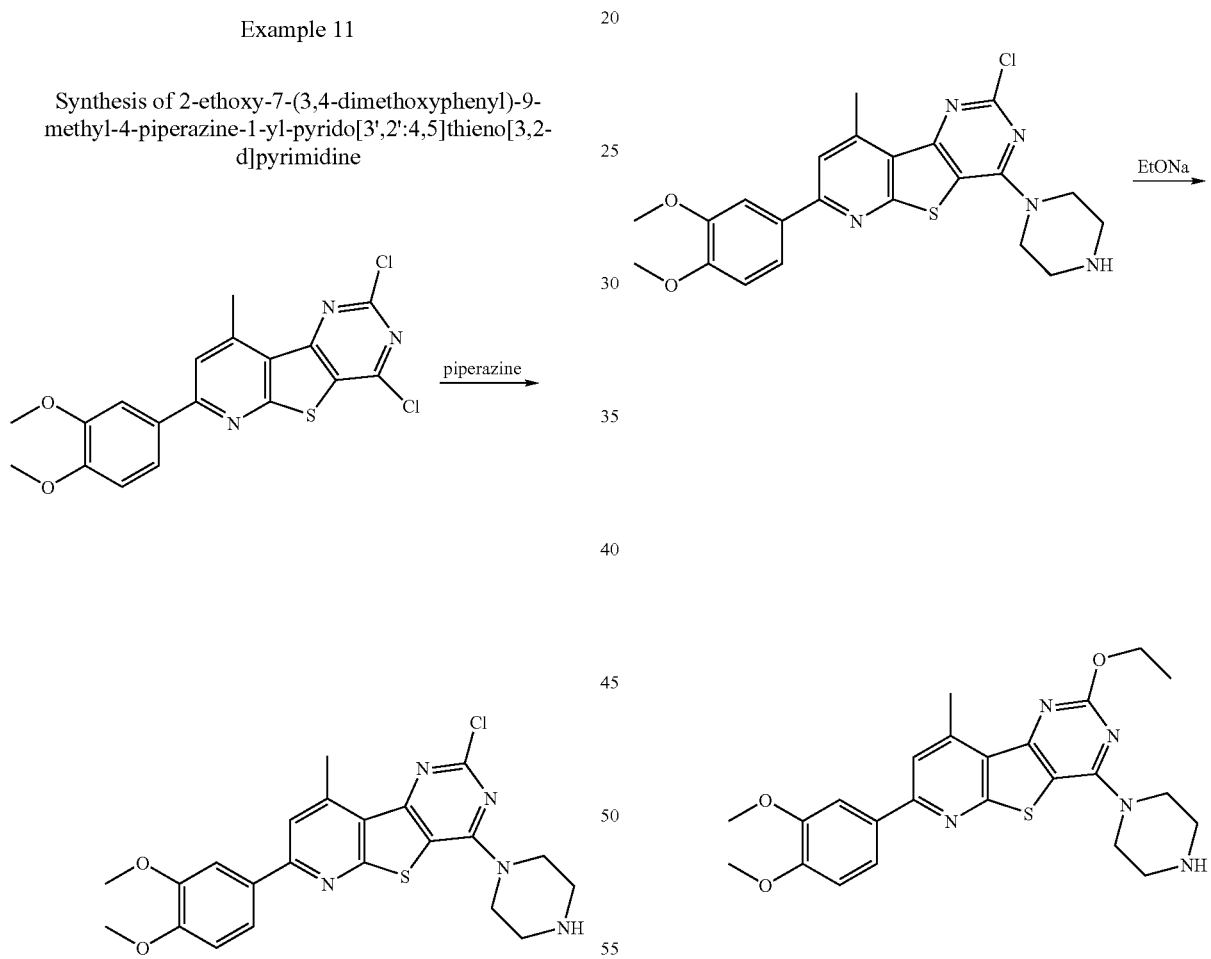 | 405.52 | 406 | n.d. |

Example 11

Synthesis of 2-ethoxy-7-(3,4-dimethoxyphenyl)-9-methyl-4-piperazine-1-yl-pyrido[3',2':4,5]thieno[3,2-d]pyrimidine 0.5 g (1.2 mmol) 2,4-dichloro-7-(3,4-dimethoxyphenyl)-9-methyl-pyrido-[3',2':4,5]-thieno[3,2-d]pyrimidine, 0.13 g (1.5 mmol) piperazine and 0.2 ml (1.5 mmol) triethylamine are added by stirring to 20 ml absolute tetrahydrofuran at room temperature for 6 h. Thereafter, the solvent is removed, the residue is suspended in water, sucked off, washed with about 40 ml water, suck dried and dried in vacuo at 50° C. 0.49 g (90%) 2-chloro-7-(3,4-dimethoxyphenyl)-9-methyl-4-piperazin-1-yl-pyrido-[3,2':4,5]thieno[3,2-d]pyrimidine is obtained.

0.1 g (0.22 mmol) 2-chloro-7-(3,4-dimethoxyphenyl)-9-methyl-4-piperazin-1-yl-pyrido-[3',2':4,5]thieno[3,2-d]pyrimidine and 0.22 ml (0.44 mmol) potassium ethylate (2M THF) are refluxed in 10 ml absolute dioxane for 3 h. Then, the solvent is removed and the residue is suspended in some water. The aqueous suspension is extracted with dichloromethane, the organic phase is dried on sodium sulfate and the solvent is removed. 50 mg (49%) of the title substance is obtained.

The following compounds were obtained according to Example 11 (Table 5)

TABLE 5

| Structure | M [g/mol] | ESI MS [m/z] [M + H]+ | Melting point [° C.] |
|---|---|---|---|
| 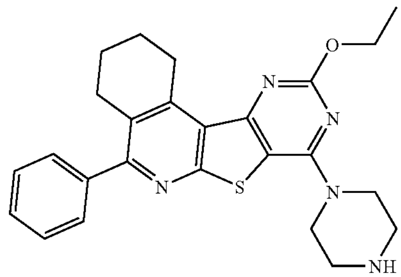 | 445.58 | 446 | 197-199 |
| 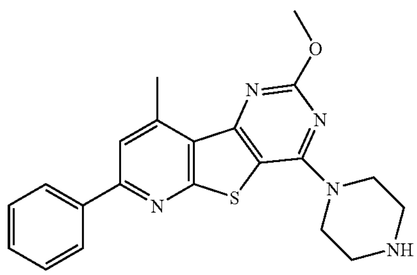 | 391.49 | 392 | 175-179 |
| 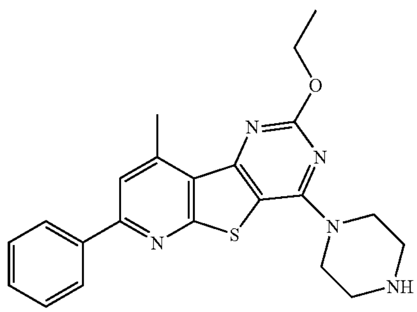 | 405.51 | 406 | 185-188 |
| 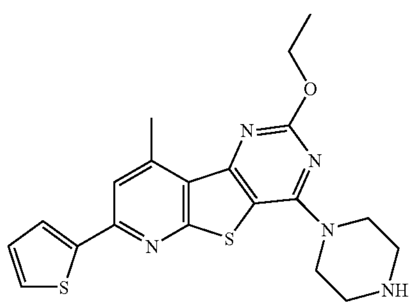 | 411.54 | 412 | n.d. |
| 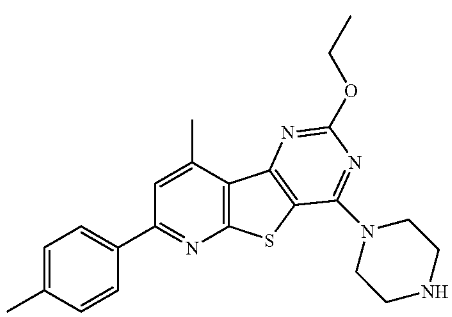 | 419.54 | 420 | n.d. |

TABLE 5-continued

| Structure | M [g/mol] | ESI MS [m/z] [M + H]⁺ | Melting point [° C.] |
|---|---|---|---|
| 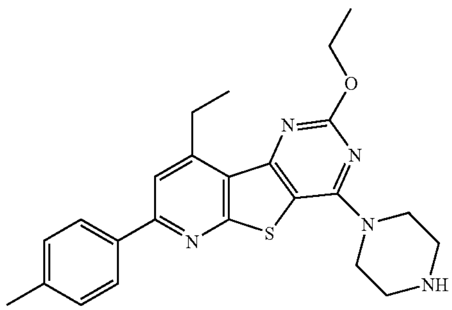 | 433.57 | 434 | n.d. |
| 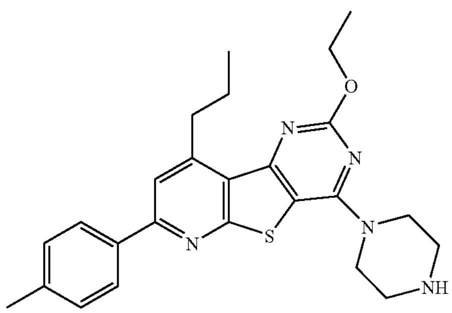 | 447.60 | 448 | n.d. |
| 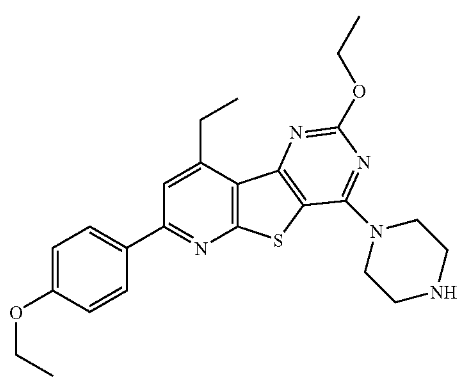 | 463.60 | 464 | n.d. |
| 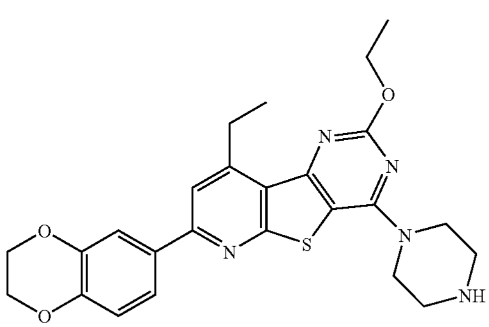 | 477.58 | 478 | 235 |

TABLE 5-continued

| Structure | M [g/mol] | ESI MS [m/z] [M + H]+ | Melting point [° C.] |
|---|---|---|---|
| (structure) | 525.55 | 526 | >400 |
| (structure) | 329.42 | 330 | 210-220 |
| (structure) | 435.54 | 436 | 191-194 |
| (structure) | 449.53 | 450 | n.d. |
| (structure) | 465.57 | 466 | n.d. |

TABLE 5-continued

| Structure | M [g/mol] | ESI MS [m/z] [M + H]+ | Melting point [° C.] |
|---|---|---|---|
| 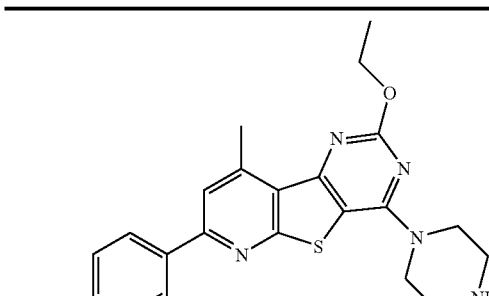 | 473.51 | 474 | n.d. |

Example 12

Synthesis of 4-ethoxy-2-piperazin-1-yl-7,8,9,10-tetrahydro-11-thiophene-2-yl-pyrimido[4',5':4,5]thieno[2,3-b]quinoline

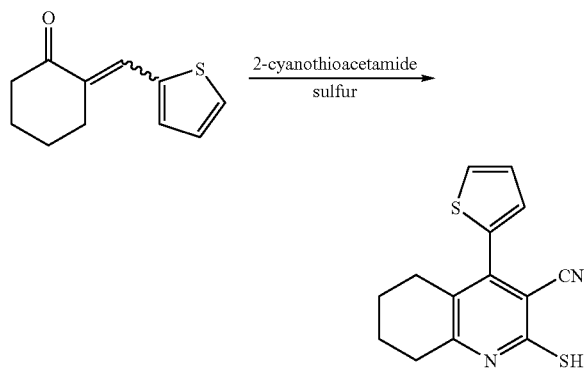

12.68 g (65.9 mmol) 2-thiophene-2-yl-methylene-cyclohexanone, 7.00 g (70.0 mmol) cyanthioacetamide and 10.00 g (72.4 mmol) potassium carbonate are refluxed in 100 ml acetone for 8 h. Then, 1.05 g (32.8 mmol) sulfur are added and refluxed for 12 h. The solvent is removed in vacuo and the residue is suspended in 600 ml ethanol/water (1:5). Following acidification with glacial acetic acid, the resulting precipitate is sucked off, washed with 200 ml water, suck dried and dried in vacuo at 50° C. 16.50 g (92%) 5,6,7,8-tetrahydro-2-mercapto-4-thiophen-2-yl-quinoline-3-carbonitrile is obtained.

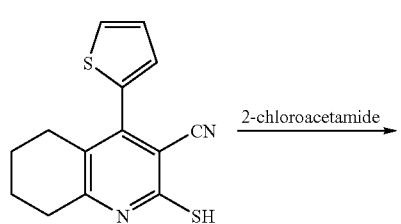

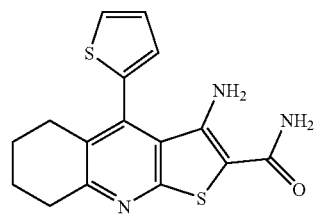

3.07 g (11.3 mmol) tetrahydro-2-mercapto-4-thiophen-2-yl-quinoline-3-carbonitrile 1.26 g (13.5 mmol) chloroacetamide and 3.2 g (47.0 mmol) sodium ethylate are refluxed in 70 ml absolute ethanol for 5 h. Following cooling, 100 ml water is added and the precipitate is sucked off, suck dried and dried in vacuo at 50° C. 1.9 g (51%) 3-amino-5,6,7,8-tetra-hydro-4-thiophen-2-yl-thieno[2,3-b]quinoline-2-carboxamide is obtained.

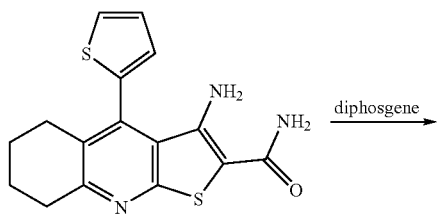

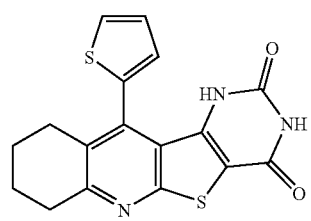

The reaction of 3-amino-5,6,7,8-tetrahydro-4-thiophene-2-yl-thieno[2,3-b]quinoline-2-carboxamide with diphosgene into 7,8,9,10-tetrahydro-11-thiophen-2-yl-pyrimido[4',5':4,5]thieno[2,3-b]quinoline-2,4-dione is carried out in analogy to Example 1.

In this connection, 1.06 g (52%) product is obtained from 1.87 g (5.7 mmol) educt.

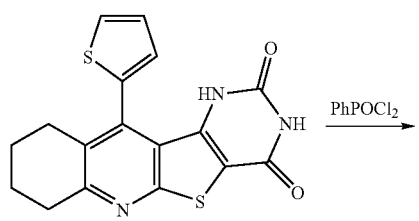

PhPOCl₂ →

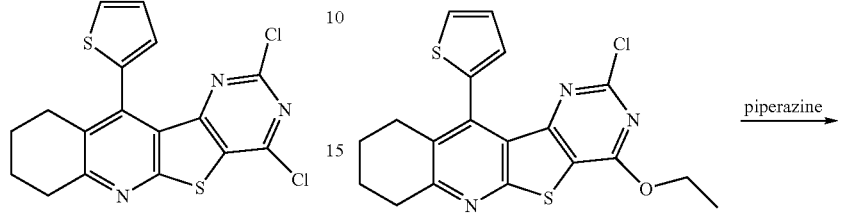

The reaction of 7,8,9,10-tetrahydro-11-thiophen-2-yl-pyrimido[4',5':4,5]-thieno-[2,3-b]quinoline-2,4-dione with dichlorophenylphosphineoxide into 2,4-dichloro-7,8,9,10-tetrahydro-11-thiophen-2-yl-pyrimido[4',5':4,5]-thieno[2,3-b]quinoline is carried out in analogy to Example 1.

In this connection, 1.10 g (97%) product is obtained from 1.03 g (2.9 mmol) educt.

The reaction of 2,4-dichloro-7,8,9,10-tetrahydro-11-thiophen-2-yl-pyrimido-[4',5':4,5]thieno[2,3-b]quinoline with sodium ethylate into 2-chloro-4-ethoxy-7,8,9,10-tetrahydro-11-thiophen-2-yl-pyrimido-[4',5':4,5]thieno[2,3-b]quinoline is carried out in analogy to Example 1.

In this connection, 0.36 g (64%) product is obtained from 0.50 g (1.4 mmol) educt.

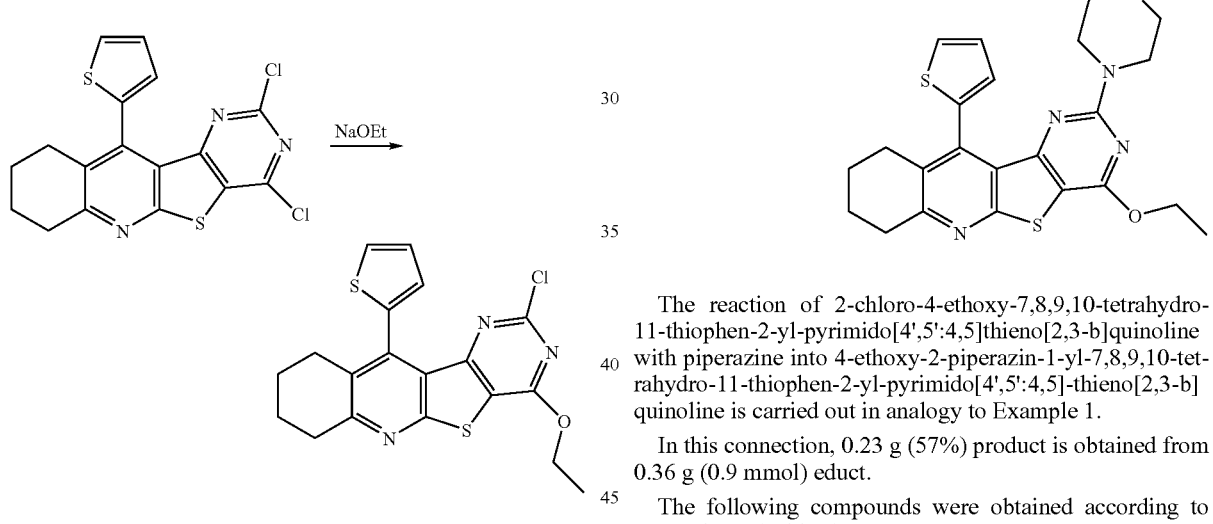

The reaction of 2-chloro-4-ethoxy-7,8,9,10-tetrahydro-11-thiophen-2-yl-pyrimido[4',5':4,5]thieno[2,3-b]quinoline with piperazine into 4-ethoxy-2-piperazin-1-yl-7,8,9,10-tetrahydro-11-thiophen-2-yl-pyrimido[4',5':4,5]thieno[2,3-b]quinoline is carried out in analogy to Example 1.

In this connection, 0.23 g (57%) product is obtained from 0.36 g (0.9 mmol) educt.

The following compounds were obtained according to Example 12 (Table 6)

TABLE 6

| Structure | M [g/mol] | ESI MS [m/z] [M + H]⁺ | Melting point [° C.] |
|---|---|---|---|
| 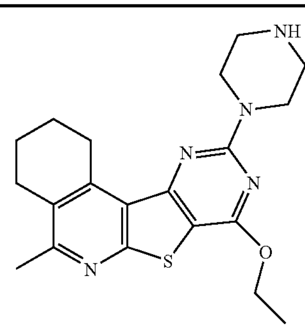 | 465.47 | 466 | 167-171 |

TABLE 6-continued

| Structure | M [g/mol] | ESI MS [m/z] [M + H]+ | Melting point [° C.] |
|---|---|---|---|
| 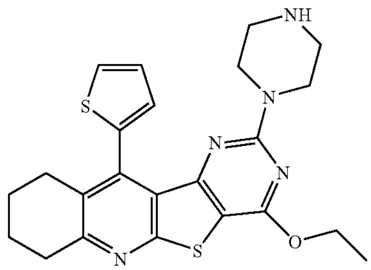 | 451.61 | 452 | n.d. |
| 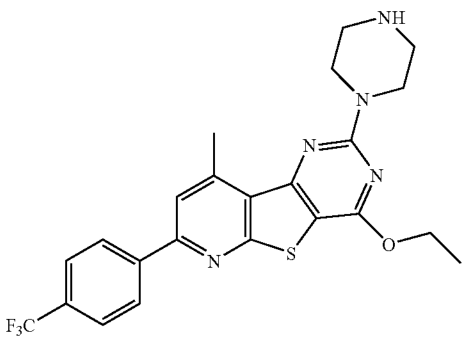 | 473.51 | 474 | n.d. |
| 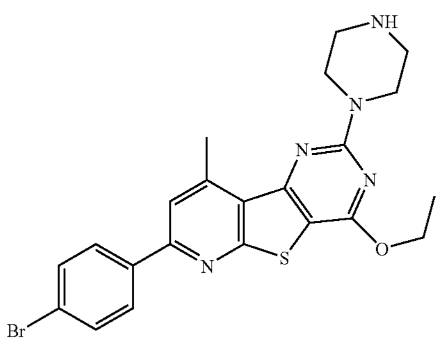 | 484.41 | 485 | n.d. |
| 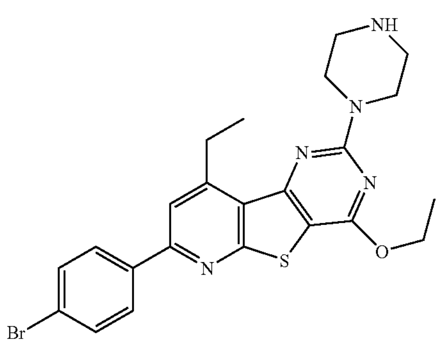 | 498.43 | 499 | n.d. |

TABLE 6-continued

| Structure | M [g/mol] | ESI MS [m/z] [M + H]+ | Melting point [° C.] |
|---|---|---|---|
| 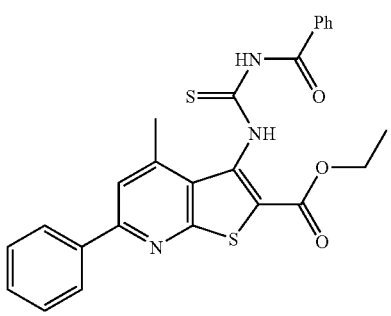 | 545.43 | 546 | n.d. |

Example 13

Synthesis of 2-ethylthio-9-methyl-7-phenyl-4-piperazin-1-yl-pyrido-[3',2':4,5]thieno[3,2-d]pyrimidine

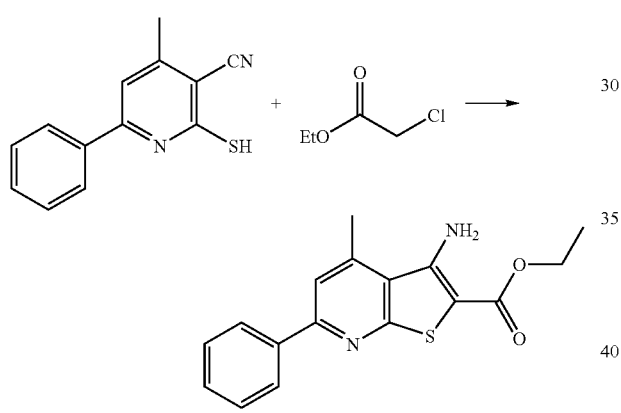

6.45 g (28.5 mmol) 2-mercapto-4-methyl-6-phenyl-pyridine-3-carbonitrile is supplied to 100 ml absolute ethanol and 5.3 ml (50.0 mmol) 2-chloroethyl acetate and 10 ml (72.1 mmol) triethylamine are added. The next step is refluxing for 1 h and the precipitate precipitated after cooling is sucked off, washed with some water and ethanol, suck dried and dried in vacuo at 50° C.

Then, the precipitate is refluxed in a solution of 0.14 g (1.6 mmol) sodium ethylate in absolute ethanol for 1 h. The precipitate is sucked off, washed with 30 ml water and 15 ml ethanol, suck dried and dried in vacuo at 50° C. 5.0 g (91%) 3-amino-4-methyl-6-phenyl-thieno[2,3-b]pyridine-2-carboxylic acid ethyl ester is obtained.

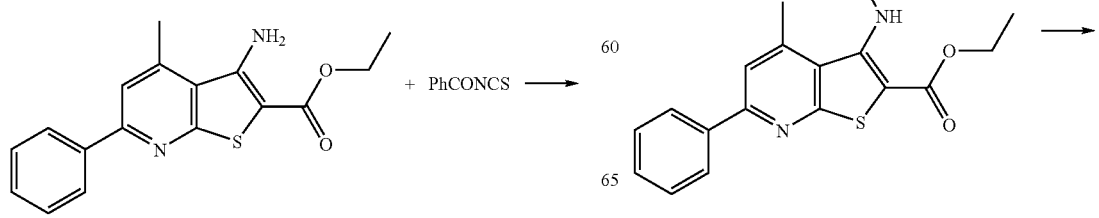

5 ml (13.3 mmol) acetonic benzoyl-isothiocyanate solution (2 M) is added to 2.78 g (8.9 mmol) 3-amino-4-methyl-6-phenyl-thieno[2,3-b]pyridine-2-carboxylic acid ethyl ester in 10 ml acetone and refluxed for 2 h. The precipitate precipitated after cooling is sucked off, washed with some water and ethanol, suck dried and dried in vacuo at 50° C. 3.93 g (93%) 3-(3-benzoylthioureido)-4-methyl-6-phenyl-thieno[2,3-b]pyridine-2-carboxylic acid ethyl ester is obtained.

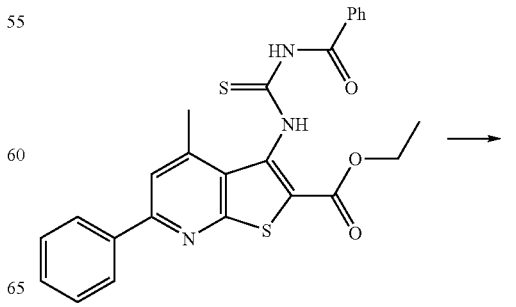

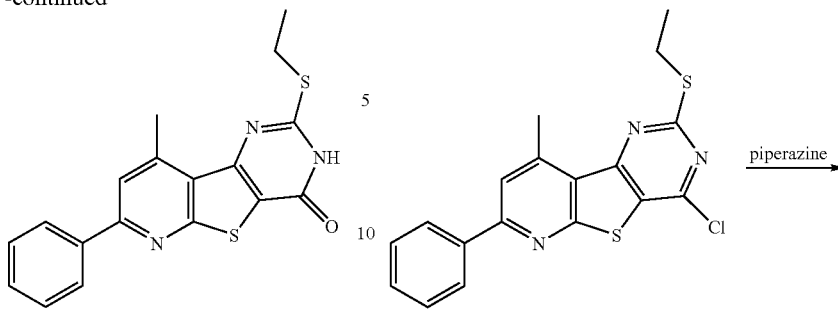

10.5 ml (10.5 mmol) 1 M sodium hydroxide solution is added to 2.00 g (4.2 mmol) 3-(3-benzoylthioureido)-4-methyl-6-phenyl-thieno[2,3-b]-pyridine-2-carboxylic acid ethyl ester in 25 ml ethanol and refluxed for 30 min. Following the addition of 10 ml N,N-dimethylformamide, 5 ml (5 mmol) sodium hydroxide solution (1M) and 0.50 ml iodoethane (6.2 mmol) the next step is stirring at room temperature for 30 min. The precipitate precipitated following acidification with dilute hydrochloric acid is sucked off, washed with water, suck dried and dried in vacuo at 50° C. 1.23 g (83%) 2-ethylthio-9-methyl-7-phenyl-pyrido[3',2':4,5]thieno-[3,2-d]pyrimidin-4-one is obtained.

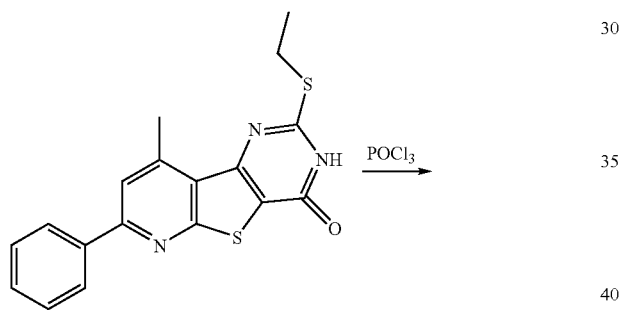

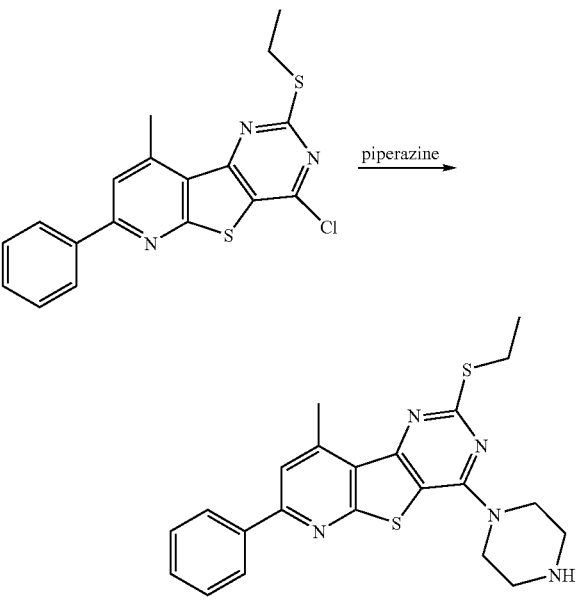

0.63 g (1.7 mmol) 4-chloro-2-ethylthio-9-methyl-7-phenyl-pyrido-[3',2':4,5]thieno[3,2-d]pyrimidine is stirred with 0.29 g (3.4 mmol) piperazine in 10 ml tetrahydrofuran at room temperature for 1 h. The precipitate is sucked off, washed with some water and suck dried. Thereafter, the precipitate is suspended in about 300 ml dichloromethane, fully stirred, filtrated and the solvent of the filtrate is removed. 0.67 g (93%) of the title substance is obtained. ESI-MS [m/z]: 422, melting point: 150-154° C.

Example 14

Synthesis of 2-ethylsulfinyl-9-methyl-7-phenyl-4-piperazin-1-yl-pyrido-[3',2':4,5]thieno[3,2-d]pyrimidine

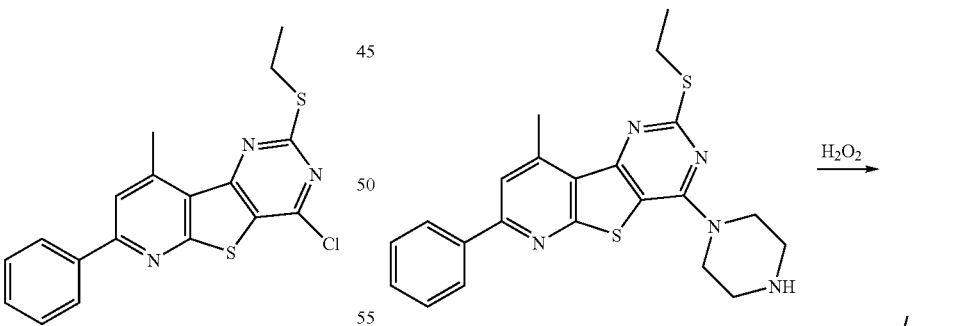

1.23 g (3.5 mmol) 2-ethylthio-9-methyl-7-phenyl-pyrido[3',2':4,5]-thieno[3,2-d]pyrimidin-4-one is refluxed in 10 ml (10.9 mol) phosphoroxychloride for 6 h. Then, the product is poured onto about 100 g ice water and neutralized with saturated sodium hydrogen carbonate solution. The precipitate is sucked off, washed with about 100 ml water, dried and purified by means of flash chromatography (dichloromethane/petroleum ether 5:1). 0.29 g (22%) 4-chloro-2-ethylthio-9-methyl-7-phenyl-pyrido[3',2':4,5]thieno[3,2-d]pyrimidine is obtained.

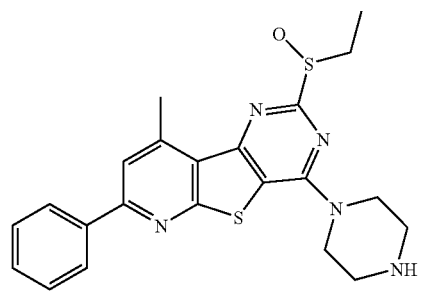

85 mg (0.2 mmol) 2-ethylthio-9-methyl-7-phenyl-4-piper-azin-1-yl-pyrido[3',2':4,5]-thieno[3,2-d]pyrimidine, 3 ml glacial acetic acid and 0.04 ml hydrogen peroxide (60%) are stirred at room temperature for 48 h. Having removed the solvent, the residue is purified by means of flash chromatography (methanol/dichloromethane 1:20-1:3). 50 mg (57%) of the title substance is obtained. ESI-MS [m/z]: 438, melting point: 165-170° C.

The following compound was prepared analogously:

4-Ethoxy-7-(4-methylsulfinyl-phenyl)-2-piperazin-1-yl-9-trifluoromethyl-pyrido-[3',2':4,5]thieno[3,2-d]pyrimidine

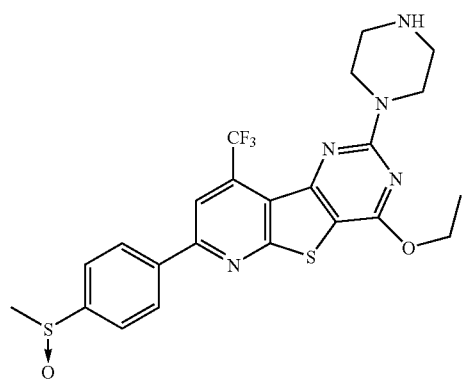

ESI-MS [m/z]: 522

Example 15

Synthesis of 2-ethylsulfonyl-9-methyl-7-phenyl-4-piperazin-1-yl-pyrido-[3',2':4,5]thieno[3,2-d]pyrimidine

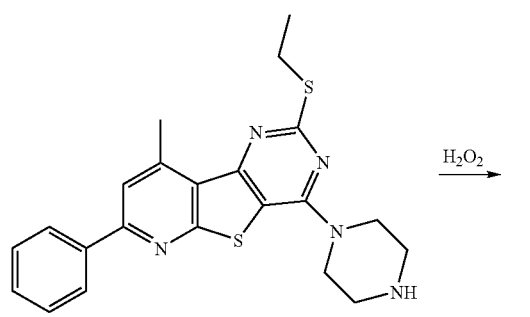

85 mg (0.2 mmol) 2-ethylthio-9-methyl-7-phenyl-4-piper-azin-1-yl-pyrido[3',2':4,5]-thieno[3,2-d]pyrimidine, 3 ml glacial acetic acid and 0.12 ml hydrogen peroxide (60%) are stirred at room temperature for 96 h. Having removed the solvent, the residue is purified by means of flash chromatography (methanol/dichloromethane 1:20-1:10). 16 mg (18%) of the title substance is obtained. ESI-MS [m/z]: 454, melting point: 190° C. decomp.

Example 16

Synthesis of 7-(3,4-dimethoxyphenyl)-9-methyl-4-piperazin-1-yl-2-n-propyl-pyrido[3',2':4,5]thieno[3,2-d]pyrimidine

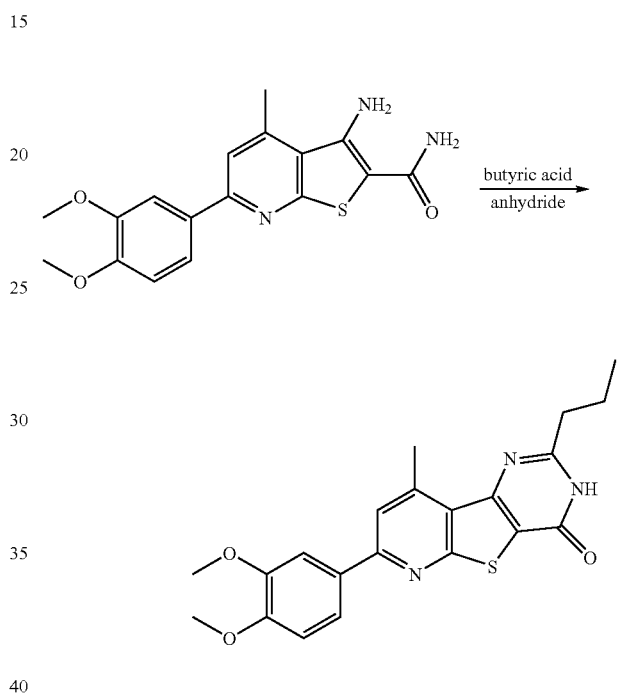

1.10 g (3.2 mmol) 3-amino-6-(3,4-dimethoxyphenyl)-4-methyl-thieno-[2,3-b]pyridine-2-carboxamide and 10.0 ml (89.1 mmol) butyric anhydride in 10 ml toluene are refluxed for 6 h. Having cooled down, the precipitate is sucked off, washed with about 5 ml ethanol and suck dried. The residue is refluxed in 5.0 ml sodium ethylate solution (21%) for 6 h. Having cooled down, the next step is acidification using HCl (10%) to pH 6 under cooling. Then, the precipitate is sucked off, washed with about 30 ml water, suck dried and dried in vacuo at 50° C. 0.59 g (47%) 7-(3,4-dimethoxyphenyl)-9-methyl-2-propyl-pyrido[3',2':4,5]thieno-[3,2-d]-pyrimidin-4-one is obtained.

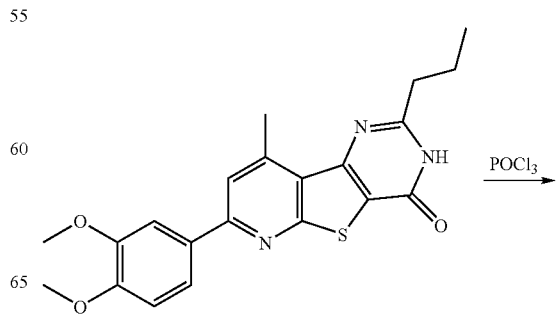

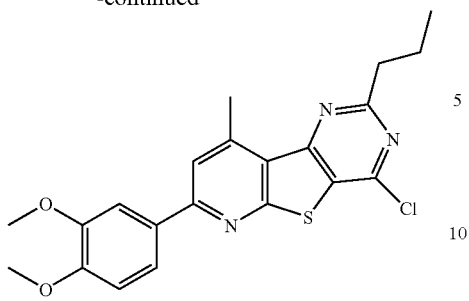

0.57 g (1.4 mmol) 7-(3,4-dimethoxyphenyl)-9-methyl-2-propyl-pyrido[3',2':4,5]thieno-[3,2-d]pyrimidin-4-one is refluxed in 8 ml (86.4 mmol) phosphoroxychloride for 9 h. Then, the product is poured onto about 50 g ice water. The precipitate is sucked off, washed with about 250 ml water, suck dried and dried in vacuo at 50° C. 0.58 g (96%) 4-chloro-7-(3,4-dimethoxyphenyl)-9-methyl-2-propyl-pyrido[3',2':4,5]-thieno[3,2-d]pyrimidine is obtained.

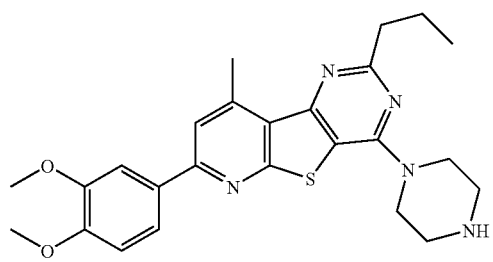

0.42 g (1.0 mmol) 4-chloro-7-(3,4-dimethoxyphenyl)-9-methyl-2-propyl-pyrido-[3',2':4,5]thieno[3,2-d]pyrimidine and 0.37 g (4.3 mmol) piperazine in 8 ml tetrahydrofuran are stirred at room temperature for 4 h. Having removed the solvent, the residue is suspended in 10 ml water and sucked off. The residue is suspended in about 50 ml dichloromethane and filtrated. The filtrate is washed with a total of 30 ml water, dried on sodium sulfate and the solvent is removed. The residue is recrystallized from ethyl acetate. 0.17 g (37%) of the title substance is obtained.

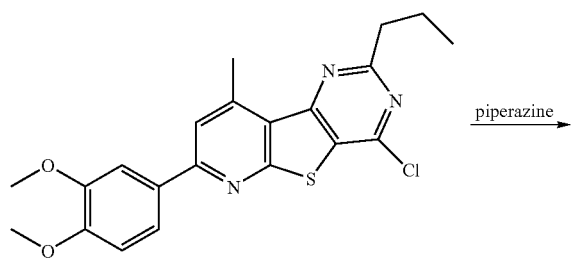

The following compounds were obtained according to Example 16 (Table 7)

TABLE 7

| Structure | M [g/mol] | ESI MS [m/z] | Melting point [° C.] |
|---|---|---|---|
| 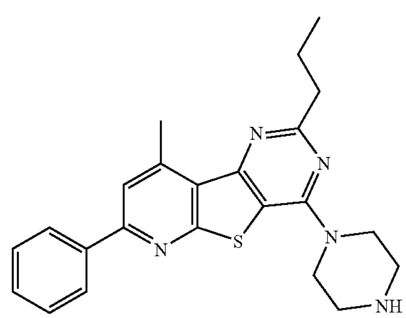 | 403.54 | 404 [M + H]⁺ | 162-163 |
| 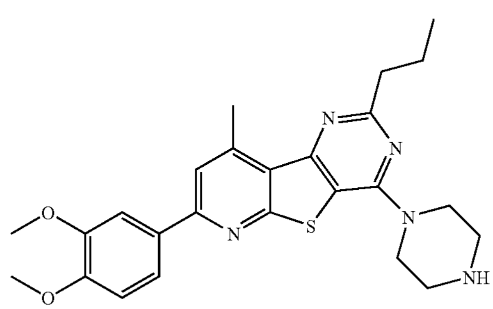 | 463.60 | 464 [M + H]⁺ | 130-132 |

TABLE 7-continued

| Structure | M [g/mol] | ESI MS [m/z] | Melting point [° C.] |
|---|---|---|---|
| 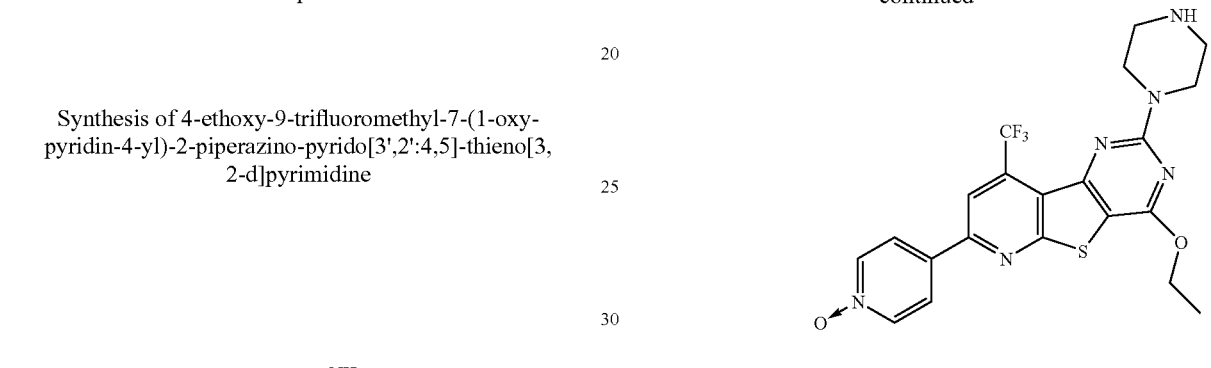 | 389.52 | 390 [M + H]+ | 155-158 |

Example 17

Synthesis of 4-ethoxy-9-trifluoromethyl-7-(1-oxy-pyridin-4-yl)-2-piperazino-pyrido[3',2':4,5]-thieno[3,2-d]pyrimidine

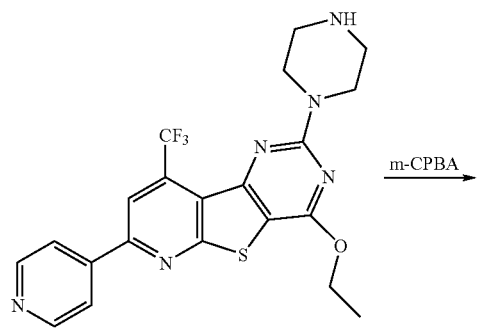 m-CPBA →

-continued 0.4 g (1 mmol) 4-ethoxy-9-trifluoromethyl-7-(pyridin-4-yl)-2-piperazino-pyrido[3',2':4,5]-thieno[3,2-d]pyrimidine is heated in 10 ml dichloro-methane with 0.5 g m-chloroperbenzoic acid in the ultrasonic bath for 3-5 h. 250 ml dichloromethane is added, washed with sodium hydrogen sulfite solution and then washed with sodium hydrogen carbonate solution. The organic phase is dried on $Na_2SO_4$ and the solvent is removed. 0.4 g (97%) of the title substance is obtained.

The following compounds were obtained according to Example 17 (Table 8)

TABLE 8

| Structure | M [g/mol] | ESI MS [m/z] | Melting point [° C.] |
|---|---|---|---|
| 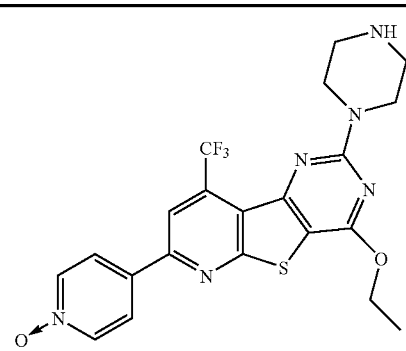 | 476.47 | 477 [M + H]+ | 215 |

| Structure | M [g/mol] | ESI MS [m/z] | Melting point [°C.] |
|---|---|---|---|
| | 476.47 | 477 [M + H]⁺ | 261 |
| | 476.47 | 477 [M + H]⁺ | 250-251 |

Example 18

Synthesis of 2-ethoxy-9-methyl-7-phenyl-4-piperazin-1-yl-pyrido[3',2':4,5]-furo[3,2-d]pyrimidine

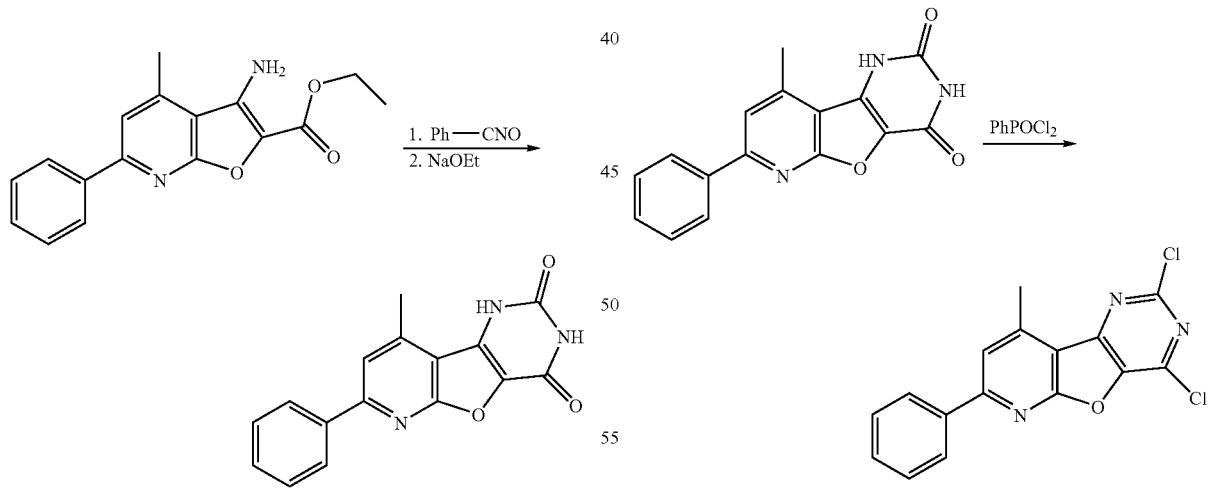

1.0 g (6.8 mmol) benzoylisocyanate is added to 1.0 g (3.4 mmol) 3-amino-4-methyl-6-phenyl-furo[2,3-b]pyridine-2-carboxylic acid ethyl ester (described in Wagner G., Prantz J. *Pharmazie* 1990, 45, 213-214) in 20 ml absolute acetone and stirred at room temperature for 30 minutes. The solvent is removed and the precipitate precipitated after the addition of water is sucked off and dried. The resulting precipitate is refluxed with 0.46 g (6.8 mmol) NaOEt and 20 ml ethanol for 15 min. Then, 20 ml water is added, the precipitate is sucked off, washed with some ethanol and dried. 0.85 g (85%) 9-methyl-7-phenyl-pyrido[3',2':4,5]furo[3,2-d]pyrimidin-2,4-dione is obtained 0.85 g (2.9 mmol) 9-methyl-7-phenyl-pyrido[3',2':4,5]furo[3,2-d]pyrimidine-2,4-dione and 2.4 ml (17.4 mmol) dichlorophenylphosphinoxide are heated at 180° C. for 6 h. Then, the product is poured onto about 20 g ice water and neutralized with saturated sodium hydrogen carbonate solution. The precipitate is sucked off, washed with about 100 ml water, suck dried and dried in vacuo at 50° C. 0.88 g (92%) 2,4-dichloro-9-methyl-7-phenyl-pyrido[3',2':4,5]furo[3,2-d]pyrimidine is obtained.

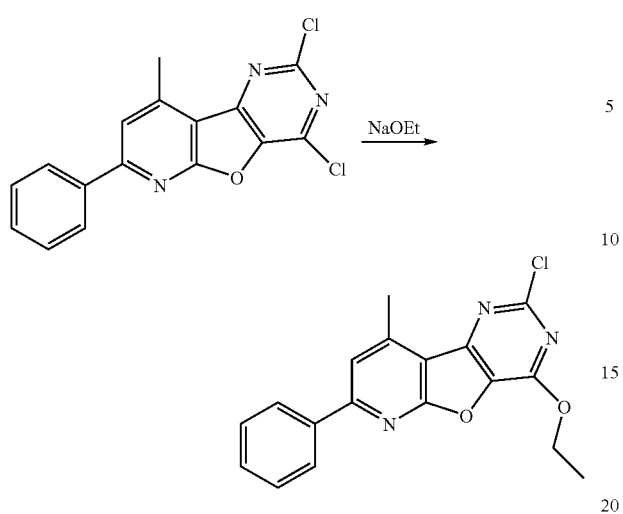

0.2 g (0.6 mmol) 2,4-dichloro-9-methyl-7-phenyl-pyrido [3',2':4,5]furo-[3,2-d]pyrimidine and 0.12 g (1.8 mmol) sodium ethylate are added by stirring into 50 ml absolute ethanol at room temperature for 24 h. Then, the precipitate is sucked off, washed with about 40 ml water and dried. Following flash chromatography, 94 mg (46%) 2-chloro-4-ethoxy-9-methyl-7-phenyl-pyrido[3',2':4,5]furo[3,2-d]pyrimidine is obtained.

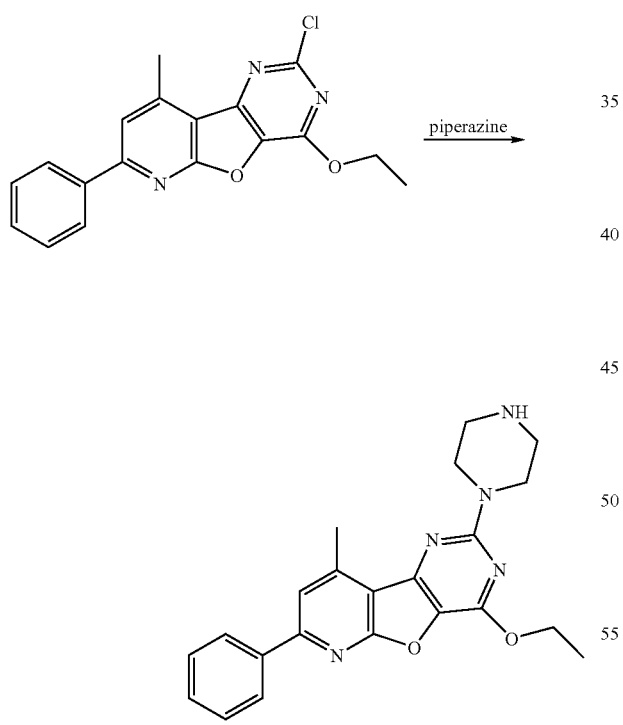

90 mg (0.26 mmol) 2-chloro-4-ethoxy-9-methyl-7-phenyl-pyrido-[3',2':4,5]furo[3,2-d]pyrimidine and 91 mg (1.1 mmol) piperazine are refluxed in 10 ml toluene for 8 h. Then, the solvent is removed and the residue is suspended in dichloromethane. The organic phase is washed with saturated sodium carbonate solution, dried on sodium sulfate and the solvent is removed. The residue is purified by flash chromatography (ethanol/chloroform 1:5). 52 mg (51%) of the title substance is obtained. ESI-MS [m/z]: 390, melting point: 131-132° C.

Example 19

2-ethoxy-9-methyl-7-phenyl-4-piperazin-1-yl-pyrido [3',2':4,5]-furo[3,2-d]pyrimidine was obtained in analogy to Example 11

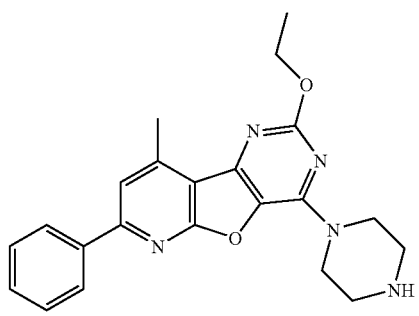

MS [m/z]: 390, melting point: 175° C.

Example 20

4-Ethoxy-9-trifluoromethyl-2-piperazin-1-yl-7-(4-(1H-pyrazol-1-yl)-phenyl)-pyrido-[3',2':4,5]thieno[3,2-d]pyrimidine

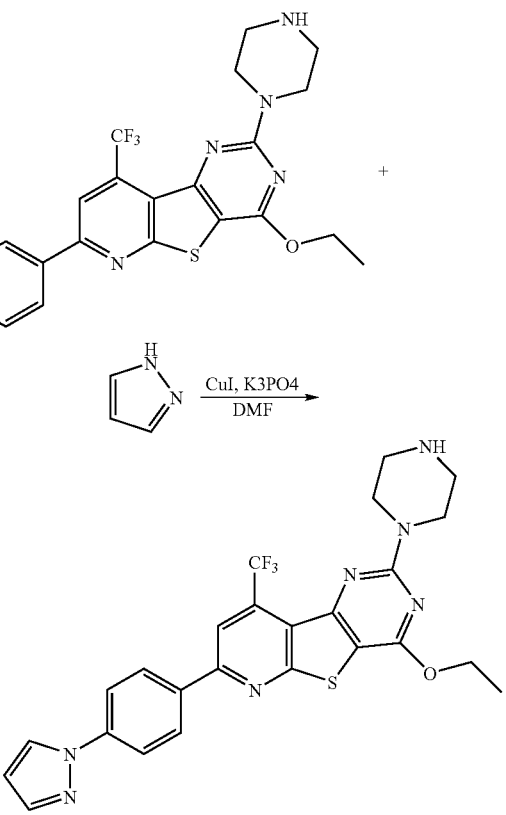

0.30 g (0.5 mmol) 4-ethoxy-9-trifluoromethyl-7-(4-iodophenyl)-2-piperazin-1-yl-pyrido[3',2':4,5]thieno[3,2-d]pyrimidine, 0.14 g (2.1 mmol) pyrazole, 0.22 g (1.0 mmol) potassiumphosphate-tribasic, 0.06 g (0.3 mmol) copper(I)-iodide and 0.014 g (0.1 mmol) (1R,2R)—N,N'-dimethyl-1,2-cyclohexanediamine in 5 ml N,N-dimethylformamide (dry) are stirred at 110° C. under nitrogen atmosphere for 24 h. The solvent is removed in vacuo and the residue is suspended in 20 ml water, sucked off, washed with 100 ml water and suck dried. Following purification by means of flash chromatography (methanol/dichloromethane 1:10) 0.04 g (15%) 4-ethoxy-9-trifluoromethyl-2-piperazin-1-yl-7-(4-(1H-pyrazol-1-yl)-phenyl)-pyrido[3',2':4,5]thieno-[3,2-d]pyrimidine is obtained.

The following compounds were obtained according to Example 20 (Table 9)

TABLE 9

| Structure | M [g/mol] | ESI MS [m/z] [M + H]+ | Melting point [° C.] |
|---|---|---|---|
|  | 485.60 | 486 | 189 |
|  | 485.60 | 486 | 202-203 |
| 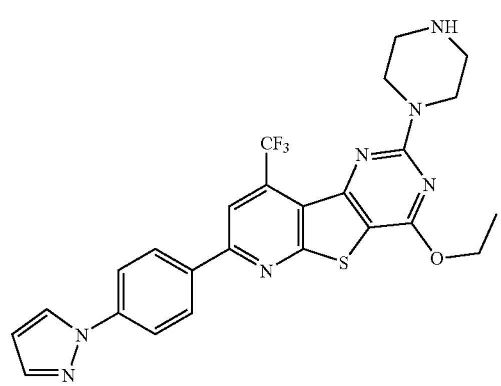 | 525.54 | 527 | 235-236 |

TABLE 9-continued

| Structure | M [g/mol] | ESI MS [m/z] [M + H]+ | Melting point [° C.] |
|---|---|---|---|
| 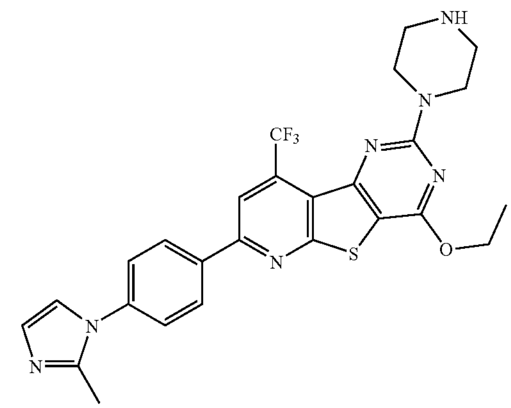 | 539.57 | 540 | 232-233 |
| 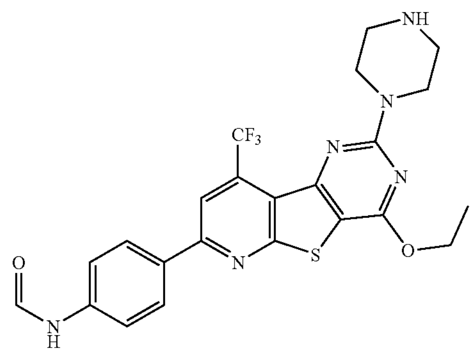 | 502.51 | 503 | 257 |
| 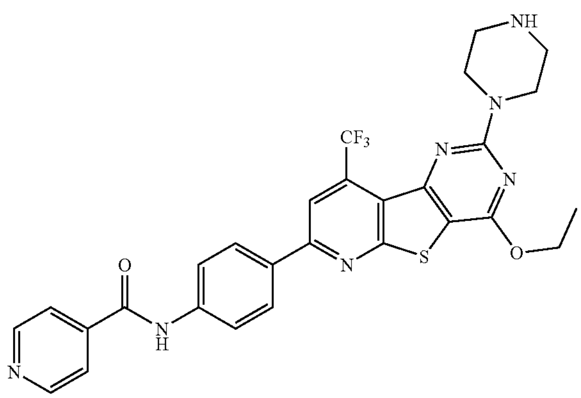 | 579.60 | 580 | 209 |
| 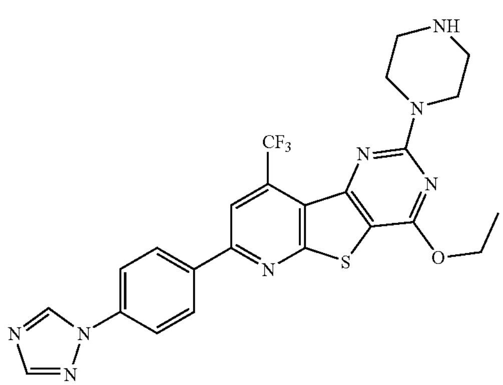 | 526.54 | 527 | 269-270 |

TABLE 9-continued

| Structure | M [g/mol] | ESI MS [m/z] [M + H]+ | Melting point [° C.] |
|---|---|---|---|
| 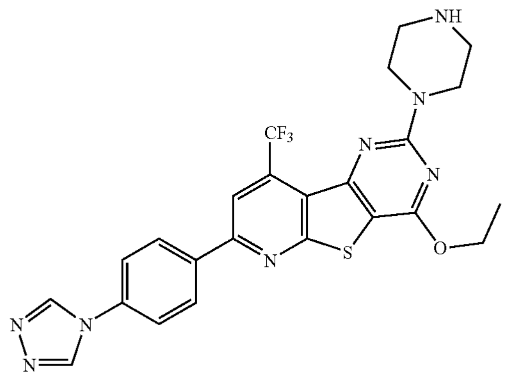 | 526.54 | 527 | 252-253 |
| 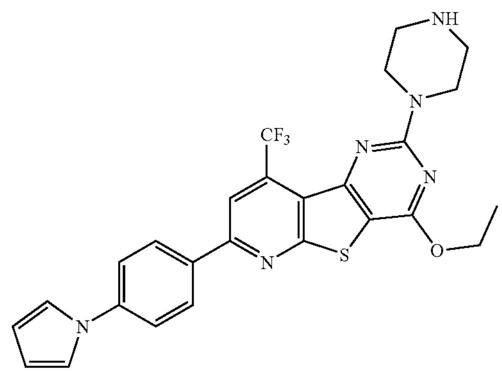 | 524.56 | 525 | 223-224 |

Example 21

Synthesis of 8-(4-aminobenzyl)-4-ethoxy-7,9-dimethyl-2-piperazin-1-yl-pyrido[3',2':4,5]thieno[3,2-d]pyrimidine 40 mg 10% Pd/C and 0.5 ml (10 mmol) hydraziniumhydroxide are added to 0.36 g (0.8 mmol) 4-ethoxy-7,9-dimethyl-8-(4-nitrobenzyl)-2-piperazin-1-yl-pyrido[3',2':4,5]thieno[3,2-d]pyrimidine in 3 ml ethanol. Then, refluxing is carried out for 10 h, the solvent is removed and the residue is taken up with 50 ml chloroform. Following filtration, the solvent is removed and the residue is recrystallized from chloroform/cyclohexane. 0.16 g (45%) of the title substance is obtained.

The following compounds were obtained according to Example 21 (Table 10)

TABLE 10

| Structure | M [g/mol] | ESI MS [m/z] [M + H]+ | Melting point [° C.] |
|---|---|---|---|
| 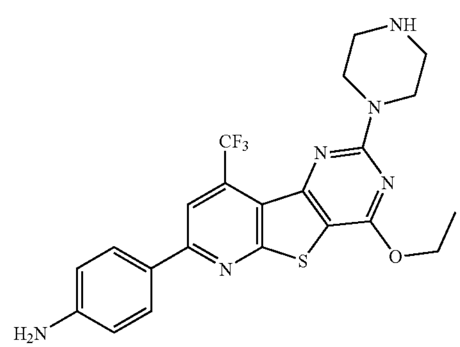 | 474.50 | 475 | 229-233 |

TABLE 10-continued

| Structure | M [g/mol] | ESI MS [m/z] [M + H]⁺ | Melting point [° C.] |
|---|---|---|---|
| 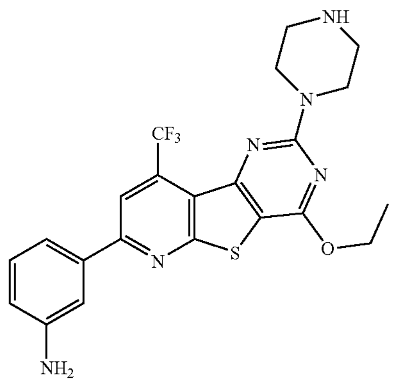 | 474.50 | 475 | n.d. |
| 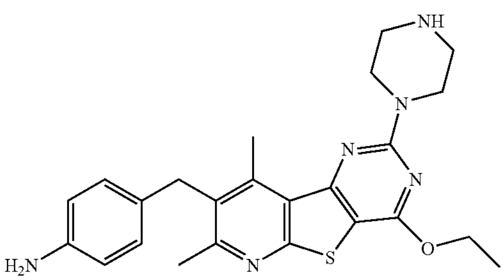 | 448.58 | 449 | 195-202 |

Example 22

Synthesis of 4-ethoxy-9-ethyl-7-(4-(pyrimidyl-2-yl) piperazin-1-yl)-2-piperazin-1-yl-pyrido[3',2':4,5] thieno[3,2-d]pyrimidine

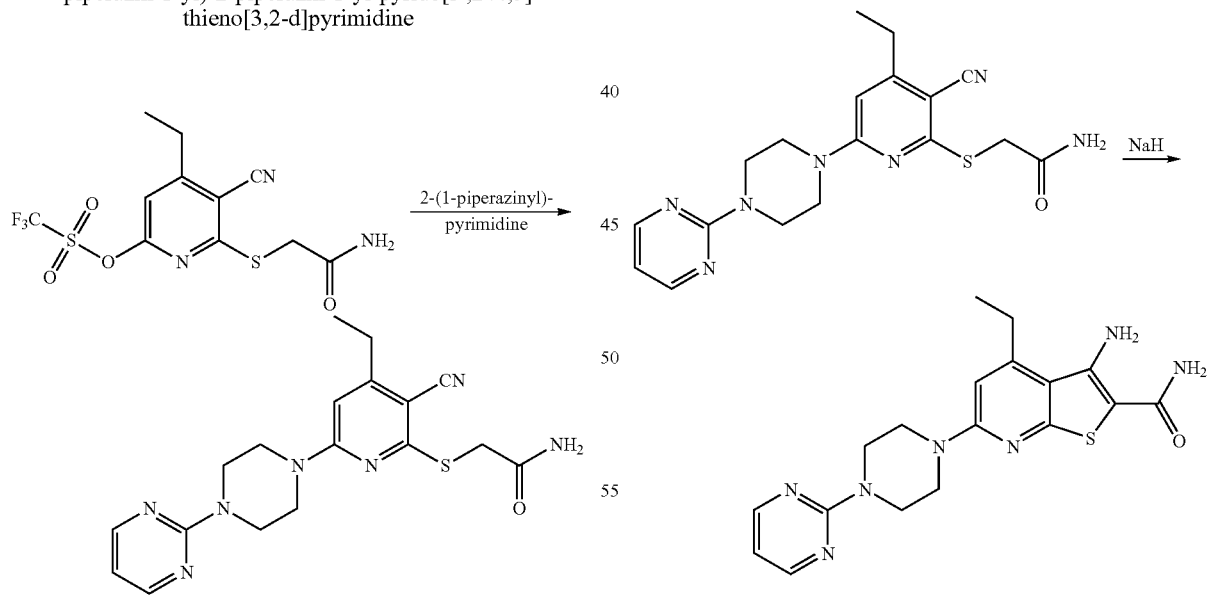

1.6 g (4.34 mmol) 6-(carbamoylmethylthio)-5-cyano-4-ethylpyridin-2-yl-trifluoro-methanesulfonate, accessable e.g. in analogy to US 2004/0180922, is stirred with 1.45 g (8.8 mmol) 2-(1-piperazinyl)pyrimidine in 20 ml dry dioxane at room temperature for 5 h. The product is precipitated with 500% by volume of water. Following washing (water) and drying in vacuo overnight, 1.58 g (95%) 2-(3-cyano-4-ethyl-6-(4-(pyrimidyl-2-yl)piperazin-1-yl)pyridin-2-ylthio)acetamide is obtained as a gray powder.

1.58 g (4.13 mmol) 2-(3-cyano-4-ethyl-6-(4-pyrimidyl-2-yl)piperazin-1-yl)pyridin-2-ylthio)acetamide is suspended in 25 ml dry DMF and stirred with 100 mg NaH at room temperature for 3 h. Having carefully poured the suspension into 300 ml water, the product is sucked off, washed with water and dried in vacuo. 780 mg (45%) 3-amino-4-ethyl-6-(4-(pyrimidin-2-yl)piperazin-1-yl)thieno[2,3-b]pyridine-2-carboxamide is obtained as an ochre powder.

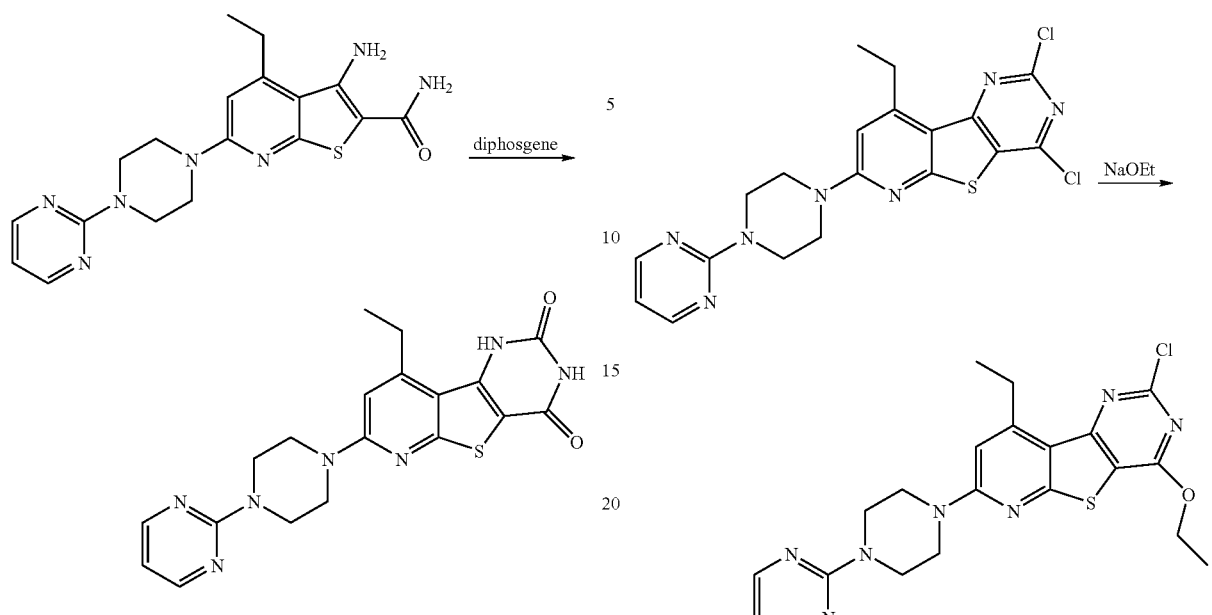

3-Amino-4-ethyl-6-(4-(pyrimidin-2-yl)piperazin-1-yl)thieno[2,3-b]-pyridine-2-carboxamide is reacted with diphosgene into 9-ethyl-7-(4-(pyrimidin-2-yl)piperazin-1-yl)pyrido[3',2':4,5]thieno[3,2-d]pyrimidine-2,4-dione in analogy to Example 1.

In this connection, 740 mg (77%) crude product is obtained from 900 mg (2.35 mmol) educt, which is subjected to chlorination without further purification.

1.5 g (3.7 mmol) (9-ethyl-7-(4-(pyrimidin-2-yl)piperazin-1-yl)pyrido[3',2':4,5]thieno-[3,2-d]pyrimidine-2,4-dione is reacted with dichlorophenylphosphineoxide in analogy to Example 1. The residue obtained at 140° C. after 30 h is purified by means of flash chromatography (methylene chloride/methanol). 400 mg (24%) 2,4-dichloro-9-ethyl-7-(4-(pyrimidin-2-yl)piperazin-1-yl)pyrido[3',2':4,5]thieno[3,2-d]pyrimidine is obtained as a colorless solid.

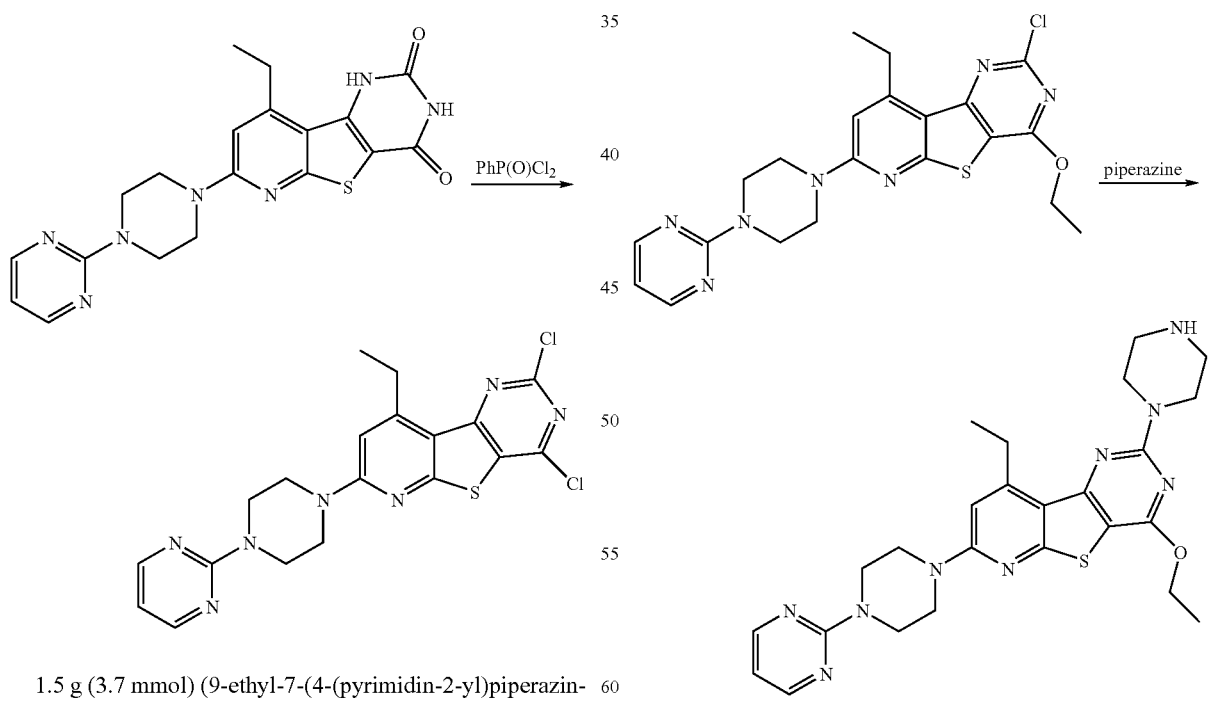

In analogy to Example 1, 180 mg product mixtures is obtained from 200 mg (0.45 mmol) dichloro compound, which is further reacted without isolating 2-chloro-4-ethoxy-9-ethyl-7-(4-(pyrimidin-2-yl)piperazin-1-yl)-pyrido[3',2':4,5]thieno[3,2-d]pyrimidine.

In analogy to Example 1, 30 mg (13% with respect to the dichloro compound) is obtained from 170 mg 2-chloro-4-ethoxy-9-ethyl-7-(4-(pyrimidin-2-yl)piperazin-1-yl)pyrido-[3',2':4,5]thieno[3,2-d]pyrimidine as a yellow powder following flash chromatografic purification.

The compounds shown according to Example 22 are comprised in Table 11.

TABLE 11

| Structure | M [g/mol] | MS (ESI) [m/z] | Melting point [° C.] | Purity [%] |
|---|---|---|---|---|
| 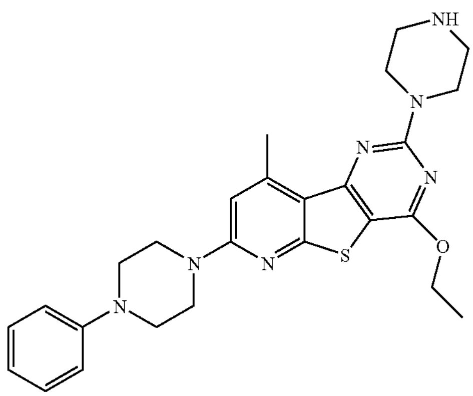 | 489.64 | 490 [M + H]⁺ | 141 | >96 |
| 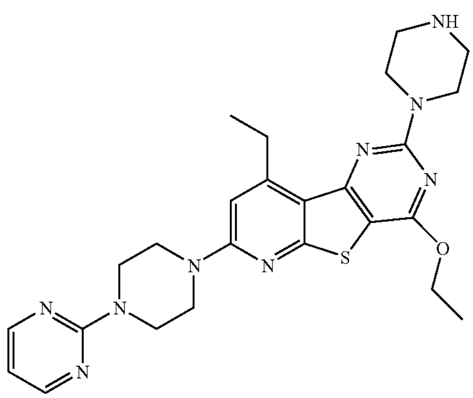 | 505.64 | 506 [M + H]⁺ | 191-192 | >96 |
| | 414.52 | 415 [M + H]⁺ | 153-154 | >95 |
| | 414.52 | 415 [M + H]⁺ | 270 | >96 |

TABLE 11-continued

| Structure | M [g/mol] | MS (ESI) [m/z] | Melting point [° C.] | Purity [%] |
|---|---|---|---|---|
| 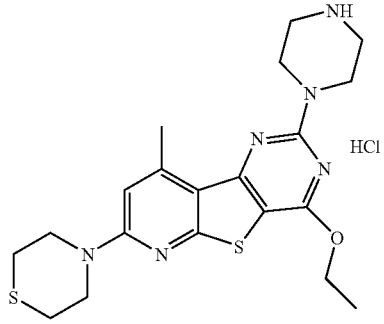 | 467.05 | 461 [M − Cl]+ | 333 | 96 |

Example 23

Studies on the PDE4A Inhibition and Inhibition of TNFα Release

Description of the Methods

The compounds of general formulae 1a, 1b, 1c and 1d are strong inhibitors of phosphodiesterase 4 and/or the release of TNFα.

The posphodiesterase forms having full length were obtained from cytosolic preparations of the human monocytic cell lines U937 or HL60 and partially purified by anion exchange chromatography on a Poros HQ column (strong anion exchanger) in accordance with an adapted method by Lavan B. E., Lakey T., Houslay M. D. *Biochemical Pharmacology*, (1989), 38(22), 4123-4136., and Silver P. J et al., *Eur. J. Pharmacol.* (1988) 150: 85-94, and T. J. Torphy et al., *J. Pharm. Exp. Ther.* (1992), 263: 1195-1205.

Human recombinant PDE-4A catalytic domain comprising amino acids 342-704 was cloned into *Escherichia coli* and expressed, as described by W. Richter et al., *Protein Expression and Purification* (2000) 19: 375-383. The other posphodiesterases were either obtained from cell lines of human origin (TPH1 monocytes line for PDE-1, MCF7 for PDE-5) or expressed recombinantly in sf9 insect cells (for PDE-3A, PDE-3B, PDE-7A and PDE-4D) in accordance with an adapted method by Luckow, V. A. et al., in: *Recombinant DNA Technology & Applications*., (1991) eds. Prokop, Bajpai, R. K. & Ho, C. S., pp 97-152.

The phosphodiesterase activity was determined by the SPA assay as described by the manufacturer Amersham Biosciences and by Horton J. K and Baxendale P. M., *Methods Mol. Biol.* (1995) 41: 91-105.

The reaction mixtures contained 100 mM Tris-HCl (pH 7.5), 5 mM MgCl$_2$, 3.8 mM 2-mercaptoethanol, and 1 µM cAMP or cGMP as a substrate, the inhibitors at different concentrations and also further components required for the detection of the individual isoenzymes (see below). The reaction was started by adding the enzyme. The operating volume is 100 µl in the wells of a white 96-Well microtiter plate. The test substances were produced as stock solutions in DMSO. The DMSO concentration in the reaction batch was 1% v/v. The PDE activity is not impaired with this DMSO concentration. Having started the reaction by the addition of enzyme, the samples were incubated at 22° C. for 20 min. The reaction was stopped by the addition of SPA bead suspension which contains the zinc sulfate concentration provided according to the manufacturer. Then, the beads are allowed to sediment for 30 min and the plates are analyzed on the luminescence microtiter plate reader Fluostar Optima (BMG Labtechologies).

[$^3$H]-cAMP was used as a substrate for determining the activity of PDE-2, -3, -4 and -7 and [$^3$H]-cGMP for determining the activity of PDE-5. The non-specific enzyme activities were determined in the presence of 100 µM rolipram (for PDE-4) and in the presence of 100 µM IBMX (for PDE-3 and -5) and subtracted from the test values. The incubation samples of the PDE-3 assay contain 10 µM rolipram to inhibit possible contaminations by PDE-4. The PDE-2 activity is tested using a SPA assay by Amersham Biosciences in the presence of the PDE-2 activator 5 µM cGMP. IC$_{50}$ values ranging from $10^{-9}$ to $10^{-5}$ M were observed for the inhibitors described in the invention as regards their inhibitory effect on phosphodiesterase 4. The selectivity as to PDEs 2, 3 and 5 has a factor of 100 to 10 000.

Isolated leukocytes can be stimulated for the release of cytokines in different ways. Lipopolysaccharides (LPS) are a stimulus for the investigation of the TNFα release. LPS is part of bacterial cell walls and is released when the bacteria are killed (by antibiotics or the natural immune system). LPS stimulates in particular the activity of phagocytizing leukocytes (tissue macrophages, granulocytes, monocytes) and causes the infiltration of leukocytes from the peripheral blood into the affected tissue. A cytokine of special significance for these mechanisms is TNFα which is secreted in large amounts by the affected cells. The main source are here monocytes and macrophages. TNFα initiates and prolongs the inflammatory process in cooperation with other mediators.

For the investigation of the effect on the LPS-induced TNFα release a method was used which was described by Marx, D., Tassabehji, M., Heer, S., Hüttenbrink, K.-B., and I. Szelenyi, *Pulmonary Pharmacology & Therapeutics* (2002) 15, 7-15. The method is briefly: Human blood was taken from various donors, rendered incoagulable by the addition of 10 mM Na citrate and diluted 1:5 with RPMI 1640 cell culture medium. The test substances were added to the blood samples at various concentrations. 15 min later, the leukocytes were stimulated by the addition of lipopolysaccharides (LPS) from *Salmonella abortus* equi at a final concentration of 1 µg/ml. After the incubation of the test batches at 37° C. and under 5% CO$_2$ in a water-saturated air for 24 h, the blood was centrifuged and the TNFα concentration in the cell-free supernatant was accurately measured using a purchasable ELISA (BD Biosciences) according to the manufacturer's instructions.

The compounds of general formulae 1a, 1b, 1c and 1d are strong inhibitors of phosphodiesterase 4 and the release of TNFalpha. Their in vivo therapeutic potential has been proved by the inhibition of the asthmatic late phase reaction (eosinophilia) in the pulmonary lavage fluid of guinea-pigs and by the influence of the allergy-induced vascular permeability in actively sensitized brown rats (R. Norwegicus).

The below list comprises substances according to the invention of general formulae 1a, 1b, 1c and 1d, which have an $IC_{50}$ value <2 nM in the PDE-4A inhibitory assay:

4-Ethoxy-9-ethyl-7-(4-(pyrimidyl-2-yl)piperazin-1-yl)-2-piperazin-1-yl-pyrido[3',2':4,5]thieno[3,2-d]pyrimidine
4-Ethoxy-9-ethyl-7-(4-methyl-phenyl)-2-(piperazin-1-yl)-pyrido[3',2':4,5]thieno[3,2-d]pyrimidine
2-Ethoxy-9-ethyl-7-(4-methyl-phenyl)-4-(piperazin-1-yl)-pyrido[3',2':4,5]thieno[3,2-d]pyrimidine
4-Ethoxy-7-(4-ethoxy-phenyl)-9-ethyl-2-(piperazin-1-yl)-pyrido[3',2':4,5]thieno[3,2-d]pyrimidine
7-(4-Ethoxy-phenyl)-9-ethyl-2-(piperazin-1-yl)-4-n-propoxy-pyrido[3',2':4,5]thieno[3,2-d]pyrimidine
2-Ethoxy-7-(4-ethoxy-phenyl)-9-ethyl-4-(piperazin-1-yl)-pyrido[3',2':4,5]thieno[3,2-d]pyrimidine
4-Ethoxy-9-ethyl-7-(4-methylthio-phenyl)-2-(piperazin-1-yl)-pyrido[3',2':4,5]thieno[3,2-d]pyrimidine
4-Ethoxy-7-(4-methyl-phenyl)-9-iso-propyl-2-(piperazin-1-yl)-pyrido[3',2':4,5]thieno-[3,2-d]pyrimidine
4-Ethoxy-9-ethyl-7-[4-(4-methoxyphenoxy)phenyl]-2-(piperazin-1-yl)-pyrido[3',2':4,5]thieno[3,2-d]pyrimidine
4-Ethoxy-9-ethyl-7-(2,3-dihydrobenzo[b][1,4]dioxin-6-yl)-2-(piperazin-1-yl)-pyrido[3',2':4,5]thieno[3,2-d]pyrimidine
2-Ethoxy-9-ethyl-7-(2,3-dihydrobenzo[b][1,4]dioxin-6-yl)-4-(piperazin-1-yl)-pyrido[3',2':4,5]thieno[3,2-d]pyrimidine
4-Ethoxy-9-ethyl-7-(3,4-methylenedioxyphenyl)-2-piperazin-1-yl-pyrido[3',2':4,5]thieno-[3,2-d]pyrimidine
4-Ethoxy-7-(4-methoxy-phenyl)-2-(piperazin-1-yl)-9-trifluoromethyl-pyrido[3',2':4,5]thieno[3,2-d]pyrimidine
4-Ethoxy-7-(4-methyl-phenyl)-2-(piperazin-1-yl)-9-trifluoromethyl-pyrido[3',2':4,5]thieno[3,2-d]pyrimidine
7-(2,3-Dihydrobenzo[b][1,4]dioxin-6-yl)-4-ethoxy-2-(piperazin-1-yl)-9-trifluoromethyl-pyrido[3',2':4,5]thieno[3,2-d]pyrimidine
4-Ethoxy-7-(4-(1H-imidazol-1-yl)phenyl)-2-(piperazin-1-yl)-9-trifluoromethyl-pyrido[3',2':4,5]thieno[3,2-d]pyrimidine
4-[4-Ethoxy-2-(piperazin-1-yl)-9-trifluoromethyl-pyrido[3',2':4,5]thieno[3,2-d]pyrimidin-7-yl]-benzoic acid ethyl ester
4-Ethoxy-2-(piperazin-1-yl)-7-(4-(piperidin-1-yl)phenyl)-9-trifluoromethyl-pyrido[3',2':4,5]thieno[3,2-d]pyrimidine
4-Ethoxy-9-ethyl-7-(4-methoxyphenyl)-2-(piperazin-1-yl)-pyrido[3',2':4,5]thieno[3,2-d]pyrimidine
4-Ethoxy-7-(3,4-methylenedioxyphenyl)-2-piperazin-1-yl-9-trifluoromethyl-pyrido[3',2':4,5]thieno-[3,2-d]pyrimidine
4-Ethoxy-7-(4-methylthiophenyl)-2-(piperazin-1-yl)-9-trifluoromethyl-pyrido[3',2':4,5]thieno[3,2-d]pyrimidine
5,6-Dihydro-11-ethoxy-3'-methoxy-9-piperazin-1-yl-7-trifluoromethyl-benzo[h]pyrimido[4',5':4,5]thieno[2,3-b]quinoline
4-Ethoxy-7-(4-(1H-pyrazol-1-yl)-phenyl)-9-ethyl-2-piperazin-1-yl-pyrido[3',2':4,5]thieno[3,2-d]pyrimidine
4-Ethoxy-7-(4-iodo-phenyl)-2-(piperazin-1-yl)-9-trifluoromethyl-pyrido[3',2':4,5]thieno[3,2-d]pyrimidine
4-Ethoxy-7-(4-(1H-pyrazol-1-yl)-phenyl)-2-piperazin-1-yl-9-trifluoromethyl-pyrido[3',2':4,5]thieno[3,2-d]pyrimidine
7-(4-Bromo-phenyl)-4-ethoxy-9-ethyl-2-(piperazin-1-yl)-pyrido[3',2':4,5]thieno[3,2-d]pyrimidine
4-Ethoxy-9-ethyl-7-(4-iodo-phenyl)-2-(piperazin-1-yl)-pyrido[3',2':4,5]thieno[3,2-d]pyrimidine
4-Ethoxy-7-(3-nitro-phenyl)-2-piperazin-1-yl-9-trifluoromethyl-pyrido[3',2':4,5]thieno[3,2-d]pyrimidine
7-(3-Cyano-phenyl)-4-ethoxy-2-piperazin-1-yl-9-trifluoromethyl-pyrido[3',2':4,5]thieno[3,2-d]pyrimidine
N-(4-(4-Ethoxy-9-trifluoromethyl-2-piperazin-1-yl-pyrido[3',2':4,5]thieno[3,2-d]pyrimidin-7-yl)-phenyl)-formamide
N-(4-Ethoxy-9-trifluoromethyl-2-piperazin-1-yl-pyrido[3',2':4,5]thieno[3,2-d]pyrimidin-7-yl)-benzamide trifluoroacetate
N'-Hydroxy-4-(4-ethoxy-9-trifluoromethyl-2-piperazin-1-yl-pyrido[3',2':4,5]thieno[3,2-d]pyrimidin-7-yl)-benzamidine bistrifluoroacetate
N-(4-(4-Ethoxy-9-trifluoromethyl-2-piperazin-1-yl-pyrido[3',2':4,5]thieno[3,2-d]pyrimidin-7-yl)-phenyl)-isonicotinamide
4-Ethoxy-9-trifluoromethyl-2-piperazin-1-yl-7-(4-(1H-pyrrol-1-yl)-phenyl)-pyrido[3',2':4,5]thieno[3,2-d]pyrimidine
N-(4-(4-Ethoxy-9-trifluoromethyl-2-piperazin-1-yl-pyrido[3',2':4,5]thieno[3,2-d]pyrimidin-7-yl)-phenyl)-nicotinamide-N-oxide
4-(4-Ethoxy-9-trifluoromethyl-2-piperazin-1-yl-pyrido[3',2':4,5]thieno[3,2-d]pyrimidin-7-yl)-phenyl-carbamic acid methyl ester
N-(4-(4-Ethoxy-9-trifluoromethyl-2-piperazin-1-yl-pyrido[3',2':4,5]thieno[3,2-d]pyrimidin-7-yl)-phenyl)-nicotinamide
7-(3'-Aminobiphen-4-yl)-4-ethoxy-9-methyl-2-piperazin-1-yl-thieno[2,3-d:4,5-d']dipyrimidine
4-Ethoxy-7-(4-[3-furyl]-phenyl)-9-methyl-2-piperazin-1-yl-thieno[2,3-d:4,5-d']dipyrimidine
4-Ethoxy-7-(4-[2-furyl]-phenyl)-9-methyl-2-piperazin-1-yl-thieno[2,3-d:4,5-d']dipyrimidine
4-Ethoxy-9-methyl-2-piperazin-1-yl-7-(4-[3-pyridyl]-phenyl)-thieno[2,3-d:4,5-d']dipyrimidine
4-Ethoxy-9-methyl-2-piperazin-1-yl-7-(4-[4-pyridyl]-phenyl)-thieno[2,3-d:4,5-d']dipyrimidine
7-(4'-Aminobiphen-4-yl)-4-ethoxy-9-methyl-2-piperazin-1-yl-thieno[2,3-d:4,5-d']dipyrimidine
4-Ethoxy-9-methyl-2-piperazin-1-yl-7-(3',4',5'-trimethoxy-biphen-4-yl)-thieno[2,3-d:4,5-d']dipyrimidine
4-Ethoxy-9-methyl-7-(4-phenoxy-phenyl)-2-piperazin-1-yl-thieno[2,3-d:4,5-d']dipyrimidine
2'-Amino-4-(4-ethoxy-9-methyl-2-piperazin-1-yl-thieno[2,3-d:4,5-d']dipyrimidin-7-yl)-biphenyl-4'-carboxylic acid methyl ester
7-(3',4'-Dimethoxybiphen-4-yl)-4-ethoxy-9-methyl-2-piperazin-1-yl-thieno[2,3-d:4,5-d']dipyrimidine
7-(4-[3,5-Dimethyl-isoxazol-4-yl]-phenyl)-4-ethoxy-9-methyl-2-piperazin-1-yl-thieno[2,3-d:4,5-d']dipyrimidine The below list comprises substances according to the invention of general formulae 1a, 1b, 1c and 1d which has an $IC_{50}$ value of 2-50 nM in the PDE-4A inhibitory assay:

4-Ethoxy-9-methyl-2-piperazin-1-yl-7-(4-[3-pyrrolyl]-phenyl)-thieno[2,3-d:4,5-d']dipyrimidine
7-(4-[1,2-Dihydroxyethyl]-phenyl)-4-ethoxy-9-methyl-2-piperazin-1-yl-thieno[2,3-d:4,5-d']dipyrimidine 4-Ethoxy-9-methyl-7-phenyl-2-piperazin-1-yl-thieno[2,3-d:4,5-d']dipyrimidine 4-Ethoxy-9-methyl-2-piperazin-1-yl-7-(4-vinyl-phenyl)-thieno[2,3-d:4,5-d']dipyrimidine 4-Ethoxy-9-methyl-2-piperazin-1-yl-7-(4-[N—BOC-3-pyrrolyl]-phenyl)-thieno[2,3-d:4,5-d']dipyrimidine 7-(4-Bromo-phenyl)-4-ethoxy-9-methyl-2-piperazin-1-yl-thieno[2,3-d:4,5-d']dipyrimidine 7-(4-tert-Butyl-phenyl)-4-ethoxy-9-methyl-2-piperazin-1-yl-thieno[2,3-d:4,5-d']dipyrimidine 4-Ethoxy-9-methyl-2-piperazin-1-yl-7-(4-iso-propoxy-phenyl)-thieno[2,3-d:4,5-d']dipyrimidine 4-Ethoxy-9-methyl-2-piperazin-1-yl-7-(4-[5-pyrimidinyl]-phenyl)-thieno[2,3-d:4,5-d']dipyrimidine 7-(4-[4-n-Butoxy-phenoxy]phenyl)-4-ethoxy-9-methyl-2-piperazin-1-yl-thieno[2,3-d:4,5-d']dipyrimidine 7-Benzyl-4-ethoxy-9-methyl-2-piperazin-1-yl-thieno[2,3-d:4,5-d']dipyrimidine 4-Ethoxy-7-(4-methoxy-phenyl)-9-methyl-2-piperazin-1-yl-thieno[2,3-d:4,5-d']dipyrimidine 4-Ethoxy-9-methyl-7-(1-naphthyl)-2-piperazin-1-yl-thieno[2,3-d:4,5-d']dipyrimidine 7-(4-Biphenyl)-4-ethoxy-9-methyl-2-piperazin-1-yl-thieno[2,3-d:4,5-d']dipyrimidine 4-Ethoxy-7-(4-[hydroxy{3-pyridyl}methyl]-phenyl)-9-methyl-2-piperazin-1-yl-thieno[2,3-d:4,5-d']dipyrimidine 4-(4-Ethoxy-9-methyl-2-piperazin-1-yl-thieno[2,3-d:4,5-d']dipyrimidin-7-yl)-biphenyl-4'-carboxylic acid sodium salt 2'-Amino-4-(4-ethoxy-9-methyl-2-piperazin-1-yl-thieno[2,3-d:4,5-d']dipyrimidin-7-yl)-biphenyl-4'-carboxylic acid sodium salt 4-(4-Ethoxy-9-methyl-2-piperazin-1-yl-thieno[2,3-d:4,5-d']dipyrimidin-7-yl)-biphenyl-3'-carboxylic acid methyl ester 4-(4-Ethoxy-9-methyl-2-piperazin-1-yl-thieno[2,3-d:4,5-d']dipyrimidin-7-yl)-biphenyl-3'-carboxylic acid potassium salt 4-(4-Ethoxy-9-methyl-2-piperazin-1-yl-thieno[2,3-d:4,5-d']dipyrimidin-7-yl)-biphenyl-4'-carboxylic acid ethyl ester 4-Ethoxy-9-methyl-7-morpholino-2-(piperazin-1-yl)-pyrido[3',2':4,5]thieno[3,2-d]pyrimidine 2-Ethoxy-9-methyl-7-morpholino-4-(piperazin-1-yl)-pyrido[3',2':4,5]thieno[3,2-d]pyrimidine 4-Ethoxy-9-ethyl-7-(4-phenyl-piperazin-1-yl)-2-piperazin-1-yl-pyrido[3',2':4,5]thieno[3,2-d]pyrimidine 4-Ethoxy-9-methyl-7-thiomorpholino-2-(piperazin-1-yl)-pyrido[3',2':4,5]thieno[3,2-d]pyrimidine-hydrochloride 2-Ethoxy-9-ethyl-7-(4-methyl-phenyl)-4-(piperazin-1-yl)-pyrido[3',2':4,5]thieno[3,2-d]pyrimidine 2-(2-Hydroxy-ethoxy)-9-ethyl-7-(4-methyl-phenyl)-4-(piperazin-1-yl)-pyrido[3',2':4,5]thieno[3,2-d]pyrimidine 7-(4-Ethoxy-phenyl)-9-ethyl-4-(piperazin-1-yl)-2-n-propoxy-pyrido[3',2':4,5]thieno[3,2-d]pyrimidine 9-iso-Butyl-4-ethoxy-7-(4-methyl-phenyl)-2-(piperazin-1-yl)-pyrido[3',2':4,5]thieno-[3,2-d]pyrimidine 7-(4-Chloro-phenyl)-9-ethyl-4-ethoxy-2-(piperazin-1-yl)-pyrido[3',2':4,5]thieno[3,2-d]pyrimidine 4-Ethoxy-7-(4-morpholinophenyl)-2-(piperazin-1-yl)-9-trifluoromethyl-pyrido[3',2':4,5]thieno[3,2-d]pyrimidine 4-Ethoxy-2-(piperazin-1-yl)-7-(4-pyridyl)-9-trifluoromethyl-pyrido[3',2':4,5]thieno[3,2-d]pyrimidine 4-Ethoxy-7-(1-oxy-pyridin-4-yl)-2-(piperazin-1-yl)-9-trifluoromethyl-pyrido[3',2':4,5]thieno[3,2-d]pyrimidine 4-(2-Hydroxy-ethoxy)-7-[(1H-imidazol-1-yl)phenyl]-2-(piperazin-1-yl)-9-trifluoromethyl-pyrido[3',2':4,5]thieno[3,2-d]pyrimidine 4-Ethoxy-9-methyl-7-(3,4-methylenedioxyphenyl)-2-piperazin-1-yl-pyrido[3',2':4,5]thieno-[3,2-d]pyrimidine 2-Ethoxy-9-methyl-7-(3,4-methylenedioxyphenyl)-4-piperazin-1-yl-pyrido[3',2':4,5]thieno-[3,2-d]pyrimidine 4-Ethoxy-7-(4-methoxy-phenyl)-9-methyl-8-(4-nitro-benzyl)-2-(piperazin-1-yl)-pyrido[3',2':4,5]thieno[3,2-d]pyrimidine 7-(4-Bromo-phenyl)-4-ethoxy-9-methyl-2-(piperazin-1-yl)-pyrido[3',2':4,5]thieno[3,2-d]pyrimidine 4-Ethoxy-7-(4-nitro-phenyl)-2-piperazin-1-yl-9-trifluoromethyl-pyrido[3',2':4,5]thieno[3,2-d]pyrimidine 7-(4-Amino-phenyl)-4-ethoxy-2-piperazin-1-yl-9-trifluoromethyl-pyrido[3',2':4,5]thieno[3,2-d]pyrimidine 9-Difluoromethyl-7-(4-chloro-phenyl)-4-ethoxy-2-piperazin-1-yl-pyrido[3',2':4,5]thieno[3,2-d]pyrimidine 7-(4-Cyano-phenyl)-4-ethoxy-2-piperazin-1-yl-9-trifluoromethyl-pyrido[3',2':4,5]thieno[3,2-d]pyrimidine 4-Ethoxy-9-methyl-7-(4-methylthio-phenyl)-2-piperazin-1-yl-pyrido[3',2':4,5]thieno[3,2-d]pyrimidine 4-Ethoxy-7-(4-fluoro-phenyl)-2-piperazin-1-yl-9-trifluoromethyl-pyrido[3',2':4,5]thieno[3,2-d]pyrimidine 4-Ethoxy-2-piperazin-1-yl-9-trifluoromethyl-7-(3,4,5-trimethoxy-phenyl)-pyrido[3',2':4,5]thieno[3,2-d]pyrimidine 7-(3-Amino-phenyl)-4-Ethoxy-2-piperazin-1-yl-9-trifluoromethyl-pyrido[3',2':4,5]thieno[3,2-d]pyrimidine 4-Ethoxy-7-[4-(4-nitrobenzyloxy)-phenyl]-2-piperazin-1-yl-9-trifluoromethyl-pyrido[3',2':4,5]thieno[3,2-d]pyrimidine 4-Ethoxy-2-piperazin-1-yl-7-(3-pyridyl)-9-trifluoromethyl-pyrido[3',2':4,5]thieno[3,2-d]pyrimidine 4-Ethoxy-7-(1-oxy-pyridin-3-yl)-2-(piperazin-1-yl)-9-trifluoromethyl-pyrido[3',2':4,5]thieno[3,2-d]pyrimidine 4-Ethoxy-2-piperazin-1-yl-7-(2-pyridyl)-9-trifluoromethyl-pyrido[3',2':4,5]thieno[3,2-d]pyrimidine 2-Ethoxy-7-phenyl-9-methyl-4-(piperazin-1-yl)-pyrido[3',2':4,5]furo[3,2-d]pyrimidine 9-Methyl-7-phenyl-4-piperazin-1-yl-2-n-propoxy-pyrido[3',2':4,5]thieno[3,2-d]pyrimidine 9-Methyl-7-phenyl-2-piperazin-1-yl-4-(1,1,1-trifluoroethoxy)-pyrido[3',2':4,5]thieno[3,2-d]pyrimidine 4-Ethoxy-7-morpholino-9-phenyl-2-(piperazin-1-yl)-pyrido[3',2':4,5]thieno[3,2-d]pyrimidine 4-Ethoxy-7-(4-trifluoro-methyl-phenyl)-9-methyl-2-(piperazin-1-yl)-pyrido[3',2':4,5]thieno[3,2-d]pyrimidine 8-(4-Amino-benzyl)-4-ethoxy-7,9-dimethyl-2-(piperazin-1-yl)-pyrido[3',2':4,5]thieno[3,2-d]pyrimidine 4-(2,2-Difluoro-ethoxy)-9-methyl-7-phenyl-2-(piperazin-1-yl)-pyrido[3',2':4,5]thieno[3,2-d]pyrimidine 9-Methyl-7-phenyl-2-(piperazin-1-yl)-4-n-propoxy-pyrido[3',2':4,5]thieno[3,2-d]pyrimidine 4-Ethoxy-7-thien-2-yl-9-trifluoro-methyl-2-(piperazin-1-yl)-pyrido[3',2':4,5]thieno[3,2-d]pyrimidine 2-Ethoxy-7-(4-trifluoro-methyl-phenyl)-9-methyl-4-(piperazin-1-yl)-pyrido[3',2':4,5]thieno[3,2-d]pyrimidine 2-(2-Hydroxy-ethoxy)-9-methyl-7-phenyl-4-(piperazin-1-yl)-pyrido[3',2':4,5]thieno[3,2-d]pyrimidine 2-Ethoxy-7-methyl-9-phenyl-4-(piperazin-1-yl)-pyrido[3',2':4,5]thieno[3,2-d]pyrimidine 4-Ethoxy-7-(4-methoxy-phenyl)-9-methyl-2-(piperazin-1-yl)-pyrido[3',2':4,5]thieno[3,2-d]pyrimidine 4-Ethoxy-7-phenyl-9-methyl-2-(piperazin-1-yl)-pyrido[3',2':4,5]furo[3,2-d]pyrimidine 2-(2,2-Difluoro-ethoxy)-9-methyl-7-phenyl-4-(piperazin-1-yl)-pyrido[3',2':4,5]thieno[3,2-d]pyrimidine 2-Ethoxy-7,9-di-iso-propyl-4-(piperazin-1-yl)-pyrido[3',2':4,5]thieno[3,2-d]pyrimidine 7-(3,4-Dimethoxy-phenyl)-9-methyl-4-(piperazin-1-yl)-2-n-propyl-pyrido[3',2':4,5]thieno[3,2-d]pyrimidine 2-Ethoxy-9-methyl-7-(4-methyl-phenyl)-4-(piperazin-1-yl)-pyrido[3',2':4,5]thieno[3,2-d]pyrimidine 9-Methyl-7-phenyl-2-(piperazin-1-yl)-4-iso-propoxy-pyrido[3',2':4,5]thieno[3,2-d]pyrimidine 4-(2-Hydroxy-ethoxy)-9-methyl-7-phenyl-2-(piperazin-1-yl)-pyrido[3',2':4,5]thieno[3,2-d]pyrimidine 2-Ethoxy-7-thien-2-yl-9-trifluoro-methyl-4-(piperazin-1-yl)-pyrido[3',2':4,5]thieno[3,2-d]pyrimidine 2-Ethoxy-7-(3,4-dimethoxy-phenyl)-9-methyl-4-(piperazin-1-yl)-pyrido[3',2':4,5]thieno[3,2-d]pyrimidine 2-Ethoxy-7-(4-methoxy-phenyl)-9-methyl-4-(piperazin-1-yl)-pyrido[3',2':4,5]thieno[3,2-d]pyrimidine 2-Ethoxy-9-methyl-7-thien-2-yl-9-methyl-4-(piperazin-1-yl)-pyrido[3',2':4,5]thieno[3,2-d]pyrimidine 4-Ethoxy-9-methyl-7-(4-methyl-phenyl)-2-(piperazin-1-yl)-pyrido[3',2':4,5]thieno[3,2-d]pyrimidine 4-Ethoxy-7,9-dimethyl-8-(4-nitro-benzyl)-2-(piperazin-1-yl)-pyrido[3',2':4,5]thieno[3,2-d]pyrimidine 4-Ethoxy-7-(4-fluoro-phenyl)-9-methyl-2-(piperazin-1-yl)-pyrido[3',2':4,5]thieno[3,2-d]pyrimidine 2-Ethoxy-7,9-dimethyl-8-(4-nitro-benzyl)-4-(piperazin-1-yl)-pyrido[3',2':4,5]thieno[3,2-d]pyrimidine 4-Ethoxy-7,9-diphenyl-2-(piperazin-1-yl)-pyrido[3',2':4,5]thieno[3,2-d]pyrimidine 4-Ethoxy-7-methyl-9-phenyl-2-(piperazin-1-yl)-pyrido[3',2':4,5]thieno[3,2-d]pyrimidine 2-Ethoxy-9-trifluoro-methyl-7-phenyl-4-(piperazin-1-yl)-pyrido[3',2':4,5]thieno[3,2-d]pyrimidine 4-Ethoxy-7,9-di-iso-propyl-2-(piperazin-1-yl)-pyrido[3',2':4,5]thieno[3,2-d]pyrimidine 9-Methyl-7-phenyl-4-(piperazin-1-yl)-2-iso-propoxy-pyrido[3',2':4,5]thieno[3,2-d]pyrimidine 9-Methyl-7-phenyl-4-(piperazin-1-yl)-2-n-propyl-pyrido[3',2':4,5]thieno[3,2-d]pyrimidine 4-Ethoxy-9-methyl-8-(4-nitro-benzyl)-7-phenyl-2-(piperazin-1-yl)-pyrido[3',2':4,5]thieno[3,2-d]pyrimidine 4-Ethoxy-9-methyl-7-thien-2-yl-2-(piperazin-1-yl)-pyrido[3',2':4,5]thieno[3,2-d]pyrimidine 4-Ethoxy-9-trifluoro-methyl-7-phenyl-2-(piperazin-1-yl)-pyrido[3',2':4,5]thieno[3,2-d]pyrimidine 4-(2,2-Difluoro-ethoxy)-9-methyl-7-phenyl-2-(piperazin-1-yl)-pyrido[3',2':4,5]thieno-[3,2-d]pyrimidine 4-Ethoxy-7-(3,4-dimethoxy-phenyl)-9-methyl-2-(piperazin-1-yl)-pyrido[3',2':4,5]thieno-[3,2-d]pyrimidine 8-Ethoxy-5-morpholino-10-piperazin-1-yl-pyrimido[4',5':4,5]thieno[2,3-c]-1,2,3,4-tetrahydro-isoquinoline 8-Ethoxy-5-(N-methyl-piperazin-1-yl)-10-piperazin-1-yl-pyrimido[4',5':4,5]thieno[2,3-c]-1,2,3,4-tetrahydro-isoquinoline 7-Ethoxy-2,3-dihydro-4-morpholino-9-piperazin-1yl-1H-cyclopenta[4',5']pyrido[3',2':4,5]thieno[3,2-d]pyrimidine 8-Ethoxy-5-piperidino-10-piperazin-1-yl-pyrimido[4',5':4,5]thieno[2,3-c]-1,2,3,4-tetrahydro-isoquinoline-hydrochloride 8-Ethoxy-5-phenyl-10-piperazin-1-yl-pyrimido[4',5':4,5]thieno[2,3-c]-1,2,3,4-tetrahydro-isoquinoline-hydrochloride 10-Ethoxy-5-phenyl-8-piperazin-1-yl-pyrimido[4',5':4,5]thieno[2,3-c]-1,2,3,4-tetrahydro-isoquinoline 8-Ethoxy-3-methyl-5-morpholino-10-piperazin-1-yl-pyrimido[4',5':4,5]thieno[2,7]-1,2,3,4-tetrahydro-naphthyridine 9-Ethoxy-6-morpholino-11-(piperazin-1-yl)-2,3,4,5-tetrahydro-1H-cyclohepta[4',5']pyrido[3',2':4,5]thieno[3,2-d]pyrimidine The TNFα release inhibition of selected compounds of general formulae 1a, 1b, 1c and 1d was determined. The below list comprises substances according to the invention which have an $IC_{50}$ value of <2 µM in the TNFα inhibitory assay:

7-(3'-Aminobiphen-4-yl)-4-ethoxy-9-methyl-2-piperazin-1-yl-thieno[2,3-d:4,5-d']dipyrimidine 4-Ethoxy-7-(4-[3-furyl]-phenyl)-9-methyl-2-piperazin-1-yl-thieno[2,3-d:4,5-d']dipyrimidine 4-Ethoxy-9-methyl-2-piperazin-1-yl-7-(4-[3-pyrrolyl]-phenyl)-thieno[2,3-d:4,5-d']dipyrimidine 7-(4-[1,2-Dihydroxyethyl]-phenyl)-4-ethoxy-9-methyl-2-piperazin-1-yl-thieno[2,3-d:4,5-d']dipyrimidine 4-Ethoxy-7-(3,4-dimethoxy-phenyl)-9-methyl-2-(piperazin-1-yl)-pyrido[3',2':4,5]thieno[3,2-d]pyrimidine 4-Ethoxy-7-(4-methoxy-phenyl)-9-methyl-2-(piperazin-1-yl)-pyrido[3',2':4,5]thieno[3,2-d]pyrimidine-hydrochloride 2-Ethoxy-7-methyl-9-phenyl-4-(piperazin-1-yl)-pyrido[3',2':4,5]thieno[3,2-d]pyrimidine-hydrochloride 2-Ethoxy-7-(4-trifluoro-methyl-phenyl)-9-methyl-4-(piperazin-1-yl)-pyrido[3',2':4,5]thieno[3,2-d]pyrimidine 2-(2-Hydroxy-ethoxy)-9-methyl-7-phenyl-4-(piperazin-1-yl)-pyrido[3',2':4,5]thieno[3,2-d]pyrimidine 8-(4-Amino-benzyl)-4-ethoxy-7,9-dimethyl-2-(piperazin-1-yl)-pyrido[3',2':4,5]thieno[3,2-d]pyrimidine 4-Ethoxy-7-(3,4-dimethoxy-phenyl)-9-methyl-2-(piperazin-1-yl)-pyrido[3',2':4,5]thieno[3,2-d]pyrimidine-hydrochloride 4-Ethoxy-7-morpholino-9-phenyl-2-(piperazin-1-yl)-pyrido[3',2':4,5]thieno[3,2-d]pyrimidine 2-Ethoxy-7-(3,4-dimethoxy-phenyl)-9-methyl-4-(piperazin-1-yl)-pyrido[3',2':4,5]thieno[3,2-d]pyrimidine 2-Ethoxy-7-(4-methoxy-phenyl)-9-methyl-4-(piperazin-1-yl)-pyrido[3',2':4,5]thieno[3,2-d]pyrimidine 2-Ethoxy-7,9-dimethyl-8-(4-nitro-benzyl)-4-(piperazin-1-yl)-pyrido[3',2':4,5]thieno[3,2-d]pyrimidine 4-Ethoxy-7,9-diphenyl-2-(piperazin-1-yl)-pyrido[3',2':4,5]thieno[3,2-d]pyrimidine 4-Ethoxy-7-(4-methoxy-phenyl)-9-methyl-2-(piperazin-1-yl)-pyrido[3',2':4,5]thieno[3,2-d]pyrimidine 9-Methyl-7-phenyl-2-(piperazin-1-yl)-4-n-propoxy-pyrido[3',2':4,5]thieno[3,2-d]pyrimidine 4-Ethoxy-7,9-dimethyl-8-(4-nitro-benzyl)-2-(piperazin-1-yl)-pyrido[3',2':4,5]thieno[3,2-d]pyrimidine 4-Ethoxy-7-(4-fluoro-phenyl)-9-methyl-2-(piperazin-1-yl)-pyrido[3',2':4,5]thieno[3,2-d]pyrimidine 4-Ethoxy-2-piperazin-1-yl-7-(3-pyridyl)-9-trifluoromethyl-pyrido[3',2':4,5]thieno[3,2-d]pyrimidine 4-Ethoxy-7-(1-oxy-pyridin-3-yl)-2-(piperazin-1-yl)-9-trifluoromethyl-pyrido[3',2':4,5]thieno[3,2-d]pyrimidine 4-Ethoxy-2-piperazin-1-yl-7-(4-pyridyl)-9-trifluoromethyl-pyrido[3',2':4,5]thieno[3,2-d]pyrimidine 4-Ethoxy-7-(1-oxy-pyridin-4-yl)-2-(piperazin-1-yl)-9-trifluoromethyl-pyrido[3',2':4,5]thieno[3,2-d]pyrimidine 4-Ethoxy-7-(4-(1H-imidazol-1-yl)phenyl)-2-(piperazin-1-yl)-9-trifluoromethyl-pyrido[3',2':4,5]thieno[3,2-d]pyrimidine 4-(2-Hydroxy-ethoxy)-7-[(1H-imidazol-1-yl)phenyl]-2-(piperazin-1-yl)-9-trifluoromethyl-pyrido[3',2':4,5]thieno[3,2-d]pyrimidine 8-Ethoxy-5-morpholino-10-piperazin-1-yl-pyrimido[4',5':4,5]thieno[2,3-c]-1,2,3,4-tetrahydro-isoquuinoline 4-(4-Ethoxy-9-trifluoromethyl-2-piperazin-1-yl-pyrido[3',2':4,5]thieno[3,2-d]pyrimidin-7-yl)-benzamide trifluoroacetate N'-Hydroxy-4-(4-ethoxy-9-trifluoromethyl-2-piperazin-1-yl-pyrido[3',2':4,5]thieno[3,2-d]pyrimidin-7-yl)-benzamidine bistrifluoroacetate 4-Ethoxy-9-trifluoromethyl-2-piperazin-1-yl-7-(4-(1H-1,2,4-triazol-4-yl)-phenyl)-pyrido[3',2':4,5]thieno[3,2-d]pyrimidine N-(4-(4-Ethoxy-9-trifluoromethyl-2-piperazin-1-yl-pyrido[3',2':4,5]thieno[3,2-d]pyrimidin-7-yl)-phenyl)-isonicotinamide N-(4-(4-Ethoxy-9-trifluoromethyl-2-piperazin-1-yl-pyrido[3',2':4,5]thieno[3,2-d]pyrimidin-7-yl)-phenyl)-formamide N-(4-(4-Ethoxy-9-trifluoromethyl-2-piperazin-1-yl-pyrido[3',2':4,5]thieno[3,2-d]pyrimidin-7-yl)-phenyl)-nicotinamide

Example 24

Use of PDE Inhibitors for Axonal Regeneration

A number of compounds according to the invention were test for the indication "axonal degeneration". Axonal regeneration, i.e. functional restoration of nerve tracts (axons), is a therapy target wherever severe injuries of the central nervous system (brain and spinal marrow) occurred as a result of mechanical influences. For the time being there are no successful therapeutic techniques serving for restoring injuries of the central nervous system where nerve tracts were cut through. Surgery of spinal traumas is limited to the restoration of the normal shape of the spinal column and optionally to the exposure of the spinal canal for supporting the autoregeneration of the nerve tracts. However, most of the severe CNS injuries end in a lifelong loss of the function of the whole body region.

A completely novel approach for the regeneration of cut-through nerve tracts is based on the topical use of PDE-4 inhibitors. This case uses the circumstance that the axonal nerve growth is initiated via a cAMP-dependent signal transduction cascade. If the intracellular cAMP level exceeds a certain threshold value, neurite growth is induced. Pharmacologically, a sufficient increase in the intracellular cAMP level can be achieved by inhibiting phosphodiesterase-4, the enzyme which is predominantly responsible for cAMP degradation.

The successful use of the prototype PDE-4 inhibitor rolipram in rats for the functional restoration of the spinal marrow following an experimental nerve injury was recently described in two studies (Nikulina, E., Tidwell, J. L., Dai, H. N., Bregman, B. S., and Filbin, M. T. (2004), Proc. Nat. Acad. Sci. USA 101(23), pp. 8786-8790; Pearse, D. D., Pereira, F. C., Marcillo, A. E., Bates, M. L., Berrocal, Y. A., Filbin, M. T. and Bunge, M. B. (2004), Nat. Med. 10(6), pp. 610-616).

Figure 1B:
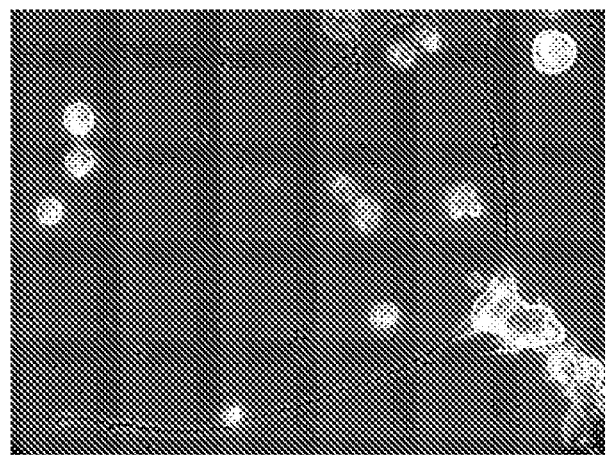

The inventors have tested some PDE4 inhibitors according to the invention for induction of axon growth with the murine neuroblastoma cell line N2a. It turned out that in particular the substances 4-ethoxy-9-ethyl-7-(3,4-methylenedioxyphenyl)-2-piperazin-1-yl-pyrido[3',2':4,5]thieno[3,2-d]-pyrimidine and 7-(3,4-dimethoxyphenyl)-4-ethoxy-9-methyl-2-piperazin-1-yl-pyrido[3',2':4,5]thieno[3,2-d]pyrimidine hydrochloride were able to induce the growth of long processes ("axons") having a length of up to 300 μM at concentrations of 1 μM in the test batch after 72 h (FIGS. 1a and 1b).

Example 25

Use of PDE4 Inhibitors for the Induction of Apoptosis in Chronic Lymphatic Leukemia (CLL)

In addition, the inventors tested compounds according to the invention as PDE4 inhibitors for induction of a cytotoxic reaction, i.e. triggering of apoptosis, in the case of chronic lymphatic leukemia (CLL).

According to recent findings, phosphodiesterase 4 is also a valid therapeutic target for treating CLL.

Chronic lymphatic leukemia of the B-cells is a hardly curable, clonal disease which responds to chemotherapeutic agents (cytostatics). Many patients, however, develop what is called chemoresistance to these medicaments.

Since the 70ies, it has been observed that an increase in the intracellular cyclic adenosine monophosphate (cAMP) results in a selective apoptosis induction in malignant CLL cells as compared to healthy T and B lymphocytes (V. Daniel et al., Proc Natl Acad Sci 70: 76; 1973). cAMP analogues which pass through the membrane (dibutyryl cAMP), adenylatecyclase activators (forskolin) and inhibitors of phosphodiesterase PDE-3 (cilostamides) and PDE4 (rolipram), as such or in combination, resulted in a caspase-dependent apoptosis in CLL lymphocytes. Rolipram treatment suppresses the expression of the anti-apoptosis member of the Bcl-2 family and induces the pro-apoptosis protein Bax (E Moon et al., Clin Cancer Res 8: 589 (2002); S B Welsch et al., Leukemia 15: 1564 (2001)).

In order to explore the issue whether Applicant's selective PDE-4 inhibitors can also induce a selective apoptosis of CLL lymphocytes, the compounds according to the invention were tested at a concentration of 1 μM with patients suffering from a primary CLL.

The positive control used was fludarabine which is employed for CLL as a standard chemotherapeutic agent. A cytotoxicity up to a maximum of 60% under equal test conditions, in a cAMP-independent route, was achieved with fludarabine.

The cytotoxicity of the CLL cells was determined by means of a commercially available formazan reduction assay (MTT test) after 24 h of incubation of the patient's blood with the active substances.

The phosphodiesterase activity of recombinant human PDE-4A, PDE-4B and PDE-4D, which were expressed in sf9 insect cells, was determined by means of a scintillation proximity assay in accordance with the manufacturer's instructions. The lipopolysaccharide(LPS)-dependent release of the tumor necrosis factor-α (TNFα) by mononuclear cells in dilute human whole blood was determined by means of a sandwich TNFα ELISA.

The following list shows a selection of the substances according to the invention which trigger cytotoxicity in 60%-85% of the cells:

4-Ethoxy-7-(4-[2-furyl]-phenyl)-9-methyl-2-piperazin-1-yl-thieno[2,3-d:4,5-d']dipyrimidine 4-Ethoxy-9-methyl-2-piperazin-1-yl-7-(4-[N—BOC-3-pyrrolyl]-phenyl)-thieno[2,3-d:4,5-d']dipyrimidine 4-Ethoxy-9-ethyl-7-(4-methyl-phenyl)-2-(piperazin-1-yl)-pyrido[3',2':4,5]thieno[3,2-d]pyrimidine 2-Ethoxy-7-(4-methyl-phenyl)-4-(piperazin-1-yl)-9-propyl-pyrido[3',2':4,5]thieno[3,2-d]pyrimidine 2-Ethoxy-7-(4-methyl-phenyl)-4-(piperazin-1-yl)-9-propyl-pyrido[3',2':4,5]thieno[3,2-d]pyrimidine hydrochloride 2-Ethoxy-9-methyl-4-(piperazin-1-yl)-7-phenyl-pyrido[3',2':4,5]furo[3,2-d]pyrimidine 7-(2,3-Dihydrobenzo[b][1,4]dioxin-6-yl)-2-ethoxy-9-ethyl-4-piperazino-pyrido[3',2':4,5]thieno[3,2-d]pyrimidine 4-Ethoxy-9-ethyl-7-(4-methoxy-phenyl)-2-piperazin-1-yl-pyrido[3',2':4,5-d]pyrimidine hydrochloride 4-Ethoxy-7-(4-methylthio-phenyl)-2-piperazin-1-yl-9-trifluoromethyl-pyrido[3',2':4,5]thieno[3,2-d]pyrimidine Mono-[4-Ethoxy-7-(4-methylthio-phenyl)-2-piperazin-1-yl-9-trifluoromethyl-pyrido[3',2':4,5]thieno[3,2-d]pyrimidine]citrate 7-(4-Amino-phenyl)-4-ethoxy-2-piperazin-1-yl-9-trifluoromethyl-pyrido[3',2':4,5]thieno[3,2-d]pyrimidine 4-Ethoxy-9-methyl-2-piperazin-1-yl-7-(4-[4-pyridyl]-phenyl)-thieno[2,3-d:4,5-d']dipyrimidine 4-Ethoxy-9-methyl-2-piperazin-1-yl-7-(4-[3-pyridyl]-phenyl)-thieno[2,3-d:4,5-d']dipyrimidine 4-Ethoxy-9-methyl-2-piperazin-1-yl-7-(4-[3-pyrrolyl]-phenyl)-thieno[2,3-d:4,5-d']dipyrimidine 4-(4-Ethoxy-9-methyl-2-piperazin-1-yl-thieno[2,3-d:4,5-d']dipyrimidin-7-yl)-biphenyl-3'-carboxylic acid potassium salt 7-(4'-Aminobiphen-4-yl)-4-ethoxy-9-methyl-2-piperazin-1-yl-thieno[2,3-d:4,5-d']dipyrimidine 4-Ethoxy-9-methyl-2-piperazin-1-yl-7-(4-[5-pyrimidinyl]-phenyl)-thieno[2,3-d:4,5-d']dipyrimidine 7-(3',4'-Dimethoxybiphen-4-yl)-4-ethoxy-9-methyl-2-piperazin-1-yl-thieno[2,3-d:4,5-d']dipyrimidine 4-Ethoxy-7-(4-methoxy-phenyl)-9-methyl-2-piperazin-1-yl-pyrido[3',2':4,5]thieno[3,2-d]pyrimidine 2-Ethoxy-9-methyl-7-(3,4-methylenedioxy-phenyl)-4-piperazin-1-yl-pyrido[3',2':4,5]-thieno[3,2-d]pyrimidine 4-Ethoxy-9-ethyl-7-(4-methoxy-phenyl)-2-piperazin-1-yl-pyrido[3',2':4,5]thieno[3,2-d]pyrimidine

The invention claimed is:
1. A pharmaceutical composition comprising at least one compound of general formula 1(a)(I) or 1(a)(II):

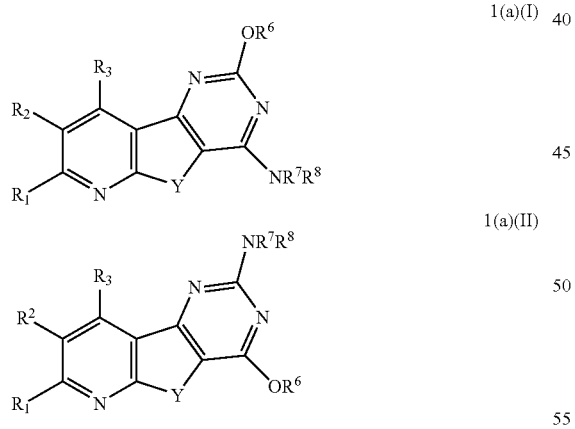

wherein
Y is S, O or N—H
$R^1$ is
hydrogen,
$C_{1-10}$ alkyl, —$C_{2-12}$ alkenyl, —$C_{2-12}$ alkinyl, each straight-chain, branched or cyclic and, where appropriate, substituted singly, doubly or triply with independently selected residues $R^§$,
aralkyl- having $C_{6-12}$ aryl and $C_{1-5}$ alkyl, substituted, where appropriate, singly, doubly or triply with independently selected residues $R^§$, phenyl, substituted, where appropriate, singly, doubly or triply with independently selected residues $R^§$,
1-naphthyl, 2-naphthyl,
pyridyl-N-oxide, (substituted, where appropriate, with $R^§$),
monocyclic or bicyclic, saturated or singly or multiply unsaturated heterocycles having 5-14 ring atoms, including 1-4 heteroatoms which are preferably N, O and S, substituted, where appropriate, singly, doubly or triply with independently selected residues $R^§$,
$C_{1-10}$ alkoxy, straight-chain, branched or cyclic as well as substituted, where appropriate, singly, doubly or triply with independently selected residues $R^§$,
aralkyloxy- having $C_{6-12}$ aryl and $C_{1-5}$ alkyl, substituted, where appropriate, singly, doubly or triply with independently selected residues $R^§$,
$C_{2-12}$ alkylacyl (substituted, where appropriate, with $R^§$),
benzoyl, 1- and 2-naphthoyl (each substituted, where appropriate, with $R^§$),
hydroxy, sulfhydryl, formyl, carboxyl, $CONH_2$, cyano, rhodano, nitro, $SO_3H$,
alkylthio, alkylsulfinyl, $SO_2OAlk$ and alkylsulfonyl, each straight-chain, branched or cyclic $C_{1-6}$, and substituted, where appropriate, singly, doubly or triply with independently selected residues $R^§$,
arylthio, arylsulfinyl, arylsulfonyl, heteroarylthio, heteroarylsulfinyl and heteroarylsulfonyl, each substituted, where appropriate, singly, doubly or triply with independently selected residues $R^§$,
alkoxycarbonyl, $CONHAlk$ and $CONAlk_2$, each straight-chain, branched or cyclic $C_{1-6}$, and substituted, where appropriate, singly, doubly or triply with independently selected residues $R^§$,
aryloxycarbonyl, arylcarbamoyl, arylamido, N-aryl, N-alkylamido, N-aryl,N-alkylcarbamoyl, aralkyloxycarbonyl and aralkylcarbamoyl, with alkyl $C_{1-5}$, aryl $C_{6-10}$ and substituted, where appropriate, singly, doubly or triply with independently selected residues $R^§$,
heterocyclylcarbonyl, heterocyclylcarbamoyl, heterocyclylamido, N-heterocyclyl, N-alkylcarbamoyl, N-heterocyclyl, N-alkylamido, heterocyclylalkyloxycarbonyl and heterocyclylalkylcarbamoyl, with a monocyclic or bicyclic, saturated or singly or multiply unsaturated heterocycle having 5-14 ring atoms including 1-4 heteroatoms which are preferably N, O and S, substituted, where appropriate, singly, doubly or triply with independently selected residues $R^§$ and alkyl $C_{1-5}$,
chlorine, bromine, iodine, fluorine,
amino, $C_{1-6}$ alkylamino, di($C_{1-5}$)alkylamino, each straight-chain, branched or cyclic and substituted, where appropriate, singly, doubly or triply with independently selected residues $R^§$,
arylamino $C_{6-10}$, substituted, where appropriate, singly, doubly or triply with independently selected residues $R^§$,
heterocyclylamino, monocyclic or bicyclic, saturated or singly or multiply unsaturated, having 5-14 ring atoms including 1-4 heteroatoms which are preferably N, O and S, substituted, where appropriate, singly, doubly or triply with independently selected residues $R^§$, arylhydrazino, substituted, where appropriate, singly, doubly or triply with independently selected residues $R^§$, $L_A$-A-$L_B$-B wherein:

$L_A$ is single bond, $NR^\#$, O, S, SO, $SO_2$

A is phenyl, substituted, where appropriate, singly, doubly or triply with independently selected residues $R^§$ naphthyl, naphthyl substituted singly or multiply with $R^§$ monocyclic or bicyclic, saturated or singly or multiply unsaturated heterocycles having 4-14 ring atoms including 1-5 heteroatoms which are preferably N, O and S which may carry one or more oxygen atoms on C, N and/or S and are substituted, where appropriate, singly, doubly or triply with independently selected residues $R^§$ $L_A$-A can also be a direct bond tricycle-$L_B$, in this case $L_B$ being a single bond $L_B$ is single bond $NR^\#$, O, S, SO, $SO_2$, —$CHR^§$, —$CH_2$—O—, —O—$CH_2$, the following functional groups:

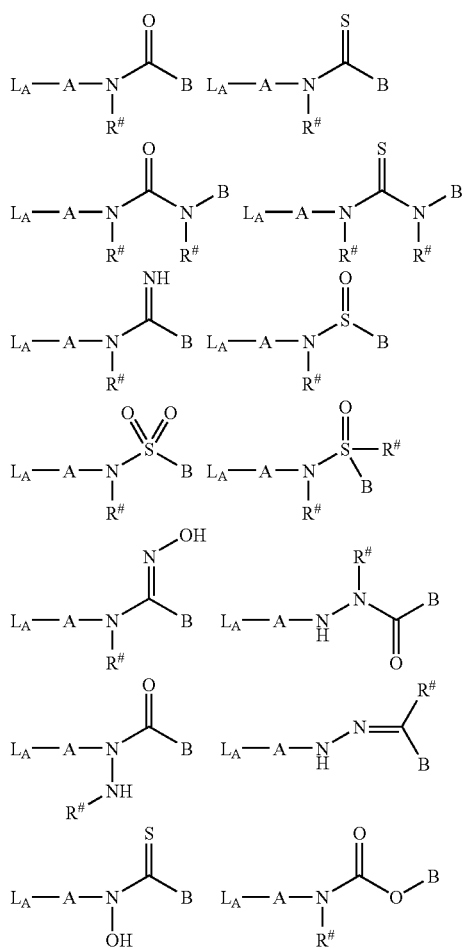

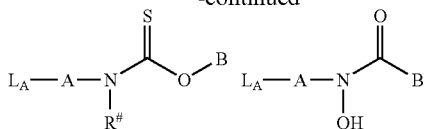

B is hydrogen alkyl, substituted, where appropriate, singly, doubly or triply independently with $R^§$ —$CONH_2$, —CONHAlk (Alk substituted, where appropriate, with $R^§$), CONHAryl (aryl substituted, where appropriate, with $R^§$), CONHHetaryl (hetaryl substituted, where appropriate, with $R^§$), —COOH, COOAlk (Alk substituted, where appropriate, with $R^§$), —COAlk (Alk substituted, where appropriate, with $R^§$), COAryl (aryl substituted, where appropriate, with $R^§$), —COHetaryl (Hetaryl substituted, where appropriate, with $R^§$)

—$CH_2$—$CONH_2$, —$CH_2$—CONHAlk (Alk substituted, where appropriate, with $R^§$), —$CH_2$—CONHAryl (Aryl substituted, where appropriate, with $R^§$), —$CH_2$—CONHHetaryl (hetaryl substituted, where appropriate, with $R^§$), —$CH_2$—COOH, $CH_2$—COOAlk (Alk substituted, where appropriate, with $R^§$)

—$CH_2$—COAlk (Alk substituted, where appropriate, with $R^§$), $CH_2$—COAryl (aryl substituted, where appropriate, with $R^§$), $CH_2$—COHetaryl (hetaryl substituted, where appropriate, with $R^§$)

phenyl, substituted, where appropriate, singly, doubly or triply with independently selected residues $R^§$, naphthyl, substituted, where appropriate, singly, doubly or triply with independently selected residues $R^§$, monocyclic or bicyclic, saturated or singly or multiply unsaturated heterocycles having 4-14 ring atoms including 1-5 heteroatoms which are preferably N, O and S which may carry one or more oxygen atoms on C, N and/or S and may be substituted, where appropriate, singly, doubly or triply with independently selected residues $R^§$, $R^\#$ is—hydrogen, alkyl, substituted, where appropriate, with $R^§$ $R^2$ is $C_{1-12}$ alkyl, $C_{2-12}$ alkenyl and $C_{2-12}$ alkinyl, benzyl, phenyl($C_{2-6}$)alkyl (substituted, where appropriate, once or several times equally or unequally with $R^§$ at the aromatic and/or aliphatic molecule portion);

phenacyl (substituted, where appropriate, with $R^§$ once or several times equally or unequally at the aromatic molecule portion);

carboxyl, $C_{1-4}$ alkoxycarbonyl, —$CONH_2$, —CONHAlk and $CONAlk_2$ ("Alk" each being $C_{1-6}$), $R^\#$/C(O)— (wherein $R^\#$ is as defined above), cyano, nitro, amino, $C_{1-6}$ alkylamino, di($C_{1-6}$)alktlamino, N=N·$C_6H_5$, —N=N—$C_6H_4$—$R^§$, 1,3-diphenyl-pyrazol-4-yl, thiazolin-2-yl, imidazolin-2-yl and 3,4,5,6-tetrahydro-pyrimidinyl;

$R^3$ is
hydrogen,
$C_{1-10}$ alkyl, $—C_{2-12}$ alkenyl, $—C_{2-12}$ alkinyl, each straight-chain, branched or cyclic and substituted, where appropriate, singly, doubly or triply with independently selected residues $R^\S$,
trifluoromethyl,
aralkyl- with $C_{6-12}$ aryl and $C_{1-5}$ alkyl, substituted, where appropriate, singly, doubly or triply with independently selected residues $R^\S$,
phenyl, substituted, where appropriate, singly, doubly or triply with independently selected residues $R^\S$,
1-naphthyl, 2-naphthyl,
pyridyl-N-oxide, (substituted, where appropriate, with $R^\S$),
$C_{1-10}$ alkoxy, straight-chain, branched or cyclic and substituted, where appropriate, singly, doubly or triply with independently selected residues $R^\S$,
aralkyloxy- with $C_{6-12}$ aryl and $C_{1-5}$ alkyl, substituted, where appropriate, singly, doubly or triply with independently selected residues $R^\S$,
$C_{2-12}$ alkylacyl (substituted, where appropriate, with $R^\S$),
benzoyl, 1- and 2-naphthoyl (each substituted, where appropriate, with $R^\S$),
hydroxy, sulfhydryl, formyl, carboxyl, $CONH_2$, cyano, rhodano, nitro, $SO_3H$
alkylthio, alkylsulfinyl, $SO_2OAlk$ and alkylsulfonyl, each straight-chain, branched or cyclic $C_{1-6}$ and substituted, where appropriate, singly, doubly or triply with independently selected residues $R^\S$,
arylthio, arylsulfinyl, arylsulfonyl, heteroarylthio, heteroarylsulfinyl and heteroarylsulfonyl, each substituted, where appropriate, singly, doubly or triply with independently selected residues $R^\S$,
alkoxycarbonyl, $CONHAlk$ and $CONAlk_2$, each straight-chain, branched or cyclic $C_{1-6}$, and substituted, where appropriate, singly, doubly or triply with independently selected residues $R^\S$,
aryloxycarbonyl, arylcarbamoyl, arylamido, N-aryl, N-alkylamido, N-aryl,N-alkylcarbamoyl, aralkyloxycarbonyl and aralkylcarbamoyl, with alkyl $C_{1-5}$, aryl $C_{6-10}$ and substituted, where appropriate, singly, doubly or triply with independently selected residues $R^\S$,
chlorine, bromine, iodine, fluorine,
amino, $C_{1-6}$ alkylamino, $di(C_{1-5})$alkylamino, each straight-chain, branched or cyclic and substituted, where appropriate, singly, doubly or triply with independently selected residues $R^\S$,
arylamino $C_{6-10}$, substituted, where appropriate, singly, doubly or triply with independently selected residues $R^\S$,
arylhydrazino, substituted, where appropriate, singly, doubly or triply with independently selected residues $R^\S$,
$R^6$ is
$CH_3$, $C_2H_5$, $(CH_2)_2CH_3$, $(CH_2)_3CH_3$, $C(CH_3)_3$, $CH_2CH_2OH$, $CH_2CH_2SH$, $CH_2CH_2SCH_3$, $CH_2CF_3$, $CH_2CCl_3$, $CH_2CHF_2$, $CH_2CHCl_2$, $CH_2CH_2F$, $CH_2CH_2Cl$, $CH_2CH_2Br$,
$C_{3-7}$ cycloalkyl [e.g. cyclopropyl, cyclopropylmethyl, cyclobutyl, cyclobutylmethyl, cyclopentyl, cyclopentylmethyl, cyclohexyl, cyclohexylmethyl] (substituted, where appropriate, on the C-skeleton with $R^\S$),
$C_{2-5}$ alkenyl and $C_{2-5}$ alkinyl,
$C_{3-7}$ cycloalkenyl,
aryl and heteroaryl as residues of monocyclic, bicyclic or tricyclic aromatic compounds or heteroaromatic compounds with 6-14 ring atoms, where appropriate [e.g. phenyl, $4-R^\S$-phenyl, $3-R^\S$-phenyl, $2-R^\S$-phenyl, $3-R^\S,4-R^\S$-phenyl, $3-R^\S,4-R^\S,5-R^\S$-phenyl],
1-naphthyl, 2-naphthyl (each substituted, where appropriate, with $R^\S$),
pyridyl, isoquinolinyl, quinolinyl, acridinyl;
$NR^7R^8$ is altogether:
morpholino, thiomorpholino, thiomorpholino-S,S-dioxide, pyrrolidino, piperidino, 1-piperazino, 1-homopiperazino, $4-C_{1-6}$-alkyl-1-piperazino, 4-(2-hydroxyethyl)-1-piperazino, 4-benzyl-1-piperazino, 4-aryl-1-piperazino (substituted, where appropriate, with $R^\S$ on the heterocycloaliphatic ring),
further amino residues of secondary, monocyclic or polycyclic cycloaliphatic amines having a total of 5-14 ring atoms, including the representatives substituted with $R^\S$ on the C-skeleton;
amino residues of secondary aliphatic and aromatic amines, $R^7R^8NH$,
wherein $R^7$ and $R^8$ may independently be equal or unequal and represent:
$C_{1-6}$ alkyl, benzyl, phenyl, 1- and 2-naphthyl, 2-, 3- and 4-pyridyl, quinolinyl, isoquinolinyl, 2-thienyl, 2-furyl (each substituted, where appropriate, with $R^\S$);
amino residues of primary amines, $R^7NH_2$, (wherein $R_7$ is the same as above),
amino, $NH_2$;
$R^\S$ is
$OH$, $—SH$, $—O—C_{1-8}$ alkyl, $—O—C_{6-14}$ aryl, $—S—C_{1-4}$ alkyl, $—S—C_{6-14}$ aryl,
$SO—C_{1-4}$ alkyl, $—SO—C_{6-14}$ aryl, $—SO_2—C_{1-4}$ alkyl, $—SO_2—C_{6-14}$ aryl, $SO_3H$,
$OSO_2C_{1-8}$ alkyl, $—OSO_2C_{6-14}$ aryl, $—COOH$, $—COOC_{1-8}$ alkyl,
$(CO)C_{1-8}$ alkyl,
$COOH$, $—CONH_2$, $—CONHC_{1-6}$ alkyl, $—CON(C_{1-6}$ alkyl$)_2$,
$NH_2$, $—NHC_{1-6}$ alkyl, $—N(C_{1-6}$ alkyl$)_2$, $—NHC_{6-14}$ aryl, $—NH$-hetaryl, $N(C_{6-14}$ aryl$)_2$, $—N(C_{1-6}$ alkyl$)(C_{6-14}$ aryl$)$,
$C_{1-6}$ alkyl, $—C_{2-12}$ alkenyl, $—C_{2-12}$ alkinyl, each straight-chain, branched or cyclic and independently substituted, where appropriate, singly, doubly or triply with halogen,
halogen (F, $—Cl$, $—Br$, $—I$),
$CH_2CH_2OH$, $—CH_2CH_2SH$, $—CH_2CH_2SCH_3$,
sulfamoyl, alkylsulfamoyl, dialkylsulfamoyl with alkyl $C_{1-5}$ substituted, where appropriate, with methoxy,
amidino, hydroxyamidino
sulfo, phosphono,
$—CN$, $—NO_2$, and $—SCN$ with the proviso that the compound of formula 1(a)(II) does not have the formula: Y=S, $R^1$=$OC_2H_5$, $R^2$=CN, $R^3$=$C_6H_5$, $R^7$=$CH_3$, $R^8$=$CH_3$, $R^6$=$C_2H_5$, a pharmaceutically compatible salt or tautomer of the at least one compound and a pharmaceutically compatible excipient and/or carrier, wherein the composition comprises a therapeutically effective amount of the at least one compound for the treatment of chronically obstructive pulmonary diseases (COPD), bronchial asthma, atomic dermatitis, or cystic fibrosis (CF).

2. A pharmaceutical composition comprising at least one compound of general formula 1(a),

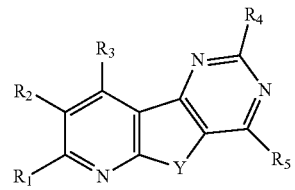

1a wherein Y=S and substituents $R^1$, $R^2$, $R^3$, $R^4$, $R^5$ are as defined below:

| $R_1$ | $R_2$ | $R_3$ | $R_4$ | $R_5$ |
|---|---|---|---|---|
| 3,4-(MeO)$_2$—Ph | H | Me | Piperazin-1-yl | OEt |
| 4-MeO—Ph | H | Me | Piperazin-1-yl | OEt |
| 4-F—Ph | H | Me | Piperazin-1-yl | OEt |
| Ph | H | Me | Piperazin-1-yl | OiPr |
| Ph | H | Me | Piperazin-1-yl | OCH$_2$CHF$_2$ |
| Ph | H | Ph | Piperazin-1-yl | OEt |
| Me | 4'-NO$_2$—Ph—CH$_2$ | Me | Piperazin-1-yl | OEt |
| Me | 4'-NH$_2$—Ph—CH$_2$ | Me | Piperazin-1-yl | OEt |
| 3,4-Methylene-dioxyphenyl | H | Me | Piperazin-1-yl | OEt |
| Ph | H | Me | Piperazin-1-yl | OnPr |
| Ph | H | Me | Piperazin-1-yl | OEt |
| Ph | H | Me | Piperazin-1-yl | OCH$_2$CH$_2$OH |
| 3,4-(MeO)$_2$—Ph | H | Me | OEt | Piperazin-1-yl |
| 4-MeO—Ph | H | Me | OEt | Piperazin-1-yl |
| Ph | H | Me | OCH$_2$CHF$_2$ | Piperazin-1-yl |
| Me | 4'-NO$_2$—Ph—CH$_2$ | Me | OEt | Piperazin-1-yl |
| Ph | 4'-NO$_2$—Ph—CH$_2$ | Me | OEt | Piperazin-1-yl |
| 3,4-(MeO)$_2$—Ph | H | Me | nPr | Piperazin-1-yl |
| Ph | H | Me | OCH$_2$CH$_2$OH | Piperazin-1-yl |
| Ph | H | Me | OEt | Piperazin-1-yl |
| Ph | H | Me | OiPr | Piperazin-1-yl |
| 3,4-Methylene-dioxyphenyl | H | Me | OEt | Piperazin-1-yl |
| 4-(Pyrimidyl-2-yl)piperazin-1-yl- | H | Et | Piperazin-1-yl | OEt |
| 4-Me—Ph | H | Et | Piperazin-1-yl | OEt |
| 4-EtO—Ph | H | Et | Piperazin-1-yl | OEt |
| 4-EtO—Ph | H | Et | Piperazin-1-yl | OProp |
| 4-MeS—Ph | H | Et | Piperazin-1-yl | OEt |
| 4-Me—Ph | H | Et | Piperazin-1-yl | OiPr |
| 4-(4-MeOPhO)Ph | H | Et | Piperazin-1-yl | OEt |
| 2,3-Dihydro-benzo[b][1,4]-dioxin-6-yl | H | Et | Piperazin-1-yl | OEt |
| 3,4-Methylene-dioxyphenyl | H | Et | Piperazin-1-yl | OEt |
| 4-MeO—Ph | H | Et | Piperazin-1-yl | OEt |
| 4-(1H-pyrazol-1-yl)-Ph | H | Et | Piperazin-1-yl | OEt |
| 4-Br—Ph | H | Et | Piperazin-1-yl | OEt |
| 4-Cl—Ph | H | Et | Piperazin-1-yl | OEt |
| 4-I—Ph | H | Et | Piperazin-1-yl | OEt |
| Morpholine | H | Ph | Piperazin-1-yl | OEt |
| 4-MeO—Ph | H | CF$_3$ | Piperazin-1-yl | OEt |
| 4-Me—Ph | H | CF$_3$ | Piperazin-1-yl | OEt |
| 2,3-Dihydro-benzo[b][1,4]-dioxin-6-yl | H | CF$_3$ | Piperazin-1-yl | OEt |
| 4-Imidazol-1-yl-Ph | H | CF$_3$ | Piperazin-1-yl | OEt |
| 4-Imidazol-1-yl-Ph | H | CF$_3$ | Piperazin-1-yl | OCH$_2$CH$_2$OH |
| 4-(Piperidin-1-yl)-Ph | H | CF$_3$ | Piperazin-1-yl | OEt |
| 4-Morpholino-Ph | H | CF$_3$ | Piperazin-1-yl | OEt |
| 3,4-Methylene-dioxyphenyl | H | CF$_3$ | Piperazin-1-yl | OEt |
| 4-MeS—Ph | H | CF$_3$ | Piperazin-1-yl | OEt |
| 4-EtOOC—Ph | H | CF$_3$ | Piperazin-1-yl | OEt |
| 4-(1H-pyrazol-1-yl)-Ph | H | CF$_3$ | Piperazin-1-yl | OEt |
| 4-F—Ph | H | CF$_3$ | Piperazin-1-yl | OEt |
| 4-I—Ph | H | CF$_3$ | Piperazin-1-yl | OEt |
| 3-NO$_2$—Ph | H | CF$_3$ | Piperazin-1-yl | OEt |
| 4-NO$_2$—Ph | H | CF$_3$ | Piperazin-1-yl | OEt |
| 3-CN—Ph | H | CF$_3$ | Piperazin-1-yl | OEt |
| 4-CN—Ph | H | CF$_3$ | Piperazin-1-yl | OEt |
| 3-NH$_2$—Ph | H | CF$_3$ | Piperazin-1-yl | OEt |
| 4-NH$_2$—Ph | H | CF$_3$ | Piperazin-1-yl | OEt |
| 4-MeS—Ph | H | CF$_3$ | Piperazin-1-yl | OEt |
| 4-MeS(O)—Ph | H | CF$_3$ | Piperazin-1-yl | OEt |
| Pyridin-4-yl | H | CF$_3$ | Piperazin-1-yl | OEt |
| Pyridin-4-yl-N-oxide | H | CF$_3$ | Piperazin-1-yl | OEt |
| Pyridin-3-yl | H | CF$_3$ | Piperazin-1-yl | OEt |

-continued

| $R_1$ | $R_2$ | $R_3$ | $R_4$ | $R_5$ |
|---|---|---|---|---|
| 4-(Pyrazin-2-yl) | H | $CF_3$ | Piperazin-1-yl | OEt |
| 4(HCONH)—Ph | H | $CF_3$ | Piperazin-1-yl | OEt |
| 4-(Pyridin-4-yl-CONH)—Ph | H | $CF_3$ | Piperazin-1-yl | OEt |
| 4-(Pyridin-3-yl-CONH)—Ph | H | $CF_3$ | Piperazin-1-yl | OEt |
| 4-(Pyridin-3-yl-N-Oxide-CONH)—Ph | H | $CF_3$ | Piperazin-1-yl | OEt |
| 4-(1H-1,2,4-triazol-4-yl)-Ph | H | $CF_3$ | Piperazin-1-yl | OEt |
| 4-(1H-pyrrol-1-yl)-Ph | H | $CF_3$ | Piperazin-1-yl | OEt |
| 4($CH_3$OOCNH)—Ph | H | $CF_3$ | Piperazin-1-yl | OEt |
| isoPr | H | isoPr | Piperazin-1-yl | OEt |
| 2,3-Dihydro-benzo[b][1,4]-dioxin-6-yl | H | Et | OEt | Piperazin-1-yl |
| 4-EtO—Ph | H | Et | OEt | Piperazin-1-yl |
| 4-Me—Ph | H | Et | OEt | Piperazin-1-yl |
| 4-Me—Ph | H | Et | $OCH_2CH_2OH$ | Piperazin-1-yl | a pharmaceutically compatible salt or tautomer of the at least one compound and a pharmaceutically compatible excipient and/or carrier, wherein the composition comprises a therapeutically effective amount of the at least one compound for the treatment of chronically obstructive pulmonary diseases (COPD), bronchial asthma, atomic dermatitis, or cystic fibrosis (CF).

* * * * *